US005234942A

United States Patent [19]

Bernstein et al.

[11] Patent Number: 5,234,942
[45] Date of Patent: Aug. 10, 1993

[54] HETEROCYCLIC AMIDES AND LEUCOTRIENE ANTAGONISTIC USE THEREOF

[75] Inventors: Peter R. Bernstein, Wilmington; Frederick J. Brown, Newark, both of Del.; Ying K. Yee, Kennett Square, Pa.

[73] Assignee: ICI Americas Inc., Wilmington, Del.

[21] Appl. No.: 628,787

[22] Filed: Dec. 17, 1990

Related U.S. Application Data

[62] Division of Ser. No. 788,807, Oct. 18, 1985, Pat. No. 4,997,844.

[30] Foreign Application Priority Data

Oct. 19, 1984 [GB] United Kingdom ................. 8426474
Mar. 21, 1985 [GB] United Kingdom ................. 8507305
Mar. 26, 1985 [GB] United Kingdom ................. 8507861
Mar. 26, 1985 [GB] United Kingdom ................. 8507862

[51] Int. Cl.$^5$ .................. C07D 201/18; C07D 407/02; A61K 31/40; A61K 31/41
[52] U.S. Cl. .................................. 514/415; 548/253; 548/481; 548/361.1; 514/381; 514/382; 514/406; 514/422; 546/279; 546/283; 546/273
[58] Field of Search ............... 548/253, 481; 514/381, 514/382, 406, 422

[56] References Cited

U.S. PATENT DOCUMENTS 4,675,405 6/1987 Musser ............................. 548/510

FOREIGN PATENT DOCUMENTS 0275221 7/1988 European Pat. Off. ........... 548/510

*Primary Examiner*—David B. Springer
*Attorney, Agent, or Firm*—Rosemary M. Miano; Thomas E. Jackson

[57] ABSTRACT

The invention provides a series of novel heterocyclic amides of the formula I in which the group A;∴CRa can be —CRb═CRa—, —CHRb—CHRa— or —N═CRa—, the amidic group Re.L can be Rd.X.CO.NH, Re.X.CS.NH or Re.NH.CO attached to position 4, 5 or 6 of the benzenoid moiety, z is an acid group selected from the group consisting of carboxy, an acylsulphonamide residue of the formula CO.NH.SO$_n$Rg and a tetrazolyl residue of the formula II and the radicals Ra, Rb, Rc, Rd, Re, Rf, Rg, Rh, n, X, G$^1$,Q and G$^2$ have the meanings defined in the following specification.

The compounds of formula I are leukotriene antagonists. The invention also provides pharmaceutically acceptable salts of the formula I compounds; pharmaceutical compositions containing the formula I compounds, or their salts, for use in the treatment of, for example, allergic or inflammatory diseases, or endotoxic or traumatic shock conditions; and processes for the manufacture of the formula I compounds, as well as intermediates for use in such manufacture.

15 Claims, No Drawings

HETEROCYCLIC AMIDES AND LEUCOTRIENE ANTAGONISTIC USE THEREOF

This is a divisional of co-pending application Ser. No. 06/788,807 filed on Oct. 18, 1985 now U.S. Pat. No. 4,897,844.

This invention concerns novel heterocyclic amides and, more particularly, novel amidoindole and amidoindazole derivatives which antagonise the pharmacological actions of the one or more of the arachidonic acid metabolites known as leukotrienes (hereafter referred to as "luekotriene antagonist properties".) The novel derivatives are useful when it is desired to antagonise one or more of the actions of the leukotrienes in vitro or in vivo, for example in the treatment of those diseases in which leukotrienes are implicated, such as in the treatment of allergic or inflammatory diseases, or endotoxic or traumatic shock conditions. The invention also provides pharmaceutical compositions containing the novel derivatives for use in such treatments and intermediates and processes for the manufacture of the novel derivatives.

In European patent applications, publication numbers 54417A1 and 80154A2, there are described a series of 3-(pyridylmethyl)indoles and 2- (pyridyl)indoles, respectively, both containing an acidic side-chain at the N(1) position and which are selective inhibitors of the enzyme thromboxane synthetase. We have now discovered a series of indole and indazole derivatives which have an amidic substituent in the benzenoid ring and which unexpectedly possess the property of antagonising one or more of the arachadonic acid metabolites known as leukotrienes and this is the basis for our invention.

According to the invention there is provided an amidic compound of the formula I (as set out hereinafter) wherein:

the group A=CRa is selected from diradicals of the formula: —CRb=CRa—, —CHRb—CHRa— and —N=CRa— in which Ra is hydrogen, methyl, halogeno, (2-6C)alkanoyl, (2-6C)alkenyl or (2-6C)alkyl, the latter two of which may optionally bear a carboxy or [(1-4C)alkoxy] carbonyl substituent, and Rb is hydrogen or (1-4C)alkyl; or Ra and Rb together form tetramethylene optionally bearing 1 or 2 (1-4C)alkyl substituents and optionally containing 1or 2 unsaturated linkages;

Rc, Rd and Rf are independently selected from hydrogen, halogeno, (1-4C)alkyl and (1-4C)alkoxy;

the group Rd.L stands for amidic radicals of the formula: Re.X.CO.NH—, Re.X.CS.NH— or Re.NH.CO— attached at position 4, 5 or 6 of the benzenoid moiety shown in formula I hereinafter, and in which Re is (2-10C)alkyl optionally containing 1 or move fluorine substituents, or is (3-10C)alkenyl or (3-10C)alkynyl; or Re is phenyl, phenyl-(1-6C)alkyl or thienyl-(1-6C)alkyl, in which the (1-6C)alkyl moiety may optionally bear a (1-4C)alkoxy, (3-6C)cycloalkyl or phenyl substituent and in which a phenyl or thienyl moiety may optionally bear 1 or 2 substituents selected from halogeno, (1-4C)alkyl, (1-4C)alkoxy and trifluoromethyl; or Re is (3-8C)cycloalkyl, (3-8C)cycloalkyl-(1-6C)alkyl or (4-6C)oxyheterocyclyl, the cyclic moiety of any of which optionally may contain one unsaturated linkage or may bear 1 or 2 (1-4C)alkyl substitutents or a phenyl substituent, the latter itself optionally bearing a halogeno, (1-4C)alkyl, (1-4C)alkoxy or trifluoromethyl substituent; X is oxy, thio, imino or a direct link to Re;

Q is a direct link to $G^1$, or is oxy, thio, m-phenylene, p-phenylene or heteroarylene;

$G^1$ is (1-8C)alkylene or (2-6C)alkenylene;

$G^2$ is methylene, vinylene or a direct link to z; and z is an acidic group selected from the group consisting of carboxy, an acylsulphonamide residue of the formula —CO.NH.SO$_n$Rg and a tetrazolyl residue of the formula II set out hereinafter, in which n is the integer 1 or 2, Rg is (1-6C)alkyl, aryl, heteroaryl, aryl-(1-4C)alkyl, in any of which the aromatic or heteroaromatic moiety may bear 1 or 2 substituents selected from halogeno, (1-4C)alkyl, (1-4C)alkoxy, trifluoromethyl, nitro and amino, and Rh is hydrogen, carboxy-(1-3C)alkyl or (carboxyphenyl)methyl; provided that $G^1$, Q and $G^2$ taken together contain at least 3 carbon atoms and that $G^2$ is methylene or vinylene when Q is oxy or thio and z is carboxy;

or a pharmaceutically acceptable salt thereof.

It will be appreciated that certain of the compounds of formula I, for example those wherein Re contains an asymmetrically substituted carbon atom, may exist in, and be isolated in, optically-active and racemic forms. In addition, it will be appreciated that certain compounds of formula I, for example those wherein Re, Ra or the linkage —$G^1$.Q.$G^2$— contains a vinylene group, exist in, and may be isolated in, separate stereoisomeric forms ('E' and 'Z') about that group, It is to be understood that the present invention encompasses any racemic, optically-active or stereoisomeric form, or mixtures thereof, which form possesses leukotriene antagonist properties, it being well know in the art how to prepare optically-active forms (for example by resolution of the racemic form of by synthesis from optically-active starting materials) and to prepare individual 'E' and 'Z' stereoisomers (for example by chromatographic separation of a mixture thereof) and how to determine the luekotriene antagonist properties by the standard tests described hereinafter.

In this specification Ra, Rb, Re et cetera stand for generic radicals and have no other significance. It is to be understood that the generic term "(1-6C)alkyl" includes both straight and branched chain alkyl radicals by references to individual alkyl radicals such as "propyl" embrace only the straight chain ("normal") radical, branched chain isomers such as "isopropyl" being referred to specifically. A similar convention applies to other generic groups, for example "alkylene" and "alkenylene" et cetera.

A particular value for Ra when it is (2-6C)alkyl is, for example, ethyl, propyl or butyl, when it is (2-6C)alkanoyl is, for example, acetyl, propionyl or butyryl; when it is halogeno is, for example, chloro or bromo; and when it is (2-6C)alkenyl is, for example, vinyl, allyl or 1-propenyl.

A particular value for an optional [(1-4C)alkoxy]carbonyl substituent which may be present on Ra is, for example, methoxycarbonyl or ethoxycarbonyl.

A particular value for Rb when it is (1-4C)alkyl is, for example, methyl or ethyl.

A particular value for Ra or Rb when together they form tetramethylene containing 1 or 2 unsaturated linkages is, for example, 1-butenylene or 1,3-butadienylene; and a particular value for an optional (1-4C)alkyl substituent thereon is, for example, methyl or ethyl.

A particular value for Rc, Rd or Rf when it is halogeno is, for example, fluoro, chloro or bromo; when it is (1–4C)alkyl is, for example, methyl or ethyl; and when it is (1–4C)alkoxy is, for example, methoxy or ethoxy.

A particular value for Re when it is (2–10C)alkyl is, for example, ethyl, propyl, isopropyl, butyl, isobutyl, sec-butyl, t-butyl, pentyl, 1-ethylpropyl, hexyl, heptyl, 1-ethylpentyl or nonyl; and when it contains 1 or more fluorine substituents is, for example, 2,2,2-trifluoroethyl or heptafluoropropyl.

A particular value for Re when it is (3–10C)alkenyl is, for example, allyl, 2-butenyl, 3-butenyl or 1,3-pentadienyl, and when it is (3–10C)alkynyl is, for example, 2-propynyl or 3-butynyl.

Particular values for Re when it is phenyl-1–6C)alkyl or thienyl-(1–6C)alkyl include, for example, benzyl, 1-phenylethyl, 2-phenylethyl, thien-2-ylmethyl, thien-3-ylmethyl, 1-phenylpropyl, 2-phenylpropyl, 3-phenylpropyl, 1-methyl-1-phenylethyl, 1- phenylbutyl and 1-phenylpentyl; and a particular value for an optional (3–6C)cycloalkyl substituent is, for example, cyclobutyl, cyclopentyl or cyclohexyl, and for an optional (1–4C)alkoxy substitutent is, for example, methoxy or ethoxy.

Particular values for certain optional substituents which may be present on a phenyl or thienyl moiety as Re, or as a part thereof, as defined above, include, for example:

for halogeno; fluoro, chloro and bromo;
for (1–4C)alkyl: methyl and ethyl; and
for (1–4C)alkoxy: methoxy and ethoxy.

A particular value for Re when it is (3–8C)cycloalkyl is, for example, cyclopropyl, cyclobutyl, cyclopentyl, cyclohexyl or cycloheptyl; when it is (3–8C)cycloalkyl-(1–6C)alkyl is, for example, cyclobutylmethyl, cyclopentylmethyl, cyclohexylmethyl, 1-cyclopentylethyl, 2- cyclopentylethyl, 1-cyclopentylpropyl, 1-dyclophexylpropyl, 1-cyclopentylbutyl, 1-cyclohexylbutyl and when it is (4–6C)oxyheterocyclyl is, for example, tetrahydrofur-2- yl, tetrahydrofur-3-yl, tetrahydropyran-2-yl, tetrahydropyran-3-yl or tetrahydropyran-4-yl; and a particular value for such a radical containing an unsaturated linkage is, for example, cyclohexenyl or cyclohexenyl-(1–6C)alkyl (such as cyclohexenylmethyl or 1-(cyclohexenyl)butyl; and a particular value for an optional (1–4C)alkyl substituent on a cyclic moeity of such a radical is, for example, methyl, ethyl or isopropyl.

A particular value for Q when it is heteroarylyene is, for example, 2,5-furandiyl, 2,5-thiophenediyl, 2,5-pyridinediyl and 4,7-benzo[b] furandiyl.

A particular value for $G^1$ when it is 1–8C)alkylene is, for example, methylene, ethylene, ethylidene, trimethylene, tetramethylene, pentamethylene, hexamethylene, heptamethylene or octamethylene; and when it is (2–6C)alkenylene is, for example, vinylene, propenylene, 1-butenylene or 2-butenylene.

A particular value for Rg when it is (1–6C)alkyl is, for example, methyl, ethyl, propyl, isopropyl or butyl; when it is aryl is, for example, phenyl, 1-naphthyl or 2-naphthyl; when it is hetroaryl is, for example, furyl, thienyl or pyridyl; when it is aryl-(1–C)alkyl is, for example, benzyl, 1-naphthylmethyl or 2-naphthylmethyl; and when it is heteroaryl-(1–4C)alkyl is, for example, furylmethyl, thienylmethyl or pyridylmethyl.

Particular values for optional substituents which may be present on an aromatic or heteroaromatic moiety as Rg, or on a part thereof, include those defined above in connection with a phenyl or thienyl moiety in Re.

A particular value for Rh when it is carboxy-(1–3-C)alkyl is, for example, carboxymethyl or 2-carboxyethyl; and when it is (carboxyphenyl)methyl is, for example o-carboxyphenylmethyl.

A typical value for Ra is, for example, hydrogen, methyl, ethyl, chloro, bromo, acetyl, propionyl or butyryl, allyl, 2-carboxyvinyl, 2-(methoxycarbonyl)vinyl or 2-(methoxycarbonyl)ethyl.

A typical value for Rb is, for example, hydrogen or methyl; and for Ra and Rb taken together is, for example, tetramethylene or 1,3- butadienylene, optionally bearing a methyl or ethyl substituent.

A typical value for Rc is, for example, hydrogen, methyl, chloro or bromo.

A typical value for Rd or Rf is for example, hydrogen, methyl, methoxy, butoxy, fluoro, chloro or bromo. Rf is preferably hydrogen.

Typical values for Re include, for example, ethyl, propyl, isopropyl, butyl, isobutyl, sec-butyl, t-butyl, pentyl, 1-ethylpropyl, hexyl, heptyl, 1-ethylpentyl, nonyl, heptafluoropropyl, 1,3-pentadienyl, 3-butynyl, phenyl, 4- methylphenyl, 2-trifluoromethylphenyl, 2-thienyl, benzyl, 4-chlorobenzyl, 4- trifluoromethylbenzyl, 4-methylbenzyl, 1- phenylethyl, 2-phenylethyl, 1-methyl-1-phenylethyl, thien-2-ylmethyl, 1-phenylpropyl, 1-phenylpentyl, alpha-cyclopentylbenzyl, alpha-methoxybenzyl, benzhydryl, cyclobutyl, cyclopentyl, cyclohexyl, 1-phenylcyclopentyl, cyclopentylmethyl, cyclohexylmethyl, 2-cyclopentylethyl, 1- cyclopentylbutyl, 1-cyclohexylpropyl, 1- cyclohexylbutyl, 5-methyl-2-(1-methylethyl)cyclohexyl, 1-cyclohexen-4-yl, tetrahydrofur-2-yl and tetrahydrofur-3yl.

A typical value for Q (including Rd and Rf) is, for example, a direct link, oxy, thio, m-phenylene, 2-methoxy-1,3-phenylene, 4-methoxy-1,3-phenylene, p-phenylene, 2-methoxy-1,4-phenylene, 2butoxy-1,4-phenylene, 2-methyl-1,4-phenylene, 2-fluoro-1,4-phenylene, 2-chloro-1,4-phenylene, 2-bromo-1,4-phenylene, 2,6-dimethoxy-1,4-phenylene, 2,5-furandiyl, or 4,7-benzol[b]furandiyl: in which $G^1$ is attached at position 1 or 4 of Q.

A typical value for $G^1$ when Q is m-phenylene or p-phenylene optionally substituted as defined above, or when Q is 2,5-furandiyl or 4,7-benzo[b]furandiyl, is, for example, methylene or ethylidene of which methylene is usually preferred.

A typical value for $G^1$ when Q is oxy or thio is, for example, trimethylene, pentamethylene, heptamethylene or 2-butenylene.

A typical value for $G^1$ when Q is a direct link is, for example, ethylene, trimethylene, tetramethylene, pentamethylene, hexamethylene or heptamethylene.

A typical value for Rg is, for example, methyl, isopropyl, butyl, phenyl, 4-fluorophenyl, 4-chlorophenyl, 2- methylphenyl, 4-methylphenyl, 4-methoxyphenyl, 4-nitrophenyl, 2-aminophenyl, 1-naphthyl, thien-2-yl or 6-chloropyrid-3-yl.

A typical value for Rh is, for example, hydrogen, carboxymethyl or o-carboxyphenylmethyl.

Two sub-groups of compounds of particular interest within the scope of the invention comprise:
(i) those compounds of formula I wherein A∴CRa stands for a diradical of the formula —CRb=CRa—, that is indoles of the formula III;

(ii) those compounds of formula I wherein A CRa stands for a diradical of the formula —N=CRa—, that is indazoles of the formula IV;

and, in either group, the remainder of the radicals have any of the above-defined values; together with the pharmaceutically acceptable salts thereof, as appropriate.

In general, in the compounds of formula III and IV it is preferred that the group Re.L is located at the 6-position of the indole or indazole ring respectively.

A preferred value for Ra is, for example, hydrogen, chloro, acetyl or butyryl and for Rb, Rc, Rf or Rh is, for example, hydrogen. A preferred value for Rd is, for example, methoxy and, when Q is p-phenylene, especially methoxy in the ortho position relative to $G^1$.

A preferred value for the assembly $G^1.Q.G^2$ (together with Rd) is, for example, 2-methoxy-alpha, 4-toluenediyl. A preferred value for Re.L is, for example, when it stands for a group of the formula Re.X.CO.NH in which Re and X have any of the meanings defined herein, and a yet more preferred value is when the radical Re.X.CO- is selected from branched (4–10C)alkanoyl [such as 2-ethylhexanoyl], 2-[(4–6C)cycloalkyl]acetyl [such as 2-(cyclopentyl)acetyl or 2-(cyclohexyl)acetyl], 2-[(2–5C)alkyl]-2-phenylacetyl [such as 2-ethyl-2-phenylacetyl], (4–6C)cycloalkyloxycarbonyl or (4–6C)cycloalkylthiolocarbonyl [such as cyclobutyloxycarbonyl, cyclopentyloxycarbonyl or cyclopentylthiolocarbonyl], (4–6C)cycloalkylcarbonyl [such as cyclopentylcarbonyl] and (3–6C)alkyloxycarbonyl [such as butyloxycarbonyl].

The group Re.L is preferably located at position 6 of the nucleus of the formula I compounds.

A preferred value for Rg is, for example, phenyl optionally bearing a fluoro, chloro, methyl, nitro or amino substituent; and especially phenyl or 2-methylphenyl.

A particularly preferred value for Z is, for example, when it is an acylsulphonamide residue of the formula —CO.NH.SO$_2$.Rg (wherein Rg has any of the meanings defined above).

Specific compounds of formula I are described in the accompanying Examples. However, of these, (a) the sulphonamides (Z=CO.NH.SO$_2$Rg) described in Examples 256, 261, 262, 263, 264, 265, 266, 277, 278, 279, 280, 284, 294 and 298; (b) the carboxylic acids (Z=CO$_2$H) described in Examples 114, 122, 170, 176, 209, 221, 222, 224 and 241; and the tetrazoles (Z=5-1(H)-tetrazolyl) described in Examples 157, 158, 161, 162 and 163; together with their pharmaceutically acceptable base-addition salts; are of special interest for their potent leukotriene antagonist properties.

The compounds of formula I may form salts with bases and those salts which are pharmaceutically acceptable are included within the invention. Examples of suitable pharmaceutically acceptable salts include salts with bases forming a physiologically acceptable cation, such as alkali metal, (especially sodium and potassium), aluminium and ammonium salts, as well as salts of appropriate organic bases such as triethylamine, morpholine, piperidine and triethanolamine.

The compounds of formula I may be made by processes well known in the chemical art for the production of structurally analogous compounds. Such processes for the manufacture of a compound of formula I as defined hereinbefore are provided as further features of the invention and are illustrated by the following procedures: (Z=CO$_2$H) described in Examples 114, 122

(a) For those compounds of formula I wherein Z is a carboxylic acid group, decomposing a suitable ester of formula V wherein Ri is, for example, (1–6C)alkyl optionally bearing an acetoxy, (1–4C)alkoxy or (1–4C)alkylthio substituent, or is phenyl or benzyl.

A particular value for Ri is, for example, methyl, ethyl, propyl, t-butyl, acetoxymethyl, methoxymethyl, 2-methoxyethyl, methylthiomethyl, or phenyl or benzyl).

It will be appreciated that the decomposition can be performed using any of a variety of procedures well known in the art for organic chemistry. Thus, it may be carried out, for example, by conventional hydrolysis under acid or base conditions, adjusted as necessary to minimise any hydrolytic removal of other functional groups in the molecule. Alternatively, it may in certain circumstances, for example when Ri is t-butyl, by possible to carry out the decomposition by thermal means, for example by heating the ester of formula V at a temperature of, for example 100°–150° C., alone or in a suitable solvent or diluent such as diphenylether. In addition, when Ri is t-butyl, the decomposition may be performed, for example using trimethylsilyl triflate as illustrated in the accompanying Example 172. Still further, in certain circumstances, for example when Ri is benzyl, it may be possible to carry out the decomposition by reductive means, for example by use of hydrogen at about atmospheric pressure in the presence of a suitable catalyst, such as palladium or platinum, conveniently on charcoal as a support.

A preferred method for hydrolysing an ester of formula V comprises reacting said ester with a suitable base, for example an alkali or alkaline earth metal hydroxide or carbonate (such as lithium hydroxide, potassium hydroxide, sodium hydroxide, calcium hydroxide or potassium carbonate) in a suitable, aqueous solvent or diluent, for example water optionally together with a water miscible alkanol, glycol. ketone or ether (such as methanol, ethanol, ethylene glycol, 2-methoxyethanol, acetone, methyl ethyl ketone, tetrahydrofuran or 1,2-dimethoxyethane), at a temperature of, for example, 15°–100° C. and conveniently at or near ambient temperature. When such a method is employed, the resultant carboxylic acid of formula I wherein Z is a carboxylic acid group is initially obtained as the corresponding salt of the base used for the hydrolysis and may be isolated as such or converted to the free acid form by a conventional acidification procedure, for example by reaction with a suitable strong acid such as hydrochloric or sulphuric acid.

(b) For those compounds of formula I wherein Re.L stands for a group of the formula Re.X.CO.NH— or Re.X.CS.NH—, acylating an amine of the formula VI.

A suitable acylating agent when X is oxy, thio, or a direct link is, for example an acid halide of the formula Re.Xa.CO.Hal or Re.Xa.CS.Hal wherein Xa is one of above-mentioned values for X and Hal is halogeno, especially chloro or bromo.

A suitable acylating agent when X is imino is, for example, an isocyanate or isothiocyanate of the formula Re.NCO or Re.NCS.

When an acid halide is used as the acylating agent, a suitable base such as triethylamine, N-methylmorpholine, pyridine or 2,6-luitidine is conveniently also employed, preferably together with a suitable inert solvent or diluent for example methylene chloride, diethyl ether, tetrahydrofuran or 1,2-dimethoxyethane. The same or similar inert solvents or diluents are used when an isocyanate or isothiocyanate is employed as the acylating agent.

When X is a direct link, the acylating agent may also be a carboxylic acid of the formula Re.CO$_2$H in which case a suitable condensing agent, for example a carbodiimide [such as is referred to in (g) hereinafter] or 1,1'-carbonyldiimidazole is generally employed, preferably together with a suitable inert solvent or diluent, for example one of those mentioned above for use with an acid halide.

In general, the acylations are carried out at a temperature in the range, for example, 0°–60° C. and, conveniently, at or near ambient temperature.

(c) For those compounds of formula III or IV, reacting an indole or indazole derivative of the formula VII wherein A is =CH- or -N= with an alkylating agent of the formula VIII in which U is a suitable leaving group, for example, halogeno (especially chloro, bromo or iodo) or alkane- or arene-sulphonyloxy (especially methanesulphonyloxy or p-toluenesulphonyloxy).

The reaction is preferably performed in the presence of a suitable base, for example an alkali metal hydride such as sodium or potassium hydride in a suitable inert solvent or diluent, for example, tetrahydrofuran, 1,2-dimethoxyethane, N-methylpyrrolidone, or N,N-dimethylformamide. Alternatively, the indole or indazole derivative of formula VII may be used in the form of its preformed anhydrous alkali metal salt, for example by prior reaction with a molecular equivalent of a suitable base such as sodium or potassium methoxide or hydride or butyl lithium; in which case a wider range of conventional solvents or diluents may be employed for the reaction with the alkylating agent of formula VIII. In either case, the alkylation is generally performed at a temperature in the range, for example, −10° to 40° C. and, conveniently, at or near ambient temperature.

(d) For those compounds of formula I wherein Z is a 1 (H)-tetrazol-5-yl radical of formula II (Rh=H), reacting a cyano derivative of the formula IX with an azide.

A particular, suitable azide is, for example, an alkali metal azide such as sodium or potassium azide, preferably together with an ammonium halide, for example ammonium chloride or ammonium bromide or, especially, with triethylammonium chloride. The reaction is preferably performed in a suitable polar solvent, for example N,N-dimethylformamide or N-methylpyrrolidone, and conveniently at a temperature in the range, for example, 50° to 160° C.

(e) For those compounds of formula I wherein Ra is halogeno, halogenating the corresponding compound of formula I wherein Ra is hydrogen.

The reaction may be carried out using a conventional halogenating procedure known in the art of heterocyclic chemistry and which is compatible with the other groups present in the compound. Thus, for example, a chloro or bromo substituent may be incorporated using N-chloro or N-bromo succinimide or a comparable N-halogeno reagent, conveniently in a suitable solvent, for example, a halocarbon solvent such as chloroform or carbon tetrachloride, and at a temperature in the range, for example 20°–100° C.

(f) For a compound of formula I wherein Re.L stands for a group of the formula Re.X CO.NH or Re.X.CS.NH in which is oxy, imino or thio, reacting an isocyanate or isothiocyanate of the formula X, wherein Xb is oxygen or sulphur, with the appropriate compound of the formula Re.XH, for example an amine of the formula Re.NH$_2$, an alcohol of the formula Re.OH or a thiol of the formula Re.SH.

In general, the process is performed at a temperature in the range, for example, 0°–60° C. and, conveniently in a suitable inert diluent or solvent such as methylene chloride, diethyl ether, methyl t-butyl ether, tetrahydrofuran or dioxane. The starting isocyanate or isothiocyanate of formula X may conveniently be obtained by reaction of the corresponding amine of formula VI with phosgene or thiophosgene (or an equivalent reagent, such as trichloromethyl chloroformate for the production of an isocyanate) in a conventional manner.

(g) For a compound of formula I wherein Z is a group of the formula CO.NH.SO$_n$.Rg, reacting a compound of formula I wherein Z is carboxy (hereinafter "acid of formula I") with a sulphonamide derivative of the formula Rg.SO$_n$.NH$_2$.

Thus, for example a free acid of formula I may be reacted with a suitable dehydrating agent, for example with dicyclohexylcarbodiimide or 1-[3-(dimethylamino)propyl]-3-ethylcarbodiimide, or with a hydrochloride or hydrobromide salt thereof, optionally together with an organic base, for example 4-(dimethylamino)pyridine, in the presence of a suitable solvent or diluent, for example methylene chloride, at a temperature in the range, for example 10° to 50° C., but preferably at or near ambient temperature. Alternatively, a reactive derivative of an acid of formula I, for example an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt) of the appropriate sulphonamide of the formula Rg.SO$_2$NH$_2$, conveniently at or near room temperature and in a suitable solvent or diluent, for example tetrahydrofuran, N,N-dimethylformamide or methylene chloride.

(h) For a compound of formula I wherein Ra bears a carboxy substituent and/or Rh is carboxy-(1–3C)alkyl or (carboxyphenyl)methyl, decomposing a corresponding ester of formula I wherein Ra bears a [(1–6C)alkoxy]carbonyl substituent and/or [(1–6C)alkoxy]carbonyl-(1–3C)alkyl or [(1–6C)alkoxycarbonylphenyl]methyl.

In general, similar decomposition conditions to those described in process (a) may be used.

(i) For a compound of formula I wherein Z is an acylsulphonamide group of the formula CO.NH.SO$_n$.Rg, G$^2$ is a direct link to Z and Q is oxygen or sulphur, reacting a compound of the formula XI wherein Xb is oxy or thio, with an isocyanate derivative of the formula OCN.SO$_n$.Rg.

The process may be carried out under generally similar conditions to those described for process (f) hereinabove.

(j) For a compound of formula I wherein Z is an acylsulphoamide group of the formula CO.NH.SO$_2$.Rg, oxidising the corresponding acylsulphinamide of the formula I wherein Z is a group of the formula CO.NH.SO.Rg.

The process may be carried out using any conventional oxidising agent known for the production of sulphones from sulphoxides and which is compatible with the presence of other sensitive groupings in the molecule concerned. Thus for example, hydrogen peroxide, gaseous oxygen in the presence of platinum, potassium permanganate, chromium trioxide or alkaline persulphate may be used, conveniently in a suitable polar solvent or diluent such as aqueous acetone or tetrahydrofuran and at as low a temperature as possible, consistent with a reasonable reaction rate, for example at or near ambient temperature, that is in the range 15°-30° C.

(k) For a compound of formula I wherein Ra is (2-6-C)alkyl optionally bearing a carboxy or [(1-4C)alkoxy]carbonyl substituent, reducing the corresponding compound of formula I wherein Ra is (2-6C)alkenyl optionally bearing a carboxy or [(1-4C)alkoxy]carbonyl substituent.

The reduction may in general be performed using conventional hydrogenation conditions, for example using hydrogen at a pressure of, for example, 1-4 bar in the presence of a suitable catalyst, for example, a noble metal catalyst such as palladium or platinum, conveniently on an inert support such as carbon, in a suitable solvent or diluent, for example, a (1-4C)alkanol (such as methanol or ethanol) or in tetrahydrofuran, optionally in the presence of water and at a temperature in the range, for example, 15°-35° C.

For compounds of formula I wherein A is nitrogen, selective positioning of $G^2$ at the N(1) position may be achieved by the chlorination of a compound of formula XII (Ra=H) followed by alkylation and reduction of the corresponding chloro compound (XII, Ra=Cl) to give the amine starting material of formula VI (Ra=H), for example as described in Example 306.

Whereafter, for any of the above procedures, when a pharmaceutically acceptable salt is required, it may be obtained by reaction of the acidic form of the formula I compound with a base affording a physiologically acceptable cation, or by any other conventional procedure.

The necessary starting materials for the above procedures may be made by standard techniques of organic chemistry and by analogy with the synthesis of known, structurally similar, compounds. Thus, for example, the starting esters of formula V may be made using the general procedure described for process (b) hereinbefore but starting from the analogous amine to formula VI (i.e. wherein Z is a group of the formula—$CO_2Ri$) or using the general procedure described for process (c) hereinbefore starting from the indole or indazole derivative of formula VII and the analogous alkylating agent of formula VIII (i.e. wherein Z is a group of the formula —$CO_2Ri$). The starting amines of formula VI may be obtained, for example, by alkylating an appropriate nitroindole or nitroindazole derivative of formula XII using an alkylating agent of the formula VIII in the presence of a suitable base such as potassium carbonate, in a solvent such as acetone, followed by a conventional reduction to give the required amine of formula VI. The amines of formula VI or the corresponding esters (i.e. wherein Z is a group of the formula —$CO_2Ri$) may also be conveniently obtained for use in situ in the acylation process (b) hereinabove when the acylating agent is a free carboxylic acid of formula Re.$CO_2H$, by reduction of the corresponding nitro compound, for example, by catalytic hydrogenation or by use of a reducing metal system, for example iron or zinc dust in an excess of the acid of formula Re.$CO_2H$.

The starting indole and indazole derivatives of formula VII may be obtained, for example:

(i) from the nitro derivatives of formula XII i.e. by conventional reduction to the corresponding amine of formula XIII followed by acylation using the same general procedure as described in (b) above; or (ii) when Re.L stands for Re.NH.CO—, from the appropriate indole or indazole carboxylic ester of formula XIV, wherein Ri has the meaning stated above, (preferably methyl, ethyl or phenyl) by reaction with the appropriate amine of the formula Re.$NH_2$.

The starting materials of formula XI may be made, for example, by analogy with the method described in Example 301 hereinafter. The production of the majority of the above starting materials is illustrated in the accompanying Examples. The ester starting materials of formula V are novel and are valuable intermediates, provided as a further feature of the invention.

As stated previously, the compounds of formula I possess leukotriene antagonist properties. Thus they antagonise the actions of, one or more of the arachidonic acid metabolites known as leukotrienes for example, $C_4$, D4 and/or E4, which are known to be powerful spasmogens (particularly in the lung), to increase vascular permeability and have been implicated in the pathogenesis of asthma and inflammation (see J. L. Marx, Science, 1982, 215, 1380–1383) as well as of endotoxic and traumatic shock. The compounds of formula I are thus useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

The compounds of formula I are potent leukotriene antagonists and are useful whenever such activity is desired. For example, the compounds of formula I are useful as pharmacological standards for the development and standardisation of new disease models and assays for use in developing new therapeutic agents, as well as for treating the diseases in which the leukotrienes are implicated.

When used in the treatment of one or more of the above mentioned diseases, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg. (and typically 5 to 100 mg.) of a compound of formula I may conveniently be used. Similarly, for intravenous or intramuscular injection or infusion a sterile solution or suspension containing up to 10% w/w (and typically 0.05 to 5% w/w) of a compound of formula formula I may conveniently be used.

The dose of compound of formula I to be administered will necessarily be varied according to principles well known in the art taking account of the route of administration and the severity of the condition and the size and age of the patient under treatment. However, in general, a compound of formula I will be administered to a warm-blooded animal (such as man) so that a dose in the range, for example 0.05 to 25 mg./kg. (and usually 0.5 to 10 mg.kg.) is received.

The leukotriene antagonist properties of a compound of formula I may be demonstrated using standard tests. Thus, for example, they may be demonstrated in vitro using the standard guinea-pig tracheal strip preparation described by Krell (*J. Pharmacol. Exp. Ther.* 1979, 211, 436). Using this procedure, tracheal tissue strips are set up in groups of eight, four being used as time/vehicle controls and four for each test compound. All of the strips are exposed to $8 \times 10^{-9}M$ leukotriene $E_4(LTE_4)$ following the 50 minute equilibration period, and the response recorded. This concentration of $LTE_4$ is that which produces a contraction equal to about 70–80% of the maximal effect of the agonist in this tissue. The $LTE_4$ is washed out for 40–45 minutes and the procedure repeated twice to ensure that reproducible responses are being obtained with $LTE_4$. Leukotriene $C_4$ $(LTC_4)$ or $D_4(LTD_4)$, at a concentration of $8 \times 10^{-9}M$, may be substituted for $LTE_4$ in the same procedure.

Once tissue reproducibility has been established, test compounds are added to four baths following the 40 to 45 minute washout period. After a 10 minute incubation with test compound or vehicle, $8 \times 10^{-9}M$ $LTE_4$, $LTD_4$ or $LTC_4$ is added and the response recorded. The percentage inhibition by the test compound or the percentage change in vehicle controls is calculated, for each tissue, according to the following equation: % inhibition = 100 multiplied by (mg. tension increase of preceding response minus mg. tension increase in presence of compound) divided by mg. tension increase in presence of compound) divided by mg. tension increase of preceding response. The mean percentage change for vehicle controls and test compound are calculated and evaluated for significant differences by Students' t-test for unpaired data. Tissues exposed to test compounds were retested for responsiveness to $LTE_4$, $LTD_4$ or $LTC_4$ following a 25 minute washout period. If tissue responsiveness was equal to responsiveness preceding exposure to the test compound additional studies were conducted. If responsiveness was not restored by the washing procedure, the tissues were discarded. The cyclooxygenase inhibitor, indomethacin, is present at $5 \times 10^{-6}M$ in all the determinations.

In general, the compounds of formula I demonstrate statistically significant activity as $LTC_4$, $LTD_4$ and/or $LTE_4$ antagonists in the above test at a concentration of about $10^{-5}M$ or much less.

The selectivity of action as leukotriene antagonists as opposed to non-specific smooth muscle depressants may be shown by carrying out the above in vitro procedure using the non-specific spasmogen barium chloride at a concentration $1.5 \times 10^{-3}m$, again in the presence of indomethacin at $5 \times 10^{-6}M$.

Activity as a leukotriene antagonist may also be demonstrated in vivo in laboratory animals, for example in a routine guinea-pig aerosol test in which guina-pigs are pre-dosed with test compound (generally between 15 minutes to 1 hour) before an aerosol challenge of leukotriene $LTD_4$ (30 micrograms/ml.) and the effect of the test compound on the average time of leukotriene initiated change in breathing pattern (such as onset of dyspnoea) recorded and compared with that in undosed, control guinea-pigs. In general, compounds of formula I produce a significant increase in the time of onset of leukotriene initiated breathing changes following either oral, intravenous or intra peritoneal administration at a dose of 100 mg./kg., or much less, without any indication of untoward side-effects at several multiples of the minimum effective dose. By way of example, the compounds described in Examples 262, 158 and 168 produced significant increases in time required for onset of leukotriene $D_4$ initiated disponoea following oral dosing at about 5 mg./kg., 43 mg./kg. and 50 mg./kg., respectively, 1–2 hours prior to leukotriene challenge.

The invention will now be illustrated by the following non-limiting Examples in which, unless stated otherwise:

(i) all operations were carried out at room or ambient temperature that is at a temperature in the range 18°–25° C.

(ii) evaporation of solvent was carried out using a rotary evaporator in vacuo with a bath temperature of up to 50° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm. silica gel GHLF plates (Art. 21521), obtainable from Analtech, Newark, Del., USA;

(iv) melting points are uncorrected and 'd' indicates decomposition;

(v) all final products were essentially pure by TLC;

(vi) yields are given for illustration only and, for crystalline end-products, refer to the weight of recrystallised solid except where shown with an asterisk*; carboxylic acid end-products were recrystallised from, for example, ethyl acetate/hexane (vii) when given, NMR data is in the form of delta values for major diagnostic protons, given in parts per million (ppm) relative to tetramethylsilane (TMS) as internal standard, determined at 80 MHz or 250 MHz using $CDCl_3$ or $d_6$-DMSO as solvent; conventional abbreviations for signal shape are used e.g. s, single; d, doublet; m, multiplet; br, broad; etc.; and (viii) chemical symbols have their usual meanings; the following abbreviations have also been used: v (volume), w (weight), m.p. (melting point), p.s.i. (pounds per square inch), [liter(s)], m.l. (milliliters), g [grams(s)]; and in center of the Tables+ is used to indicate that an explanatory footnote applies.

EXAMPLE 1

A stirred solution of 0.45 g. methyl 4-(6-aminoindol-1-ylmethyl)-3-methoxybenzoate (A) in 10 ml. methylene chloride was cooled to 0° C. and treated with 0.30 m.. triethylamine followed by 0.22 ml. hexanoyl chloride. The resulting solution was stirred at 0° C. for 15 minutes and then at room temperature for 30 minutes. The mixture was diluted with ethyl acetate and poured into cold water. The organic layer was washed sequentially with 10% v/v hydrochloric acid, water, and brine; dried (MgSO$_4$) and evaporated. The residue was purified by flash chromatography on a $4 \times 18$ cm. silica gel column using 35% (v/v) ethyl acetate in hexane as the eluent to give 0.36 g. (61%) of methyl 4-(6-hexanamidoindol-1-ylmethyl)-3-methoxybenzoate as a white solid; NMR: 0.9 (t, 3H, $CH_3CH_2$), 1.4 (m, 4H, $CH_3CH_2CH_2$), 1.7 (m, 2H, $CO.CH_2CH_2$), 2.3 (t, 2H, $CO.CH_2$), 3.9 (s, 3H, $OCH_3$), 4.0 (s, 3H, $OCH_3$), 5.3 (s, 2H, $NCH_2$), 6.5 (d, 1H, $H^3$-indole), 6.6 (d, 1H, m-

MeO.C$_6$H$_3$), 6.9 d, 1H, H$^5$-indole), 7.1 (d, 1H, H$^2$-indole), 7.2 (br s, 1H, NH), 7.5 (d, 1H, p-MeO:C$_6$H$_3$), 7,6 (m, 2H), 8.0 (br s, 1H, H$^7$-indole). The amino ester A was obtained as follows:

(a) A solution of 4.0 g. 6-nitroindole and 6.71 g. methyl 4-bromomethyl-3-methoxybenzoate (B) in 125 ml. dry acetone was treated with 4.0 g. anhydrous potassium carbonate. The mixture was heated under reflux for 48 hours. The cloudy mixture was evaporated. The residue was suspended in ethyl acetate, and solid removed by filtration. The filtrate was evaporated and the residual oil was purified by flash chromatography on a 6×30 cm. column of silica gel using 50% (v/v) methylene chloride in hexane as the eluent to give 8.0 g. (95%) of methyl 3-methoxy-4-(6-nitroindol-1-ylmethyl)benzoate (C) as a bright yellow powder; NMR: 3.9 (s, 3H, OCH$_3$), 4.0 (s, 3H, OCH$_3$), 5.4 (s, 2H, NCH$_2$), 6.7 (dd, 1H,H$^3$-indole), 6.8 (d, 1H, m-MeO.C$_6$H$_3$) 7.4 (d, 1H, H$^2$-indole), 7.5–7.7 (m, 3H), 8.0 (dd, 1H, H$^5$-indole), 8.3 (br s, 1H, H$^7$-indole).

(b) A solution of 1.38 g. C in 15 ml. ethyl acetate, which contained 2 drops of 20% (v/v) acetic acid in ethyl acetate, was added to a suspension of 0.34 g. of pre-reduced 10% w/w palladium-on-charcoal in 5 ml. ethyl acetate. The mixture was shaken under 3.45 bar hydrogen for 24 hours and then filtered through diatomaceous earth. The residue was washed with hot chloroform and the combined filtrate and washings were evaporated to give 1.19 G. (95%) of methyl 4-(6-amino-indol-1-ylmethyl)-3-methoxybenzoate (A) as a tan powder; NMR:3.6 (br, 2H, NH$_2$), 3.9 (s, 3H, OCH$_3$), 4.0 (s, 3H, OCH$_3$), 5.3 (s, 2H, NCH$_2$), 6.4 (d, 1H, H$^3$-indole), 6.5 (s, 1H, H$^7$-indole), 6.6 m, 2H), 6.9 (d, 2H, H$^2$-indole), 7.5 (m, 3H).

The starting bromomethyl compound B was itself obtained as follows:

(c) A solution of 6.0 g. 3-methoxy-4-methylbenzoic acid in 120 ml. of methanol was treated with 6 ml. acetyl chloride and stirred for 36 hours. The solution was evaporated. The residue was dissolved in 100 ml. methanol and the solution evaporated. This procedure was repeated to give 6.34 g. (98%) of methyl 3-methoxy-4-methylbenzoate (D) as a colourless oil; NMR: 2.2 (s, 3H, CH$_3$), 3.9 (2s, 6H, OCH$_3$), 7.1 (d, 1H, m—MeO.C$_6$H$_3$), 7.5 (m, 2H).

(d) A stirred solution of 121.2 g. methyl 3-methoxy-4-methylbenzoate (D) in 1.4 l. carbon tetrachloride was heated under gentle reflux with a 350 watt tungsten lamp and subjected to an air purge by means of a T-tube attached to a water aspirator. A solution of 107.2 g. bromine in 500 ml. carbon tetrachloride was added dropwise over 4 hours. Evaporation of the solvent gave a light yellow solid which was triturated with 500 ml. of 10% (v/v) ether in hexane. The solid was collected by filtration to give 111.7 g. (64%) of methyl 4-bromomethyl-3-methoxybenzoate (B) as a light yellow solid, m.p. 87°–90° C.; NMR: 3.9 (2s, 6H, OCH$_3$), 4.5 (s, 2H, BrCH$_2$), 7.4 (m, 3H, aromatic H).

EXAMPLES 2-8

Using a similar procedure to that described in Example 1 starting from the appropriate acid chloride of the formula Re.C0.Cl, the following esters of formula I were obtained:

| Example | Re | Yield (%) | Partial NMR |
|---|---|---|---|
| 2 | Propyl | 100 | 0.9(t, 3H, CH$_2$C$\underline{H}_3$), |

-continued

| Example | Re | Yield (%) | Partial NMR |
|---|---|---|---|
| | | | 2.6(m, 2H, C$\underline{H}_3$CH$_2$), 2.3(t, 2H, CO.C$\underline{H}_2$) |
| 3 | Heptyl | 96 | 0.9(t, 3H, CH$_2$C$\underline{H}_3$), 1.2(m, 8H), 1.6(m, 2H, CO.CH$_2$C$\underline{H}_2$), 2.3(t, 2H, CO.C$\underline{H}_2$). |
| 4 | Nonyl | 70 | 0.9(t, 3H, CH$_2$C$\underline{H}_3$), 1.3(m, 12H), 1.7(m, 2H, CO.CH$_2$C$\underline{H}_2$), 2.4 (t, 2H, CO.C$\underline{H}_2$) |
| 5 | 1,3-Pentadienyl | 60 | 1.9(m, 3H, C$\underline{H}$CH$_3$), 5.8–6.2(m, 3H, vinyl) |
| 6 | Benzyl | 79 | DMSO: 3.6(s, 2H, C(O)CH$_2$) |
| 7 | 2-Phenylethyl | 41 | 2.7(t, 2H, PhC$\underline{H}_2$), 3.0(t, 2H, CO.CH$_2$) |
| 8 | 3-Phenylpropyl | *22 | 2.0–2.4(m, 4H, PhC$\underline{H}_2$C$\underline{H}_2$), 2.7 (t, 2H, CO.CH$_2$) |

*Note: acid chloride prepared in situ with thionyl chloride.

EXAMPLE 9

A solution of 0.318 g. 2-phenylbutyric acid and 0.335 g. 1,1′-carbonylidiimidazole in 2 ml. methylene chloride was heated under reflux for 30 minutes and then treated with a solution of 0.5 g. methyl 4-(6-amino-indol-1-ylmethyl)-3-methoxybenzoate (A) in 2 ml. methylene chloride. The mixture was heated under reflux for 30 minutes, stirred at room temperature for 24 hours, and then diluted with ethyl acetate. This organic solution was washed sequentially with 10% v/v hydrochloric acid, water, and brine, dried (MgSO$_4$) and evaporated. The residue was purified by flash chromatography on a 4×18 cm. silica gel column using 60% v/v ethyl acetate in hexane as the eluent to give 0.493 g. (74%) of methyl 3-methoxy-4-[6-(2-phenylbuanamido)indol-1-ylmethyl]-benzoate as a white solid; NMR: 0.9 (t, 3H, CH$_2$CH$_3$), 2.0 (m, 2H, CH$_3$CH$_2$), 3.4 (m, 1H, PhCH), 3.9 (s, 3H, OCH$_3$), 4.0 (s, 3H, OCH$_3$), 5.3 (s, 2H, NCH$_2$), 6.5 (d, 1H, H$^3$-indole), 6.7 (m,2H), 7.1 (d, 1H, H$^2$-indole), 7.2 (br, 1H, NH), 7.4 (m, 8H, aromatic H), 7.9 (br s, 1H, H$^7$-indole).

EXAMPLES 10-14

Using a similar procedure to that described in Example 9 but starting from the appropriate carboxylic acid of the formula Re.CO$_2$H, the following esters of the formula 1 were obtained.

| Example | Re | Yield (%) | Partial NMR |
|---|---|---|---|
| 10 | 3-butyn-1-yl | 95 | 2.0(m, 1H, HC≡C), 2.6(br s, 4H, CO.C$\underline{H}_2$C$\underline{H}_2$) |
| 11 | 4-chlorobenzyl | 100 | 3.7(s, 2H, CO.CH$_2$) |
| 12 | 4-CF$_3$-benzyl | 62 | 3.7(s, 2H, CO.CH$_2$) |
| 13 | benzhydryl | 64 | 5.1(s, 1H, CO.CH), 7.3[s, 10H, (C$_6$H$_5$)$_2$] |
| 14 | 2-thienylmethyl | 47 | 3.9(m, 8H, 2 OCH$_3$ + CO.CH$_2$) |

EXAMPLE 15

Using an analogous procedure to that described in Example 1 but starting form 6-nitroindoline, there was obtained methyl 4-(6-hexanamidoindolin-1-ylmethyl)-3-methoxybenzoate as an amber syrup in 28% yield; NMR: 0.9 (br t, 3H, CH$_3$CH$_2$), 1.3 (m, 4H, CH$_3$CH$_2$CH$_2$), 1.7 (m, 2H, CO.CH$_2$CH$_2$), 2.3 (t, 2H, CO.CH$_2$), 3.0 (m, 2H, NCH$_2$CH$_2$), 3.5 (m, 2H, NCH$_2$CH$_2$), 3.9 (s, 6H, OCH$_3$), 4.3 (s, 2H, NCH$_2$), 6.6–7.0 (m, 3H, aromatic-H), 7.3–7.7 (m, 3H, aromatic-H).

EXAMPLE 16

A solution of 2.50 g. methyl 4-(6-aminoindol-1-ylmethyl)-3-methoxybenzoate (A) in 20 ml. methylene chloride was mixed with 0.92 ml. butyl isocyanate and then stirred for 72 hr. Evaporation gave an oil which solidified upon trituration with ethyl acetate to yield 3.3 g. (100%) of methyl 4-(6-N'-butylureidoindol-1-ylmethyl)-3-methoxybenzoate; NMR: 0.9 (m, 3H, CH$_2$CH$_3$), 1.3 (m, 4H, CH$_3$CH$_2$CH$_2$), 3.2 (br q, 2H NHCH$_2$), 3.9 (s, 3H, OCH$_3$), 4.0 (s, 3H, OCH$_3$), 4.9 (br t, 1H, CH$_2$NH), 5.3 (s, 2H, NCH$_2$), 6.4 (br s, 1H, ArNH), 6.5 (d, 1H, H$^3$-indole), 6.7 (d, 1H, m-MeOC$_6$H$_3$, 6.8 (dd, 1H, H$^5$-indole), 7.1 (d, 1H, H$^2$-indole), 7.5 (m, 4H).

EXAMPLES 17–20

Using an analogous procedure to that described in Example 16 but starting with the appropriate isocyanate or isothiocyanate, the following esters of formula 2 were obtained:

| Example | Re | Xa | Yield (%) | Partial NMR |
| --- | --- | --- | --- | --- |
| 17 | t-Butyl | O | 46% | 1.3(s, 9H, t-Bu), 4.6(br s, 1H, t-BuNH) |
| 18 | Hexyl | O | 85% | 0.9(m, 3H, CH$_2$CH$_3$), 1.3(m, 8H,)3.2 (br q, 2H, NHCH$_2$), 5.0(br t, 1H, CH$_2$NH) |
| 19 | Benzyl | O | 100% | 4.4(d, 2H, PhCH$_2$), 5.1(br t, 1H, CH$_2$NH) |
| 20 | Butyl | S | 68% | 0.9(m, 3H, CH$_2$CH$_3$), 1.4(m, 4H, CH$_3$CH$_2$—CH$_2$), 3.6(br q, 2H NHCH$_2$), 5.9(br t, CH$_2$NH). |

EXAMPLE 21

Using a similar procedure to that described in Example 9 but starting with cyclopentanecarboxylic acid instead of 2-phenylbutyric acid, methyl 4-(6-cyclopentancarboxamidoindol-1-ylmethyl)-3-methoxybenzoate was obtained as a solid in 56% yield; partial NMR: 1.5–2.0 [br m, 8H, (CH$_2$)$_4$], 2.5–2.8 [br m, 1H, (CH$_2$)$_4$CH], 7.2 (br s, 1H, NH).

EXAMPLE 22

A solution of 3.0 g. methyl 4-(6-aminoindol-1-ylmethyl)-3-methoxybenzoate (A) in 48 ml. methylene chloride was cooled to 0° C. and treated with 2.02 ml. triethylamine followed by 1.35 ml. butyl chloroformate. The resultant solution was stirred at 0° C. for 15 minutes and then at room temperature for 24 hours. A precipitate was removed by filtration. The filtrate was evaporated and the residue was purified by flash chromatography on a 6×25 cm. silica gel column using 35% v/v ethyl acetate in hexane as the eluent. There was thus obtained 1.96 g. (45%) of methyl 4-[6-(N-butoxycarbonyl)aminoindol-1-ylmethyl]-3-methoxybenzoate as an ivory coloured solid; NMR: 0.9 (t, 3H, CH$_2$CH$_3$), 1.5 (m, 4H, CH$_3$CH$_2$CH$_2$), 3.9 (s, 3H, OCH$_3$), 4.0 (s, 3H, OCH$_3$), 4.2 (t, 2H, OCH$_2$), 6.5 (dd, 1H, H$^3$-indole), 6.7 (m, 2H), 6.9 (dd, 1H, H$^5$-indole), 7.1 (d, 1H, H$^2$-indole), 7.5 (m, 4H).

EXAMPLE 23

To a stirred slurry of 24 mg. sodium hydride (hexane washed) in 1 ml. dry dimethylformamide (DMF) was added a solution of 230 mg. 6-hexanamidoindole (E) in 8 ml. DMF. The dark mixture was stirred for 30 minutes, then treated with a solution of 275 mg. methyl 4-bromomethylbenzoate (F) in 1 ml. DMF, and stirred overnight. The reaction was quenched by addition of saturated aqueous ammonium chloride, poured into water, and extracted with ethyl acetate. The combined extracts were washed with water, dried (MgSO$_4$) and evaporated to give 300 mg. (79%) of methyl 4-(6-hexanamidoindol-1-ylmethol)benzoate as a dark oil; NMR: 0.9 (m, 3H, CH$_2$CH$_3$), 1.4 (m, 4H, CH$_3$CH$_2$CH$_2$), 1.7 (m, 2H, CO.CH$_2$CH$_2$), 2.3 (t, 2H, CO.CH$_2$), 3.9 (s, 3H, OCH$_3$), 5.3 (s, 2H, NCH$_2$) 6.5 (d, 1H, H$^3$-indole), 6.9 (dd, 1H, H$^5$-indole), 7.0–8.0 (m, 8H).

The starting material (E) was obtained as follows:

(a) A yellow solution of 5.2 g. 6-nitroindole in 150 ml. ethyl acetate was added to 1.25 g. of pre-induced 10% w/w palladium-on-charcoal in 50 ml. ethyl acetate. The mixture was shaken under 3.45 bar hydrogen overnight and then filtered through diatomaceous earth. The residue was washed with 150 ml. hot chloroform and the combined colourless filtrate and washings were evaporated to give a quantitative yield of 6-aminoindole as a dark oil; NMR: 3.5 (br s, 2H, NH$_2$), 6.4 (m, 1H, H$^3$). 6.5 (m, 2H, H$^5$+H$^7$), 7.0 (dd, 1H, H$^2$, 7.4 (d, 1H, H$^4$), 7.8 (br, 1H, NH).

(b) A solution of 4.24 g. 6-aminoindole in 300 ml. methylene chloride was stirred at 0° C. and 5.4 ml triethylamine followed by 4.2 ml. hexanoyl chloride was then added. The dark mixture was stirred for 1 hour and then filtered to remove a white precipitate. The filtrate was diluted with methylene chloride; washed sequentially with 10% w/v sodium hydrogen sulphate water, and brine; dried (MgSO$_4$); and evaporated. The residue was crystallized from ethyl acetate and hexane to give 6-hexanamidoindole (E) as a white solid. Partial evaporation of the mother liquor gave a second crop of solid giving a combined yield of 4.5 g. (65%); NMR: 0.9 (t, 3H, CH$_3$), 1.4 (m, 4H, CH$_3$CH$_2$CH$_2$), 1.8 (m, 2H, CO.CH$_2$CH$_2$), 2.4 (t, 2H, CO.CH$_2$), 6.5 (m, 1H, H$^3$), 6.8 (dd, 1H, H$^5$), 7.2 (m, 2H, CO.NH+H$^2$), 7.5 (d, 1H, H$^4$), 8.1 (bs, 1H, H$^7$), 8.3 (br, 1H, NH).

The starting bromo ester (F) was prepared as follows:

(c) To 200 ml. of methanol at 0° C. was added, with stirring, 48.4 g. of 4-methylbenzoyl chloride over 20 minutes. Following the addition, the reaction mixture was stirred at room temperature for one hour. The methanol was evaporated and the residue was distilled to give 43 g. methyl 4-methylbenzoate as a colourless liquid, boiling point 103°–108° C. at 20 mm. of Hg.

(d) Bromination of methyl 4-methylbenzoate using the procedure described in part (d) of Example 1 gave a 97% yield of methyl 4-bromomethylbenzoate (F) as an oil, b.p. 88°–95° C. at 0.16 mm. Hg., which crystallized after distillation.

EXAMPLE 24

Using a similar procedure to that described in Example 23, but replacing the bromo ester (F) by methyl 5-chloromethylfuran-2-carboxylate, there was obtained methyl 5-(6-hexanamidoindol-1-ylmethyl)furan-2-carboxylate in 34% yield as a white solid; partial NMR:3.9 (s, 3H, OCH$_3$), 5.3 (s, 2H, NCH$_2$), 6.2 (d, 1H, H$^4$-furan).

EXAMPLE 25

Starting from 2,3,5-trimethyl-6-nitroindole (G) and using methods analogous to those in Example 1, methyl 4-(6-hexanamido-2,3,5-trimethylindol-1-ylmethyl)-3-methoxybenzoate was obtained in 40% yield as a slightly green solid; NMR: 0.9 (m, 3H, $CH_2CH_3$), 1.3 (m, 4H, $CH_3CH_2CH_2$), 1.7 (m, 2H, $CO.CH_2CH_2$), 2.2–2.4 (11H, $3CH_3 + CO.CH_2$), 3.9 (s, 3H, $OCH_3$), 4.0 (s, 3H, $OCH_3$), 5.3 (s, 2H, $NCH_2$), 6.3 (d, 1H, m-MeO-$C_6H_3$), 6.9 (br, 1H, NH), 7.3–7.6 (3H, aromatic H), 7.7 (br s, 1H, $H^7$-indole).

The starting indole G was obtained as follows:

(a) A vigorously stirred slurry of 4.0 g. pulverized 4-methyl-3-nitroaniline in 8.4 ml. concentrated hydrochloric acid and 30 ml. water was cooled to 0° C. and treated dropwise with a solution of 2.4 g. sodium nitrite in 4 ml. water at such a rate that the temperature of the reaction mixture remained below 5° C. A small quantity of insoluble material was removed by rapid filtration. The clear yellow filtrate was added rapidly to a vigorously stirred solution of 9.0 g. sodium sulphite and 0.8 g. sodium hydroxide in 30 ml. water at 0° C. The resulting dark mixture was stirred at room temperature for 1 hour and then treated with concentrated hydrochloric acid until the colour lightened and a precipitate appeared. The mixture was then warmed to 40° C., acidified to pH 1, and allowed to stand at room temperature overnight. The orange precipitate was collected by filtration and dissolved in 50 ml. of hot water to give a dark red solution which was filtered hot and diluted to 100 ml. with concentrated hydrochloric acid. Upon cooling 2.12 g. of 4-methyl-3-nitrophenylhydrazine hydrochloride (H) contaminated with some sodium chloride was collected by filtration as a light brown solid and was used directly.

(b) To a mixture of 4.0 g. of H and 60 ml. anhydrous ethanol stirred at 60° C. was added 2 ml. of methyl ethyl ketone. The resulting red solution was heated under reflux for 2 hours. A small quantity of white solid was removed by filtration of the hot solution. The filtrate was evaporated. The gummy orange residue of the hydrazone was mixed with 50 ml. acetic acid and 3.3 ml. boron trifluoride etherate. The mixture was heated under reflux for 2 hours and solid removed by hot filtration. The dark green filtrate was evaporated to a green oil which was dissolved in ethyl acetate. The solution was washed with 10% w/v sodium carbonate and then purified by flash chromatography on a 6×20 cm. column of silica gel using 30% v/v ethyl acetate in hexane. Evaporation of the early fractions gave 0.64 g. (16%) of 2,3,5-trimethyl-6-nitroindole (G) as an orange solid; NMR: 2.3 (s, 3H, $CH_3$) 2.5 (s, 3H, $CH_3$) 2.7 (s, 3H, $CH_3$), 7.3 (s, 1H, $H^4$), 8.0 (br, 1H, NH), 8.1 (s, 1H, $H^7$). Later fractions yielded 0.43 g. of 2,3,5-trimethyl-4-nitroindole as an orange solid: NMR 2.1 (s, 3H, $CH_3$), 2.4 (2s, 6H, $2CH_3$), 6.9 (d, 1H), 7.3 (d, 1H) and 7.9 (br, 1H, NH).

EXAMPLE 26-32

Using a similar procedure to that described in Example 1, the following esters of formula 3 were obtained starting from the appropriate 4- or 6-aminoindole derivatives of formula 4, the latter derivatives being obtained from known nitro-indoles using the procedures described in preceding Examples:

| Ex | R,Ra | Re | * | Yield (%) | Partial NMR |
|---|---|---|---|---|---|
| 26 | $CH_3$ | pentyl | 6 | 68 | 2.2(s, 3H, $CH_3$), 2.3 (s, 3H, $CH_3$) |
| 27 | $(CH)_4$ | cyclopentyloxy | 6 | 90 | 1.55–1.86[br m, 8H, $(CH_2)_4$], 5.15(m, 1H, CHO) |
| 28 | $(CH_2)_4$ | pentyl | 6 | 99 | 1.9(m, 4H), 2.5–2.7 (m, 4H) |
| 29 | $CH_3$ | pentyl | 4 | 72 | 2.2(s, 3H, $CH_3$), 2.5 (s, 3H, $CH_3$) |
| 30 | $(CH)_4$ | cyclopentylmethyl | 6 | 78 | 2.35(br s, 3H, $CHCH_2$) |
| 31 | $(CH_2)_4$ | pentyl | 4 | 99 | 1.9(m, 4H), 2.5–2.7 (m, 4H) |
| 32 | $(CH)_4$ | pentyl | 4 | 31 | 6.4–8.2(11H, Ar + NH) |

*Position of amide attachment to indole nucleus

EXAMPLE 33

Using the same procedure as described in Example 1 but starting from methyl 4-(6-aminoindazol-1-ylmethyl)benzoate [obtained by catalytic reduction of methyl 4-(6-nitroindazol-1-ylmethyl)benzoate (J)], methyl 4-(6-hexanamidoindazol-1-ylmethyl)benzoate was obtained as a white solid m.p. 122.5°–123° C.

The starting nitro ester (J) was obtained as follows:

A mixture of 3.7 g. sodium 6-nitrotindazolide, 4.58 g. of methyl 4-bromomethylbenzoate (F) and 120 ml. acetone was heated under reflux in a nitrogen atmosphere for 54 hours and then diluted with 250 ml. ethyl acetate and 40 ml. of 50% w/v brine. The organic layer was separated, washed with brine, dried ($MgSO_4$), and evaporated to give a brown solid. Early fractions from chromatography of the solid on a Waters 500 HPLC ($SiO_2$, 25% v/v ethyl acetate in hexane) yielded a solid which was crystallized from ethyl acetate to give methyl 4-(6-nitroindazol-1-yl)methylbenzoate (J) as light yellow needles, 1.71 g. (28%); m.p. 171°–172° C.; partial $^{13}C$-NMR: 134.10 (C-3).

EXAMPLE 34

A mixture of 0.505 g. methyl 4-(6-hexanamido-2,3,-dimethylindol-1-ylmethyl)-3-methoxybenzoate, 0.29 g. lithium hydroxide hydrate, 7 ml. tetrahydrofuran, 2 ml. methanol, and 2 ml. water was stirred overnight. The mixture was then evaporated. The white solid obtained was dissolved in 40 ml. water. Acidification of this homogeneous alkaline solution by dropwise addition of 10% v/v hydrochloric acid gave a fine white precipitate which was collected by filtration and recrystallized from ethyl acetate/hexane. There was thus obtained 0.33 g. (68%) of 4-(6-hexanamido-2,3-dimethylindol-1-ylmethyl)-3-methoxybenzoic acid as a white powder; m.p. 220°–222° (d) °C.; microanalysis, found: C, 71.07; H, 7.14; N, 6.38%; $C_{25}H_{30}N_2O_4$ requires: C, 71.07; H, 71.16; N, 6.63%.

EXAMPLES 35-66

Using the same general procedure as described in Example 34, the following acids of formula 5 may be obtained by hydrolysis of the corresponding methyl esters of formula 1:

| Example | Re | mp. (°C.) | Yield (%) |
|---|---|---|---|
| 35 | pentyl | 221–223 (d) | 39 |
| 36 | propyl | 225–228 | 24 |

-continued

| Example | Re | mp. (°C.) | Yield (%) |
|---|---|---|---|
| 37 | heptyl | 200–201 | 40 |
| 38 | nonyl | 194–196 | 74 |
| 39 | 1,3-pentadienyl | 238–240 (d) | 27 |
| 40 | benzyl | 249–250 | 29 |
| 41 | 2-phenylethyl | 225–227 | 62 |
| 42 | 3-phenylpropyl | 186–188 | 49 |
| 43 | 1-phenylpropyl | 215–216 | 52 |
| 44 | 3-butyn-1-yl | 230–231 | 34 |
| 45 | 4-chlorobenzyl | >255 | 45 |
| 46 | 4-CF$_3$-benzyl | >250 | 49 |
| 47 | benzhydryl | 262–263 | 39 |
| 48 | 2-thienylmethyl | 244–245 | 62 |

Similarly, 4-(6-hexanamidoindolin-1-ylmethyl)-3-methoxybenzoic acid (Example 49) was obtained as a solid, m.p. 145°–148° (d) °C. in 39% yield starting from the corresponding methyl ester (Example 15).

Similarly, the following acids of formula 6 were obtained from the appropriate methyl ester starting materials:

| Example | Re | X | Xa | m.p. (°C.) | Yield (%) |
|---|---|---|---|---|---|
| 50 | butyl | NH | O | 193–194 | 76 |
| 51 | t-butyl | NH | O | 181–182 | 30 |
| 52 | hexyl | NH | O | 204–205 | 73 |
| 53 | benzyl | NH | O | 204–205 (d) | 5 |
| 54 | butyl | NH | S | 200–201 | 62 |
| 55 | cyclopentyl | direct link | O | 271–272+ (d) | 26 |
| 56 | butyl | O | O | 174–175 | 21 |

+ partial hydrate.

Similarly, the following acids of formula 7 may be obtained:

| Example | G$^1$—Q—CO$_2$H | A | m.p. (°C.) | Yield (%) |
|---|---|---|---|---|
| 57 | 4-carboxybenzyl | CH | 194–195 | 26 |
| 58 | 5-carboxyfur-2-ylmethyl | CH | 200–202 | *80 |
| 59 | 4-carboxybenzyl | N | 215–215.5 | *81 |

Similarly, the following acids of formula 8 may be obtained (Exs. 60, 62, 63, 65, 66: Re=pentyl; Ex 61: Re=cylclopentyl.0; Ex 64: Re=cyclopentyl.CH$_2$):

| Example | R,Ra | Amide Position | Rc | m.p. (°C.) | Yield (%) |
|---|---|---|---|---|---|
| 60 | methyl | 6 | 5-methyl | 278–280 (d) | **46 |
| 61 | (CH)$_4$ | 6 | H | 254–255+ | 54 |
| 62 | (CH$_2$)$_4$ | 6 | H | 194–195 (d) | 14 |
| 63 | methyl | 4 | H | 190 (d) | 51 |
| 64 | (CH)$_4$ | 6 | H | 288–289+ | 65 |
| 65 | (CH$_2$)$_4$ | 4 | H | 222–223 (d) | 51 |
| 66 | (CH)$_4$ | 4 | H | >245 | 37 |

Notes:
**recrystallised from aqueous ethanol.
+partial hydrate.

EXAMPLE 67

A mixture of 189 mg. 6-hexanamido-1-(4-cyano-2-methoxybenzyl)indole, 99 mg. sodium azide, 105 mg. triethylamine hydrochloride, and 3.7 ml. N-methylpyrrolidone was stirred at 150° C. under nitrogen for 3.5 hours. After cooling, the reaction mixture was diluted with 20 ml. water, acidified to pH 1 with 10% v/v hydrochloric acid and extracted with ethyl acetate. The organic layer was extracted with 10% w/v sodium hydroxide. The alkaline extract was washed with ether and then acidified. Ethyl acetate extraction of this acidified aqueous layer gave, upon evaporation, a solid which was recrystallized from aqueous methanol to yield 90 mg. (43%) of 6-hexanamido-1-(2-methoxy-4-[1(H)-tetrazol-5-yl]benzyl)indole m.p. 210°–212° C.; microanalysis, found: C, 65.62; H, 6.15; N, 20.08%; C$_{23}$H$_{26}$N$_6$O$_2$ requires: C, 66.01; H, 6.26; N, 20.28%.

The starting amido nitrile was prepared as follows:

(a) To a stirred suspension of 9.97 g. 3-methoxy-4-methylbenzoic acid in 18 ml. methylene chloride heated to reflux under nitrogen, was added dropwise over 45 minutes a solution of 5.35 ml. chlorosulphonylisocyanate (1.025 equivalents) in 3 ml. methylene chloride. The resulting homogeneous, bright red solution was heated under reflux for 45 minutes, chilled in an ice bath, and treated dropwise with 9.5 ml. dimethylformamide over 15 minutes. After stirring for 30 minutes at 0° C., the orange solution was poured onto ice. The organic layer was separated, washed five times with 20 ml. water, dried (MgSO$_4$) and evaporated. The residue was chromatographed on a Waters 500 HPLC (SiO$_2$, 10% (v/v) hexane in toluene) to give 5.28 g. (60%) of 3-methoxy-4-methylbenzonitrile as a white solid, m.p. 51–52.5° C.

b) A solution of 2.65 g. 3-methoxy-4-methylbenzonitrile in 90 ml. dry carbon tetrachloride was treated with 3.20 g. N-bromosuccinimide and 5 mg. benzoyl peroxide. The mixture was then heated to reflux for 15 minutes with a 250 watt tungsten lamp. The cooled reaction mixture was diluted with 90 ml. petroleum ether (b.p.60°–80° C.) insoluble material removed by filtration and the filtrate evaporated. The solid residue was recrystallized from methylene chloride-petroleum ether to give 2.64 g. (65%) of 4-bromomethyl-3-methoxybenzonitrile as a white solid, m.p. 87°–91° C.

(c) Using the same procedure as described in Example 23 but starting from 4-bromomethyl-3-methoxybenzonitrile in place of methyl 4-bromomethylbenzoate, there was obtained 6-hexanamido-1-(4-cyano-2-methoxy-benzyl)indole m.p. 136°–138° C. in 68% yield.

EXAMPLE 68

Using the same procedure as described in Example 67 but starting from 1-(4-cyanophenylmethyl)-6-hexanamidoindole, there was obtained 6-hexanamido-1-(4-[1(H)-tetrazol-5yl]benzyl)indole in 50% yield as a hemihydrate, m.p. 134°–136° C. The starting material was made using an analogous procedure to that described in Example 23, but using 4-bromomethylbenzonitrile in place of methyl 4-bromomethylbenzoate, and was obtained in 59% yield as a solid, m.p. 106°–109° C.

EXAMPLES 69–72

Using a similar procedure to that described in Example 67, the following tetrazoles of formula 9 were obtained from the correspoding nitriles of formula 10:

| | | Tetrazole 9 | | Nitrile 10 | |
|---|---|---|---|---|---|
| Example | G$^1$ | m.p. (°C.) | yield (%) | m.p. (°C.) | Yield |
| 69 | (CH$_2$)$_3$ | 149–150* | 51 | 96–98 | 30 |
| 70 | (CH$_2$)$_4$ | 114–115 | 43 | ** | 67 |
| 71 | (CH$_2$)$_5$ | 158–161* | 73 | 71–72 | 70 |

-continued

| Example | $G^1$ | Tetrazole 9 m.p. (°C.) | yield (%) | Nitrile 10 m.p. (°C.) | Yield |
|---|---|---|---|---|---|
| 72 | $(CH_2)_6$ | 133-135 | 72 | 86-88 | 55 |

*Partial hydrate
**Partial NMR: 1.6(m, 2H, NCH$_2$C$\underline{H}_2$), 2.0(m, 2H, C$\underline{H}_2$CH$_2$CN), 2.4(t, 2H, CH$_2$CN), 4.2(t, 2H, NCH$_2$).

The above nitriles of formula 10 were obtained using the general procedure of Ex.23 starting from 6-hexanamidoindole and the appropriate bromonitrile of the formula Br.G$^1$.CN.

EXAMPLE 73

A stirred suspension of 19 mg. sodium hydride in 5 ml. dry dimethylformamide was treated at 0° C. under a nitrogen atmosphere with 33 mg. 1(H)-tetrazol-5-thiol. After 10 minutes the mixture was warmed to room temperature and added to 76 mg. 6-hexanamido-1-(3-chloropropyl) (K). After stirring for 25 minutes this mixture was diluted with 30 ml. water, acidified to pH 2 with 1M hydrochloric acid, and then extracted with ethyl acetate. The extracts were dried (MgSO$_4$) and evaporated. The oily residue crystallised from ethyl acetate/hexane. Recrystallisation from aqueous methanol gave 22.8 mg. (25%) of 6-hexanamido-1-(3-[1(H)-tetrazol-5-ylthiol]-propyl)indole as a white solid; m.p. 117°-119° C.; microanalysis, found: C, 57.97; H,6.43; N, 22.22%; $C_{18}H_{24}N_6OS$ requires: C, 58.04; H, 6.49; N,22.56%.

The starting indole derivative (K) was obtained as a white solid [partial NMR: 2.4 (m,2H, NCH$_2$CH$_2$), 3.4 (t,2H, CH$_2$Cl), 4.3 (t,2H,CH$_2$N)] using the same general procedure as described in Example 23, but replacing methyl 4-bromomethylbenzoate with 1-bromo-3-chloropropane.

EXAMPLE 74

A solution of 1.10 g. 2-phenylbutyric acid in 10 ml. methylene chloride was treated with 1.09 g. 1,1'-carbonyldiimidazole in several portions. After the effervescence subsided, the mixture was heated under reflux for 5 minutes and then cooled to room temperature. To this mixture was added a solution of 0.07 g. methyl 4-(6-aminoindazol-1-ylmethyl)-3-methoxybenzoate (L) in 10 ml. methylene chloride followed by 0.027 g. 4-N,N-dimethylaminopyridine. The resulting mixture was stirred for 24 hours and then diluted with 75 ml. ethyl acetate. This organic solution was washed successively with 0.5M hydrochloric acid, saturated sodium carbonate, and brine; dried (MgSO$_4$); and evaporated. The residue was purified by flash chromatography on 30 g. of silica gel using 30% v/v ethyl acetate in petroleum ether (b.p. 60°-80° C.) as the eluent, to give 1.0 g. (97%) methyl 4-[6-(2-phenylbutanamido)indazol-1-ylmethyl]-3-methoxybenzoate, as a light pink solid; m.p. 57°-61° C.

The starting ester (L) was obtained in 92% yield as a solid, m.p. 131.5°-132° C., using an analogous procedure to that described in Example 33, but starting with methyl 4-bromomethyl-3-methoxybenzoate and with intermediate isolation of methyl 4-(6-nitroindazol-1-ylmethyl)-3-methoxybenzoate in 28% yield, as a pale yellow powder, m.p. 137°-137.5° C.

EXAMPLE 75

A solution of 0.70 g. methyl 4-(6-aminoindazol-1-ylmethyl)-3-methoxybenzoate (L) and 0.33 ml. 2,6-lutidine in 10 ml. of methylene chloride was cooled to −20 C. under a nitrogen atmosphere and treated dropwise with 0.30 ml. n-butylchloroformate. The solution obtained was stirred at room temperature for 2 hours and then diluted with 75 ml. of ethyl acetate. This mixture was washed successively with saturated sodium carbonate and brine; dried (MgSO$_4$); and evaporated. The residue was purified by flash chromatography on 25 g. silica gel using 25% v/v ethyl acetate in petroleum ether (b.p. 60°-80° C.) and the solid obtained recrystallized from 50% v/v ether/petroleum ether (b.p. 40°-60° C.) to give 0.79 g. (85%) of methyl 4-[6-(butoxycarbonyl)aminoindazol-1-ylmethyl]-3-methoxybenzoate as a white solid, m.p. 112°-112.5° C.; microanalysis, found: C, 64.16; H, 6.17; N, 9.85%; $C_{22}H_{25}N_3O_5$ requires: C, 64.22; H, 6.12; N, 10.2%.

EXAMPLES 76-77

Using a similar procedure to that described in Ex. 34, the following compounds were made starting from the corresponding methyl esters:

EXAMPLE 76

4-[6-(2-phenylbutanamido)indazol-1-ylmethyl]-3-methoxybenzoic acid as a white solid; in 76% yield, m.p. 244-245 (d) °C.; microanalysis, found: C, 70.18; H, 5.56; N, 9.25%; $C_{26}H_{25}N_3O_4$ requires: C, 70.40; H, 5.68; N, 9.47%.

EXAMPLE 77

4-[6-(butoxycarbonyl)aminoindazol-1-ylmethyl]-3-methoxybenzoic acid as a white solid in 88% yield; m.p. 213.5-214 (d) °C.; microanalysis, found: C, 63.11; H, 6.17; N, 10.31%; $C_{21}H_{23}N_3O_5$ requires: C, 63.45; H, 5.83; N, 10.57%.

EXAMPLES 78-83

Using a similar procedure to that described in Example 9 but starting from the appropriate carboxylic acid of the formula Re.CO$_2$H, the following esters of formula 1 were obtained:

| Example | Re | Yield (%) | Partial NMR |
|---|---|---|---|
| 78 | 1-Ph-ethyl* | 46 | 1.6(d, 3H, CH$_3$), 3.6(t, 1H, PhC$\underline{H}$), 7.3(s, 5H, Ph) |
| 79 | 1-Ph-pentyl | 55 | 0.9(t, 3H, CH$_3$), 3.4(t, 1H, PhC$\underline{H}$), 7.3(s, 5H, Ph) |
| 80 | 3-heptyl | 36 | 0.9(t, 6H, 2CH$_3$), 1.5(m, 9H) |
| 81 | cyclopentylmethyl | 22 | 1.6(m, 9H), 2.3(s, 2H, CH$_2$) |
| 82 | 4-methylbenzyl | 72 | 2.4(s, 3H, CH$_3$), 3.6(s, 2H, PhC$\underline{H}_2$) |

*Ph = phenyl

Similarly, starting from methyl 4-(6-amino-2,3,5-trimethylindol-1-ylmethyl)-3-methoxybenzoate (itself obtained using the procedures described for A in Example 1 but starting from 2,3,5-trimethyl-6-nitroindole [G]) and 2-phenylbutyric acid, there was obtained methyl 3-methoxy-4-[2,3,5-trimethyl-6-(2-phenylbutanamido)indol-1-ylmethyl]-benzoate [Example 83] in 32% yield as a white solid; partial NMR: 0.9 (t,3H,CH$_2$CH$_3$), 1.2 (m,2H, CH$_2$CH$_3$), 3.4 (t,1H,CHPh), 7.3 (s,5H,Ph).

EXAMPLES 84–85

Using a similar procedure to that described in Example 16 but starting with the appropriate isocyanate there were obtained:

(Example 84) methyl 4-(6-N'-cyclohexylureidoindol-1-ylmethyl)-3-methoxybenzoate in 51% yield as a solid; partial NMR: 1.4 (br m, 10H), 4.5 (br d, 1H);

(Example 85): methyl 3-methoxy-4-(6-N'-o-trifluoromethylphenylureidoindol-1-ylmethyl)benzoate in 63% yield as a solid; partial NMR: 6.3–7.5 (aromatic H).

EXAMPLE 86–89

Using an analogous procedure to that described in Example 22 but starting with the appropriate chloroformate of the formula ReO.CO.Cl, the following esters of formula 11 were obtained:

| Example | Re | Yield (%) | Partial NMR |
|---|---|---|---|
| 86 | hexyl | 99 | 1.9(t, 3H, $CH_3$), 1.3(m, 6H), 1.7(m, 2H), 4.1(t, 2H, $OCH_2$) |
| 87 | l-menthol+ | 76 | 0.8(d, 3H, $CH_3$), 0.9(d, 6H, $CH_3$), 4.6(m, 1H, OCH) |
| 88 | benzyl | 99 | 5.2(s, 2H, $CH_2Ph$) 7.3(2, 5H, Ph) |

(+derived from l-menthol)

Similarly, starting from methyl 4-(6-amino-2,3,5-trimethylindol-1-ylmethyl)-3-methoxybenzoate and butyl chloroformate, methyl 4-[6-(butoxycarbonyl)-amino-2,3,5-trimethylindol-1-ylmethyl]-3-methoxybenzoate (Example 39) was obtained in 99% yield as a white solid; partial NMR: 0.9 (t, 3H, $CH_2CH_3$), 1.3 (m,2H,$CH_2CH_3$), 1.5 (m,2H, $CH_2OCH_2$), 4.1 (t,2H,$CH_2O$), 4.1 (t,2H,$CH_2O$).

EXAMPLE 90

A solution of 0.80 g. methyl 4-(6-aminoindol-1-ylmethyl)-3-methoxybenzoate (A) in 13 ml. anhydrous dioxane was treated with a solution of 0.31 ml; trichloromethyl chloroformate in 13 ml. dioxane. The reaction vessel was continuously purged with nitrogen and the effluent bubbled through aqueous potassium hydroxide to destroy any liberated phosgene. The in situ formation of the isocyanate of A was followed by TLC. After 30 minutes 0.75 ml. cyclopentanol and a catalytic amount of triethylamine were added to the reaction solution which was then heated to 80° C. for 2.5 hours and subsequently evaporated. The resultant residue was purified by flash chromatography on a 6×25 cm. silica gel column using 7% v/v ethyl acetate in toluene as the eluent to give 0.92 g. (84%) of methyl 4-[6-(cyclopentyloxycarbonyl)aminoindol-1-ylmethyl]-3-methoxybenzoate as a white solid; NMR: 1.7 (m,8H, $(CH_2)_4$), 3.9 (s,3H,$OCH_3$), 4.0 (s,3H,$OCH_3$), 5.2 (br,1H,CHO), 5.3 (s, 2H,$NCH_2$), 6.5 (dd, 1H,$H^3$-indole), 6.6 (br,d, 2H, aromatic+NH), 6.8 (dd, 1H, $H^5$-indole), 7.1 (d,1H,$H^2$-indole), 7.2 (d,1 aromatic H), 7.4–7.5 (m,3 aromatic H), 7.6 (br s, 1H, $H^7$-indole).

EXAMPLES 91–95

Using an analogous procedure to that described in Example 90 but starting with the appropriate alcohol, the following esters of formula 11 were obtained:

| Example | Re | Yield (%) | Partial NMR |
|---|---|---|---|
| 91 | 3-pentyl | 65 | 0.9(t, 6H, $2CH_3$), 1.5(m, 4H, $2CH_2$), 4.6(m, 1H, CHO). |
| 92 | cyclobutyl | 57 | 0.9[br m, 6H, $(CH_2)_3$], 5.0(t, 1H, CHO). |
| 93 | 1-phenylpropyl | 31 | 0.9(t, 3H, $CH_3$), 1.8(m, 2H, $CH_2$), 5.6(t, 1H, CHO), 7.3(s, 5H, Ph) |
| 94 | t-butyl | 21 | 1.4[s, 9H, $C(CH_3)_3$] |
| 95 | cyclohexyl | 69 | 1.1–1.8[br m, 10H, $(CH_3)_5$], 4.6(br, 1H, CHO) |

EXAMPLE 96

Using a similar procedure to that described in Example 90 but using cyclopentylamine instead of cyclopentanol, methyl 4-(6-N'-cyclopentylureidoindol-1-ylmethyl)-3-methoxybenzoate was obtained in 54% yield as a pale yellow solid; partial NMR: 1.2–2.0 [br m, 8H,$(CH_2)_4$], 4.4 (m,1H,CHNH), 4.9 (d,1H,CHNH).

EXAMPLE 97

Using a similar procedure to that described in EX.22, but starting from methyl 5-(6-aminoindol-1-ylmethyl)-furan-2-carboxylate and cyclopentyl chloroformate, there was obtained methyl 5-[6-(cyclopentyloxycarbonyl)aminoindol-1-ylmethyl]furan-2-carboxylate in 53% yield, as an off-white solid; partial NMR: 1.5–200 [br m, 8H, $(CH_2)_4$], 6.2 (d, 1H, CH.CH=C), 6.6 (br.s, 1H,NH).

The starting amino-indole was obtained as a solid in 99% yield with partial NMR: 3.5 (s,2H,$NH_2$), 3.9 (s,3H,$OCH_3$), 5.2 (s,2H,$NCH_2$), using a procedure similar to that described in parts (a) and (b) of Ex.1 but starting from methyl 5-chloromethylfuran-2-carboxylate.

EXAMPLE 98

Using a similar procedure to that described in Example 23 but replacing the bromo ester (F) by methyl 7-bromoheptanoate, there was obtained methyl 7-(6-hexanamidoindol-1-ylmethyl)heptanoate in 35% yield as a solid, m.p. 61°–63° C.

EXAMPLE 99

Using a similar procedure to that described in Example 23 but using 6-(2-ethylhexanamido)indole (M) in place of 6-hexanamidoindole (E), there was obtained methyl 4-[6-(2-ethylexanamido)indol-1-ylmethyl]-benzoate as a white solid in 32% yield, m.p. 139°–141° C.

The starting indole M was obtained in an analogous manner to that described for 6-hexanamidoindole (E) in part (b) of Example 23 but using 2-ethylhexanoyl chloride in place of hexanoyl chloride, and was obtained as a light brown powder in 56% yield, m.p. 154°–156° C.

EXAMPLES 100–104

Using a similar procedure to that described in Example 99 the following esters of the formula 12 (wherein $R^1$=methyl) were obtained using the appropriate benzyl bromide derivative of the formula 13:

| Example | Rd | $G^2$ (and location on Q) | Yield (%) | m.p. (°C.) |
|---|---|---|---|---|
| 100 | H | direct link (3) | 39 | 125–126 |
| 101 | 2-F | direct link (4) | 40 | 155–157 |
| 102 | 2-OCH$_3$ | vinyl (5) | 42 | 150–152 |
| 103 | 3-Br | direct link (4) | 33 | * |
| 104 | 2-O.butyl | direct link (4) | 63 | ** |

Notes:
*non-crystalline; partial NMR: 6.9 (d, 1 aromatic H),
**non-crystalline; microanalysis, found: C, 73.00; H, 8.04; N, 5.60%; C$_{29}$H$_{38}$N$_2$O$_4$ requires: C, 72.77; H 8.00; N, 5.85%.

Methyl 4-bromomethyl-3-butoxybenzoate (required for Example 104) may be obtained as an oil in 66% yield [partial NMR: 3.94 (s,3H, CO$_2$CH$_3$), 4.10 (m,2H,CH$_2$O), 4.58 (s,2H,CH$_2$Br)] by brominatin of methyl 3-butoxy-4-methylbenzoate (N) using the general procedure described for B in Example 1(d) but with purification by flash chromatography on silica gel using 2% v/v ethyl acetate in petroleum ether (b.p. 60°–80° C.).

The starting ester N was itself obtained as a pale yellow oil in 92% yield [partial NMR: 2.26 (s,3H, CH$_3$.C), 3.90 (s,3H, CO$_2$CH$_3$), 4.03 (m,2H, CH$_2$O)] by alkylation of methyl 3-hydroxy-4-methylbenzoate (O) using butyl bromide and potassium carbonate in refluxing acetone. The ester O was obtained in 73% yield as a solid, m.p. 112°–114° C. [recrystallised from ether/petroleum ether (b.p. 40°–60° C.)] by a conventional acid catalysed esterification of 3-hydroxy-4-methylbenzoic acid.

EXAMPLES 105–110

Using a similar procedure to that described in Example 1 the following esters of the formula 14 were obtained by acylation of the appropriate 6-aminoindole ester of the formula 4 using the appropriate acid chloride of the formula Re.X.CO.Cl, the required starting esters of formula 4 being obtained from known 6-nitroindoles using analogous procedures to those described in preceding Examples:

| Ex. | R | Ra | Re | X | Yield (%) | Partial NMR |
|---|---|---|---|---|---|---|
| 105 | (CH$_2$)$_2$.CH(et)CH$_2$ | | pentyl | direct link | 99 | 1.0(t, 3, CH$_2$CH$_3$) |
| 106 | (CH)$_2$.C(Et).CH | | pentyl | direct link | 40 | 2.8(q, 2H, C.CH$_2$CH$_3$) |
| 107+ | CH$_3$ | CH$_3$ | Ph.CH(Et) | direct link | 49 | 0.9(t, 3H, CH$_2$CH$_3$), 2.0(m, 2H, CH$_2$CH$_3$) |
| 108 | CH$_3$ | CH$_3$ | butyl | O | 70 | 0.9(t, 3H, CH$_2$CH$_3$), 4.1(t, 2H, OCH$_2$) |
| 109 | CH$_3$ | H | butyl | O | 44 | 2.3(s, 3H, CH$_3$), 6.3(s, 1H, H$^3$-indole). |

Note:
(i) In Example 105, 106 the CH$_2$ or CH adjacent to "C(Et)" is attached at C$^3$ of the indole i.e. to Ra;
(ii) Ph = phenyl, Et = ethyl.
(iii) +prepared from 2-phenylbutyric acid using the modified acylation procedure of Example 9.

Similarly starting from methyl 4-(4-aminoindol-1-ylmethyl)-3-methoxybenzoate and hexanoyl chloride there was obtained methyl 4-(4-hexanamidoindol-1-ylmethyl)-3-methoxybenzoate (Example 110) in 74% yield as a non-crystalline solid, partial NMR: 7.0 (t,1H, H$^6$-indole), 7.1 (d,1H,H$^5$-indole), 7.6 (d,1H, H$^7$-indole).

EXAMPLES 111–145

Using the same general procedure as described in Example 34, the following acids of formula 5 may be obtained by hydrolysis of their corresponding methyl esters:

| Example | Re | m.p. (°C.) | Yield (%) |
|---|---|---|---|
| 111 | 1-phenylethyl | 209–210* | 38 |
| 112 | 1-phenylpentyl | 230–231 | 62 |
| 113 | 3-heptyl | 230–231* | 68 |
| 114 | cyclopentylmethyl | 259–260 | 35 |
| 115 | 4-methylbenzyl | 254–255 | 54 |

*Isolated as a partial hydrate.

Similarly, the following acids of the formula 6 (Xa=oxygen) were obtained by hydrolysis of their corresponding methyl esters:

| Example | Re | X | m.p. (°C.) | Yield (%) |
|---|---|---|---|---|
| 116 | cyclohexyl | NH | 252–254 (d) | 41 |
| 117 | 2-CF$_3$-phenyl | NH | 223–225 (0.5 H$_2$O) | 6 |
| 118 | hexyl | O | 172–174 | 36 |
| 119 | 1-menthyl | O | 205–206 | 55 |
| 120 | benzyl | O | 176–178 | 13 |
| 121 | 3-pentyl | O | 232–233 | 20 |
| 122 | cyclobutyl | O | 238–239 | 67 |
| 123 | 1-phenylpropyl | O | 197–198 | 36 |
| 124 | t-butyl | O | 200–201 | 48 |
| 125 | cyclohexyl | O | 242–243 | 49 |
| 126 | cyclopentyl | NH | 247–248 (d) | 42 |

Similarly, the following acids of the formula 12 (R$^1$-hydrogen) were obtained by hydrolysis of their corresponding methyl esters:

| Ex. | Rd | $G^2$ (and location on Q) | Yield | m.p. (°C.) |
|---|---|---|---|---|
| 127 | H | direct link (4) | 91 | 208–210 |
| 128 | H | direct link (3) | 98 | 216–218 |
| 129 | 2-F | direct link (4) | 96 | 215–216.5 |
| 130 | 2-OCH$_3$ | vinyl (5) | 75 | 202–205 |
| 131 | 3-Br | direct link (4) | 43 | 186–187 |
| 132 | 2-O(CH$_2$)$_3$CH$_3$ | direct link (4) | 70 | 197–199 |

Similarly, the following acids of the formula 15 were obtained by hydrolysis of their corresponding methyl esters:

| Ex. | R | Ra | Re | X | Rc | m.p. (°C.) | yield (%) |
|---|---|---|---|---|---|---|---|
| 133 | CH$_3$ | CH$_3$ | Ph.CH(Et) | — | H | 242–243 (d) | 36 |
| 134 | CH$_3$ | CH$_3$ | Ph.CH(Et) | — | CH$_3$ | 280–281+ (d) | 6 |
| 135 | CH$_3$ | CH$_3$ | butyl | O | H | 188–189 | 36 |
| 136 | CH$_3$ | CH$_3$ | butyl | O | CH$_3$ | 225–226 | 29 |
| 137 | CH$_3$ | H | butyl | O | H | 145–146 | 46 |
| 138 | H | Cl | butyl | O | H | 207–208 | 61 |
| 139 | H | COCH$_3$ | 1-Et-pentyl | — | H | 248–249 | 50 |
| 140 | H | CH$_3$ | 1-Et-pentyl | — | H | 267–268 | 47 |

-continued

| Ex. | R | Ra | Rc | X | Rc | m.p. (°C.) | yield (%) |
|-----|---|----|----|---|----|-----------|----------|
|     |   |    |    |   |    | (d)       |          |

Notes:
(i) X is a direct link for Exs. 133, 134, 139, 140
(ii)+ isolated as a partial hydrate
(iii) Ph = phenyl, Et = ethyl Similarly, the following acids of formula I were obtained by hydrolysis of their corresponding methyl esters:

(Example 141): 4-(6-ethyl-2-hexanamidocarbazol-9-ylmethyl)-3-methoxybenzoic acid, in 38% yield as a solid, m.p. 241°-242° C.;

(Example 142): 4-(3-ethyl-7-hexanamido-1,2,3,4-tetrahydrocarbazol-9-ylmethyl)-3-methoxybenzoic acid, in 29% yield as a solid monohydrate, m.p. 185°-186° C.;

(Example 143): 4-(4-hexanamidoindol-1-ylmethyl)-3-methoxybenzoic acid, in 78% yield as a solid, m.p. 204°-205° C.

(Example 144): 6-(6-hexanamidoindol-1-yl)hexanoic acid, in 56% yield as a solid, m.p. 86°-89° C.; and (Example 145): 5-[6-(cyclopentyloxycarbonyl)aminoindol-1-ylmethyl]-furan-2-carboxylic acid in 60% yield as a solid, m.p. 208°-209° C.

EXAMPLES 146-149

Using a similar procedure to that described in Example 67 but starting from the appropriate nitrile, the following tetrazole derivatives were obtained:

(Example 146): 6-hexanamido-1-(7-[1(H)-tetrazol-5-yl]heptyl)indole in 15% yield as a solid, m.p. 134°-135° C., starting from 6-hexanamido-1-(7-cyanoheptyl)indole (P);

(Example 147): 6-hexanamido-1-(8-[2(H)-tetrazol-5-yl]octyl)indole in 23% yield as a partial hydrate, m.p. 129°-131° C. starting from 6-hexanamido-1-(8-cyanooctyl)indole (Q);

(Example 148): 6-hexanamido-1-(4-[1(H)-tetrazol-5yl]benzyl)indole in 50% yield as a hemi-hydrate, m.p. 134°-136° C., starting from 1-(4-cyanobenzyl)-6-hexanamidoindole (R); and (Example 149): 6-hexanamido-1-(3-[1(H)-tetrazol-5-yl]benzyl) indole in 51% yield as a solid m.p. 214°-216° C. starting from 1-(3-cyanobenzyl)-6-hexanamidoindole (S).

The necessary starting material P was obtained as follows:

A stirred solution of 140 mg. 1-(7-bromoheptyl)-6-hexanamidoindole (obtained in 69% yield as a light yellow powder, m.p. 98°-101° C., by sodium hydride alkylation of 6-hexanamidoindole with 1,7-dibromoheptane according to the general method of Example 23) in 6 ml. dimethylsulphoxide was maintained under a nitrogen atmosphere and treated with 54 mg. sodium cyanide followed by 100 mg. 18-crown-6 (1,4,7,10,13,16-hexaoxacyclooctadecane). After 1 hour the solution was diluted with water and extracted with ethyl acetate. The combined extracts were washed with water, then brine, dried (MgSO4) and evaporated to give 1-(7-cyanoheptyl)indole (P) a white solid (82 mg., 67% yield), m.p. 85°-86° C., after recrysatillisation from ethyl acetate/hexane.

Starting material Q was made in an analogous manner using 1,8-dibromo-octane and obtained in 77% yield as a white solid, m.p. 104°-105° C.

Starting materials R and S were obtained as solids of m.p. 106°-109° C. and 133°-136° C. in yields of 59% and 44%, respectively, by sodium hydride alkylation of 6-hexanamidoindole with 4-bromomethyl- and 3-bromomethylbenzonitrile, respectively, using the general method of Example 23.

Example 150

Using a similar procedure to that described in Example 67, but starting from 1-(4-cyano-2-methoxybenzyl)-6-(2-ethylhexanamido)indole (T), there was obtained 6-(2-ethylhexanamido)-1-(2-methoxy-4-[1(H)-tetrazol-5-yl]benzyl)indole in 73% yield as a solid, m.p. 211°-212° C.

The starting nitrile T was obtained in 53% yield as a white solid, m.p. 177°-178°0 C., by sodium hydride alkylation of 6-(2-ethylhexanamido)indole with 4-bromomethyl-3-methoxybenzonitrile, using the general method of Example 23.

EXAMPLES 151-154

Using a similar procedure to that described in Example 67 the following tetrazole derivatives of formula 16 were obtained from the corresponding nitriles of formula 17:

| Ex. | Rd | $G^2$ (+ position on ring Q) | m.p. °C. | yield (%) |
|-----|--------|----------------|----------|-----|
| 151 | 2-OCH3 | direct link (4) | 118-120* | 29 |
| 152 | H | vinyl (4) | 252-255* | 15 |
| 153 | H | methylene (4) | 151-153 | 23 |
| 154 | H | methylene (3) | 167-170* | 76 |

*hemi-hydrate

The necessary starting nitriles of formula 17 for Exs.151 and 152 were obtained by sodium hydride alkylation of 6-(2-phenylbutanamido)indole (U) with the appropriate bromomethylbenzene using the general procedure of Example 23 and had the following properties:

(a) (for Ex.151): solid, m.p. 70°-72° C., obtained in 54% yield using 4-bromomethyl-3-methoxybenzonitrile and U; (b) (for Ex.153): solid, m.p. 132°-134° C. obtained in 51% yield using 3-(4-bromomethylphenyl)acrylonitrile and U.

The necessary nitriles of formula 17 for Exs. 153 and 154 were obtained in an analogous manner to that described for P in Example 146, that is by medium hydride alkylation of U with the appropriate alpha, alpha'-dibromoxylene followed by reaction of the intermediate 1-(bromomethylbenzyl)-6-(2-phenylbutanamido) indole with sodium cyanide in the presence of 18-crown-6. The nitriles and intermediate bromomethylbenzyl derivatives were used without characterisation.

The starting indole U was obtained as follows:

To a solution of 221 mg. of 1,1'-carbonyldiimidazole in 2 ml. methylene chloride which had been heated under reflux for 30 minutes in a nitrogen atmosphere and then cooled was added a solution of 200 mg. 6-aminoindole in 2 ml. methylene chloride. The mixture was stirred for 16 hours and then diluted with ethyl acetate. The ethyl acetate solution was then washed successively with 10% w/v aqueous hydrochloric acid, water and saturated brine, then dried (MgSO4) and evaporated. The residual oil obtained was purified by chromatography on silica gel using 20% v/v ethylacetate/hexane as eluent to give 6-(2-phenylbutanamido)indole (U) in 69% yield as a solid, m.p. 143°-144° C.

EXAMPLES 155-156

Using a similar procedure to that described in Example 73 the following tetrazoles were obtained:

(Example 155): 6-hexanamido-1-(7-[1(H)-tetrazol-5-ylthio]hepthyl)indole, in 11% yield as a partial hydrate, m.p. 116°-117°0 C., starting from 1-(7-bromoheptyl)6-hexanamidoindole; and (Example 156): 6-hexanamido-1-(5-[1(H)-tetrazole-5-ylthio]pentyl)indole, in 21% yield as a solid, m.p. 108°-109° C., starting from 1-(5-bromophenyl)-6-hexanamidoindole, (itself obtained in 61% yield as a solid, m.p. 60.5°-62° C. by sodium hydride alkylation of 6-hexanamidoindole with 1,5-dibromopentane using the general procedure of Example 23).

Example 157

A solution of 4.0 g. 6-amino-(2-methoxy-4-[(1H)tetrazole-5-yl]benzyl)indole (V) in a mixture of 10 ml. N-methylpyrrolidone, 10 ml. tetrahydrofuran and 2.2 ml. 2,6-lutidine was added dropwise to a stirred, ice-cooled solution of 2.57 g. butyl chloroformate in 10 ml. tetrahydrofuran, maintained under a nitrogen atmosphere. The mixture was allowed to attain room temperature during 2 hours and then left for 14 hours. Solid was removed by filtration and the filtrate was concentrated under reduced pressure. The oily residue was dissolved in 35 ml. of 20% w/v potassium carbonate solution, basified to pH10 with 10% w/v sodium hydroxide solution and extracted with ethyl acetate. These extracts were discarded. The aqueous phase was acidified to pH 1 with 6M hydrochloric acid and re-extracted with ethyl acetate. These extracts were combined, washed with water and then with saturated brine, dried ($MgSO_4$) and evaporated. The solid residue was recrystallised from ethyl acetate to give 2.8 g. (54%) of 6-(butoxycarbonyl)amino-1-(2-methoxy-4-[1(H)-tetrazol-5-yl]benzyl)indole as a yellow powder, m.p. 194°-195° C.; microanalysis, found: C, 62.69; H, 5.72; N, 20.00%; $C_{22}H_{24}N_6O_3$ requires: C, 62.58; H, 5.75; N, 19.99%.

The starting material V was obtained as follows:

(a) 6-Nitroindole as alkylated with 4-bromomethyl-3-methoxybenzonitrile in the presence of potassium carbonate using the general procedure described. in Ex 1(a) to give 1-(4-cyano-2-methoxybenzyl)-6-nitroindole (W) in 78% yield as a solid, m.p. 190.5°-191° C.

(b) The nitrile W was converted to the corresponding tetrazole, 1-(2-methoxy-4-[1-(H)-tetrazol-5-yl]benzyl)-6-nitroindole (X), obtained in 86% yield as a yellow-green solid, m.p. 258°-260° C. (d) using the general procedure of Example 67.

(c) A solution of 4.76 g. X in 2.3 ml. of 6M potassium hydroxide solution and 180 ml. methanol was treated with 480 ml. 10% w/w palladium on charcoal and then hydrogenated at a pressure of 3.45 bar for 2 hours. Catalyst was removed by filtration through diatomaceous earth and the filtrate was evaporated. Treatment of the residual oil with saturated monobasic sodium phosphate solution produced a precipitate which was collected and dried to give 6-amino-1-(2-methoxy-4-]1(H)-tetrazole-1-5 -yl]benzyl)indole (V) in quantitative yield as a grey powder; NMR: 4.0 (s, 3H, $OCH_3$), 5.2 (s,2H, $NCH_2$), 6.3 (d, 1H, $H^3$-indole), 6.4 (d,1H,$H^5$-indole), 6.5 (s, 1 aromatic H), 6.7 (d, 1aromatic H), 7.1 (d, 1H, $H^2$-indole), 7.2 (d, 1H, $H^4$-indole), 7.5 (d, 1 aromatic H), 7.7 s,1H, $H^7$-indole).

EXAMPLES 158-160

Using a similar procedure to that described in Example 157, but using cyclophenyl chloroformate as the acylating agent, there was obtained 6-(cyclopentyloxycarbonyl)amino-1-(2-methoxy-4-[1(H)tetrazol-5-yl]benzyl)indole (Example 158) in 57% yield as a solid, m.p. 216°-218° C.; microanalysis, found; C, 63.63; H, 5.28, N, 19.21%; $C_{23}H_{24}N_6O_3$ requires: C, 63.87; H, 5.59; N, 19.43%.

Similarly, using butyl chloroformate and 6-amino-1-(6-[1(H)-tetrazol-5-yl]hexyl)indole (Y), there was obtained 6-(butoxycarbonyl)amino-1-[6-[1(H)-tetrazol-5-yl) hexyl]indole (Example 159) in 44% yield as a white solid m.p. 117°-118° C. microanalysis found: C, 62.27; H, 7.34; N, 21.67%; $C_{20}H_{28}N_6O_2$ requires: C, 62.48; H, 7.34; N, 21.86%.

Similarly, using cyclopentyl chloroformate and indole Y, there was obtained 6-(cyclopenyloxycarbonyl)amino-1-(6-[1(H)-tetrazol-5-yl]hexyl)indole (Example 160) in 28% yield as a pale yellow powder, m.p. 141.5°-142.5° C.; microanalysis, found: C, 63.78; H, 7.10; N, 21.03%; $C_{21}H_{28}N_6O_2$ requires: C, 63.62; H, 7.12; N, 21.20%.

The starting material Y was obtained from 6-nitroindole and 7-bromoheptanonitrile using an analogous procedure to that for V given in Example 159.

Example 161

6-Amino-(2-methoxy-4-(1(H)-tetrazol-5-yl]benzyl)indazole (Z) was acylated with butyl chloroformate, using the procedure described in Example 159, to give 6-(butyloxycarbonyl)amino-1-(2-methoxy-4-[1(H)-tetrazol-5-yl]benzyl)indazole in 40% yield as a white solid, m.p. 210.5°-211.5° C. (d); microanalysis, found: C, 59.84; H, 5.69; N, 23.17%; $C_{21}H_{23}N_7O_3$: requires: C, 59.84; $H_7$ 5.50; N, 23.26%.

The starting material Z was obtained as follows:

(a) 4-(6-nitroindazol-1-yl)methyl-3-methoxybenzonitrile (AA) was obtained in 24% yield as a solid, m.p. 207°-208° C., from sodium 6-nitroindazolide and 4-bromomethyl-3-methoxybenzonitrile using an analogous procedure to that described for J in Ex. 22.

(b) 1-(2-methoxy-4-[1(H)-tetrazol-5-yl]benzyl-6-nitroindazole (BB) was obtained in 98% yield as a solid, m.p. 152°-153.5° C. (d) by reaction of benzonitrile AA with sodium azide and triethylamine hydrochoride in N-methyl-pyrrolidone at 150° C. for 3 hours under an atmosphere of nitrogen using the procedures described for Ex. 67.

(c) 6-Amino-1-(2-methoxy-4-[1(H)-tetrazol-5-yl]-benzyl)indazole (Z) was obtained in 79% yield as a pale yellow solid, m.p. 247°-248° C. (d), by 10% w/w palladium-on-charcoal catalyst hydrogenation (1.1 bar for 2 hours) of the nitro compound BB, using the procedure described for V in Example 157.

EXAMPLE 162

Using a similar procedure to that described in Ex. 161, but using cyclopentyl chloroformate as the acylating agent, there was obtained in 66% yield 6-(cyclopentyloxycarbonyl)amino-1-(2-methoxy-4-[1(H)-tetrazole-5-yl]benzyl)indazole as a white solid, m.p. 203.5°-204.5° C. (d); microanalysis, found: C, 60,90; H,5.43; N,22.24%; $C_{22}H_{23}N_7O_3$ requires: C, 60.95; H, 5.34; N,22.62%.

EXAMPLE 163

Using a similar procedure to that described in Example 161, but starting from 2-ethylhexanoyl chloride and 6-amino-1-(2-methoxy-4-[1(H)-tetrazol-5-yl]benzyl)indazole (V), there was obtained 6-(2-ethylhexanamido)-1-(2-methoxy-4-[2(H)-tetrazol-5-yl]benzyl)indazole in 56% yield as a white solid, m.p. 203°-204° C.; microanalysis, found: C,64.35; H,6.43; N, 21.80%; $C_{24}H_{29}N_7O_2$ requires: C,64.41; H,6.53; N,21.90%.

EXAMPLE 164

Using a similar procedure to that described in Example 9, but starting from 2-phenylbutyric acid and 6-amino-1-(2-methoxy-4-[1(H)-tetrazol-5-yl]benzyl)indazole (V), there was obtained 1-(2-methoxy-4-[1(H)-tetrazol-5-yl]benzyl)-6-(2-phenylbutanamido)indazole in 48% yield as a pale pink solid, m.p. 202°-203° C. (d); microanalysis, found: C, 66.05; H, 5.40; N, 20.70; $C_{26}H_{25}N_7O_2.0.25\ H_2O$ requires: C, 66.15; H, 5.44; N, 20.77%.

EXAMPLE 165

Using the analogous procedure to that described in Example 1, but starting from methyl 4-(6-aminoindazol-1-ylmethyl)-3-methoxybenzoate and 2-ethylhexanoyl chloride, there was obtained methyl 4-[6-(2-ethylhexanamido)-1-ylmethyl]-3-methoxybenzoate in 68% yield as a white solid, m.p. 135.5°-136.5° C.; microanalysis, found: C, 68.37; H, 7.10; N, 9.43%; $C_{25}H_{31},\ N_3O_4$ requires: C, 68.64; H, 7.14; N, 9.60%.

EXAMPLE 166

Using an analogous procedure to that described in Example 75, but starting from cyclopentyl chloroformte and methyl 4-(6-aminoindazol-1-ylmethyl)-3-methoxybenzoate, there was obtained methyl 4-[6-(cyclopentyloxycarbonyl) aminoindazol-1-ylmethyl]-3-methoxybenzoate in 73% yield as a pale pink solid, m.p. 150°-151° C.; microanalysis, found: C,65.05; H,5.95; N,9.47%; $C_{23}H_{25}N_3O_5$ requires: C, 65.24; H, 5.95; N,9.92%.

EXAMPLES 167–170

Using a similar procedure to that described in Example 34, the following carboxylic acids of the formula 18 were obtained by hydrolysis of the corresponding methyl esters:

| Example | Re | m.p. (°C.) | Yield (%) |
|---|---|---|---|
| 167 | 1-phenylpropyl | 244–245(d) | 76 |
| 168 | butoxy | 213.5–214(d) | 88 |
| 169 | 3-heptyl | 249–250.5 | 69 |
| 170 | cyclopentyloxy | 235–236.5 | 39 |

EXAMPLE 171

A solution of 0.52 g. t-butyl 4-(6-aminoindol-1-ylmethyl)-3-methoxybenzoate (CC) and 0.31 ml. triethylamine in 8 ml. methylene chloride was treated with 0.24 ml. heptafluorobutyryl chloride at 0° C. After stirring for 24 hours the solution was diluted with methylene chloride, washed successively with 10% v/v hydrochloric acid, water, and brine, then dried (MgSO$_4$) and evaporated. The residue was purified by flash chromatography on a 6×20 cm. silica gel column using 5% v/v ethyl acetate in hexane as the eluent to give 0.41 g. (51%) of t-butyl 4-(6-heptafluorobutanamidoindol-1-ylmethyl)-3-methoxybenzoate as a yellow solid; NMR: 1.6 [s, 9H, (CH$_3$)$_3$C], 3.9 (s, 3H, OCH$_2$), 5.3 (s, 2H, NCH$_2$), 6.5 (d, 1H, H$^3$-indole), 6.7 (d, 1H, Ar); 7.0 (d, 1H, H$^5$-indole), 7.4 (d,1H,H$^2$-indole), 7.9 (d, 1H, H$^7$-indole); 8.0 (s, 1H, CO.NH).

The starting amine (CC) was obtained as follows:

a) A solution of 10.0 g 3-methoxy-4-methylbenzoic acid, 1 ml. concentrated sulphuric acid, and 200 ml. condensed isobutylene in 200 ml. methylene chloride was placed in a pressure vessel and stirred for 16 hours. The vessel was then opened to vent unreacted isobutylene. The remaining liquid was poured into 150 ml. of 10% w/v sodium hydroxide solution and extracted twice with ethyl acetate. The combined extracts were washed with saturated brine, dried (MgSO$_4$), and evaporated. The residue was purified by flash chromatography on a 7×18 cm silica gel column using 10% v/v ethyl acetate in hexane as the eluant to give 9.1 g. (70%) of t-butyl 3-methoxy-4-methylbenzoate as a colourless oil; NMR: 1.6 [s,9H, C(CH$_3$)$_3$], 2.27 (s,3H,CH$_3$), 3.86 (s, 3H,OCH$_3$), 7.11 (d,1H), 7.49 (m,2H).

b) A suspension of 8.92 g. t-butyl 3-methoxy-4-methylbenzoate, 8.57 g. N-bromosuccinimide, and 0.1 g, benzoyl peroxide in 150 ml. carbontetrachloride was heated to reflux and iradiated with a sun lamp for 1 hour. After cooling to room temperature, solid was removed form the suspension by filtration. The filtrate was evaporated. The resultant residue was purified by flash chromatography on a 7×18 cm. silica gel column using 5% v/v ethyl acetate in hexane as the eluent to give 11.52 g. (95%) of t-butyl 3-methoxy-4-bromomethylbenzoate as a pale yellow oil; NMR: 1.5 (s,9H, C(CH$_3$)$_3$], 3.9 (s,3H, OCH$_3$), 4.5 (s, 2H, CH$_2$Br), 7.15 (d, 1H), 7.4 (m, 2H).

c) t-Butyl 3-methoxy-4-bromomethyl benzoate was reacted with 6-nitroindole and potassium carbonate using the procedure described in part (a) of Example 1 to give in 98% yield t-butyl 4-(6-nitroindol-1-ylmethyl)-3-methoxybenzoate as a yellow solid; NMR: 0.6 [s, 9H, C(CH$_3$)$_3$], 4.9 (s, 3H, OCH$_3$), 5.4 (s, 2H, NCH$_2$) 6.6 (dd, 1H, H$^3$−indole), 6.8 (d, 1 aromatic H), 6.8–8.0 (m, 5H, Ar), 8.4 (d, 1H, H$^7$-indole).

d) t-Butyl 4-(6-nitroindol-1-ylmethyl)-3-methoxybenzoate was catalytically hydrogenated using the procedure described in part (b) of Example 1 to give a quantitative yield of t-butyl 4-(6-aminoindol-1-ylmethyl)-3-methoxybenzoate (CC) as a light brown solid; partial NMR: 1.6 [s, 9H, (CH$_3$)$_3$C], 4.1 (br d, 2H, NH$_2$), 5.2 (s, 2H, NCH$_2$).

EXAMPLE 172

A solution of 0.25 g. t-butyl 4-(6-heptafluorobutanamidoindol-1-ylmethyl)-3-methoxybenzoate and 152.3 microlitres triethylamine in 1.0 ml. dioxane was treated with 185 microlitres trimethylsilyl triflate and the mixture stirred for 48 hours. Addition of water then gave a precipitate which was collected by filtration and recrystallised from ethyl acetate/hexane to give 22 mg. (10%) of 4-(6-heptafluorobutanamidoindol-1-ylmethyl)-3-methoxybenzoic acid as a light brown powder, m.p. 213°–215° C.; microanalysis, found: C, 51.27; H, 3.24; N, 5.47%; $C_{21}H_{15}N_2O_4F_7$ requires: C, 51.23; H, 3.07; N, 5.69%.

EXAMPLE 173

A solution of 0.76 g. methyl 4-[6-(N-butoxycarbonyl-)aminoindol-1-ylmethyl]-3-methoxybenzoate in 10 ml.

carbon tetrachloride was added to a suspension of 0.25 g. N-chlorosuccinimide in 9 ml. carbon tetrachloride. The mixture was heated under reflux for 45 minutes, cooled and succinimide removed by filtration. The filtrate was washed with saturated sodium bicarbonate solution, then with brine, dried (MgSO$_4$) and evaporated. The residue was purified by flash chromatography on a 4×20 cm. silica gel column using 25% v/v hexane in methylene chloride as the eluent. There was thus obtained 0.36 g. (44%) of methyl 4-[6-(butoxycarbonyl)amino-3-chloroindol-1-ylmethyl]-3-methoxybenzoate as a white solid; NMR: 0.9 [t, 3H, (CH$_2$)$_3$CH$_3$], 1.4 [br m, 4H, CH$_2$(CH$_2$)$_2$CH$_3$], 3.8 (s, 3H, OCH$_3$), 3.9 (s, 3H, OCH$_3$), 4.1 [t, 2H, CH$_2$(CH$_2$)$_2$CH$_3$], 5.2 (s, 2H, NCH$_2$), 6.6 (d, 1 aromatic H), 6.75 (dd, 1H, H$^5$-indole), 6.8 (s, 1H, NH), 7.0 (3, 1H, H$^2$-indole), 7.4 (d, 1 aromatic H), 7.5 (s, 1 aromatic H), 7.7 (s, 1H, H$^7$-indole).

EXAMPLE 174

A solution of 0.5 g. 3-acetyl-6-(2-ethylhexanamido)indole (DD) in 4 ml. of dimethylformamide was added to a slurry of 0.072 g. sodium hydride in 2 ml. of dimethylformamide and the mixture stirred for 1 hour. A solution of 0.518 g. methyl 4-bromomethyl-3-methoxybenzoate in 2 ml. of dimethylformamide was then added and the mixture stirred for a further 1 hour. The reaction mixture was then quenched by addition of saturated ammonium chloride solution, diluted with water and extracted with ethyl acetate. The combined extracts were washed with water, then with saturated brine, dried (MgSO$_4$) and evaporated. The residue was purified by flash chromatography on a 5×20 cm. silica gel column using 50% v/v ethyl acetate in hexane as the eluent to give 0.3 g. of methyl 4-[3-acetyl-6-(2-ethylhexanamido)indol-1-ylmethyl]-3-methoxybenzoate as a white solid; NMR: 0.9 (t, 6H, 2CH$_3$), 2.1 (t, 1H, CO.CH), 2.4 (s, 3H, CO.CH$_3$), 3.8 (s, 3H, OCH$_3$), 3.9 (s, 3H, OCH$_3$), 5.3 (s, 2H, NCH$_2$), 6.8 (d, 1 aromatic H), 6.9 (dd, 1H, H$^5$-indole), 7.3 (s, 1H, NH), 7.48 (dd, 1 aromatic H), 7.5 (s, 1H, H$^2$-indole), 7.6 (s, 1 aromatic H), 8.2 (d, 1H, H$^4$-indole), 8.3 (s, 1H, H$^7$-indole).

The starting indole DD was obtained as follows:

1.9 g. of phosphorus oxychloride was slowly added to 1.48 g. of N,N-dimethylacetamide at 0° C. The mixture was allowed to attain room temperature and a solution of 1.0 g. 6-(2-ethylhexanamido)indole in 2 ml. N,N-dimethylacetamide was added. After 15 minutes the reaction solution was basified to pH 14 with 20% w/v sodium hydroxide solution, briefly heated under reflux, then cooled and extracted with ethyl acetate. The combined extracts were washed with water, then with brine, dried (MgSO$_4$) and evaporated to give 0.93 g (80%) of 3-acetyl-6-(2-ethylhexanamido)indole (DD) as an orange powder; partial NMR: 2.5 (s, 3H), COCH$_3$), 7.7 (d, 1H, H$^2$-indole), 9.8 (br, s, 1H, NH).

EXAMPLE 175

Using a similar procedure to that described in Ex. 174, but starting from 6-(2-ethylhexananido)-3-methylindole (EE) and methyl 4-bromomethyl-3-methoxybenzoate, there was obtained methyl 4-[6-(2-ethylhexanamido)-3-methylindol-1-ylmethyl]-3-methoxybenzoate in 42% yield as a white solid; partial NMR: 0.9 (t, 6H, 2CH$_3$), 2.3 (d, 3H, indole-CH$_3$), 3.8 (s, 3H, OCH$_3$), 3.9 (s, 3H, OCH$_3$), 5.2 (s, 2H, NCH$_2$), 6.6 (d, 1H, m-OCH$_3$), 6.8 (dd, 1H, H$^5$-indole), 7.2 (s, 1H, NH), 8.0 (d, 1H, H$^7$-indole).

The 3-methylindole EE was obtained as follows:

(a) 6-(2-Ethylhexanamido)-3-formylindole was prepared in 71% yield as a white solid [partial NMR: 8.7 (d, 1H, H$^2$-indole), 11.0 (s, 1H, CO.H), 11.7 (br s, 1N, NH)] using an analogous procedure to that described for DD in Example 176 but using dimethylformamide in place of N,N-dimethylacetamide.

(b) 0.239 g. Lithium aluminium hydride was slowly added to a solution of 0.9 g. of 6-(2-ethylhexanamido)-3-formylindole in freshly distilled tetrahydrofuran. The mixture was heated under reflux for 30 minutes, then cooled to room temperature and 10% w/v sodium sulphate solution added dropwise until effervescence stopped. The white granular precipitate which formed was removed by filtration. The filtrate was dried (MgSO$_4$) and evaporated. The residue was purified by flash chromatography on a 6×20 cm. silica gel column using 25% v/v ethyl acetate in hexane as eluent to give 0.51 g. (60%) of 6-(2-ethylhexanamido)-3-methylindole (EE) as a white powder; partial NMR: 2.3 (s, 3H, indole-CH$_3$).

EXAMPLE 176

Using a similar procedure to that described in Example 34, there was obtained 4-[6-(cyclopentyloxycarbonyl)aminoindol-1-ylmethyl]-3-methoxybenzoic acid in 55% yield as a white solid, m.p. 237°-238° C., by hydrolysis of the corresponding methyl ester.

EXAMPLES 177-179

Using a similar procedure to that described in Example 9 but using the appropriate carboxylic acid of the formula Re.CO$_2$H, the following esters of formula 1 were obtained:

| Ex | Re | Yield (%) | Partial NMR |
|---|---|---|---|
| 177 | cyclohexylmethyl | 57 | 2.2(d, 2H, CH$_2$CO), 7.2(br s, 1H, NH) |
| 178 | 1-phenylpropyl+ | 62 | 0.91(t, 3H, CH$_2$CH$_3$), 3.4(t, 1H, CHCH$_2$), 7.1(br s, 1H, NH), |
| 179 | 1-phenylpropyl++ | 71 | 7.4(s, 5H, Ph) |

+starting from R(−)-2-phenylbutyric acid
++starting from S(+)-2-phenylbutyric acid

EXAMPLES 180-181

Using the same chlorination procedure as is described in Example 173, these were obtained:

(Example 180): methyl 4-[3-chloro-6-(cyclopentyloxycarbonyl)aminoindol-1-ylmethyl]-3-methoxybenzoate, in 21% yield as a solid, partial NMR: 1.7–1.8 [br m, 8H, (CH$_2$)$_4$], 3.88 (s,3H,OCH$_3$), 3.94 (s,3H,OCH$_3$), 6.6 (br s, 1H,NH), 7.0 (s,1H,H$^2$-indole), starting from methyl 4-[6-(N-cyclopentyloxycarbonylamino)indole-1-ylmethyl]-3-methoxybenzoate; and (Example 181): methyl 4-[3-chloro-6-(2-cyclopentyl acetamido)indol-1-ylmethyl]-3-methoxybenzoate, in 75% yield as a solid, partial NMR: 2.3 (br s,3H, CHCH$_2$), 3.88 (s,3H,OCH$_3$), 3.93 (s,3H,OCH$_3$), 7.0 (s,1H,H$^2$-indole), 7.2 (br s,1H,NH), starting from methyl 4-[6-(2-cyclopentylacetamido)indol-1-ylmethyl]-3-methoxybenzoate.

EXAMPLES 182-184

Using a similar procedure to that described in Example 90 but starting with the appropriate alcohol the following esters of formula 11 were obtained:

| Example | Re | Yield (%) | Partial NMR |
| --- | --- | --- | --- |
| 182 | isopropyl | 71 | 1.9[d, 6H, CH(C$\underline{H}$₃)₂], 3.87 + 3.94(2s, 2×3H, OCH₃), 4.8–5.2[m, 1H, C$\underline{H}$(CH₃)₂] |
| 183 | tetrahydro-fur-3-yl | 68 | 1.9–2.3(m, 2H, C$\underline{H}$₂CH), 3.7–4.1(m, 4H, C$\underline{H}$₂OC$\underline{H}$₂), 5.2–5.4(m, 1H, CH.O) |
| 184 | 1-cylohexen-4-yl | 56 | 1.5–2.5[m, 6H, C$\underline{H}$₂.CH.(C$\underline{H}$₂)₂], 4.9–5.2(m, 1H, CH.O), 5.2–5.7 (m, 2H, CH=CH) |

EXAMPLE 185

A mixture of 0.91 g. of methyl 4-(6-aminoindol-1-ylmethyl)-3-methoxybenzoate, 0.57 g. of 1-(3-dimethylaminopropyl)-3-ethylcarbodiimide hydrochloride, 0.37 g. 4-dimethylaminopyridine and 0.61 g. 2-cyclopentyl-2-phenylacetic acid in 15 ml. of methylene chloride was stirred for 24 hours. The reaction solution was diluted with methylene chloride and washed successively with 10% v/v hydrochloric acid, water, 20% w/v sodium hydroxide, water, and brine; then dried (MgSO₄) and evaporated to give 0.96 g. (66%) of methyl 4-[6-(2-cyclopentyl-2-phenylacetamidoindol)-1-ylmethyl]-3-methoxybenzoate as a light brown solid;

NMR 0.9–1.8 (br m, 8H, (CH₂)₄), 2.6 (m,1H,CHCHCO), 3.87 (s,3H,OCH₃), 3.9 (s, 3H,OCH₃), 5.2 (s,2H,NCH₂), 6.5 (d,1H, H³-indole), 6.6 (d,1H, m-MeO-C₅H₃), 6.8 (dd,1H,H⁵-indole), 7.1 (d,1H,H²-indole), 8.0 (br s, 1H,H⁷-indole).

EXAMPLES 186–190

Using a similar procedure to that described in Example 185 but using the appropriate acid Re.CO₂H, the following esters of formula 1 were obtained:

| Ex. | Re | Yield | Partial NMR |
| --- | --- | --- | --- |
| 186 | 1-cyclohexyl-propyl | 40 | 0.74–1.3(br m, 5H, CH₂CH₃), 1.4–2.0(br m, 12H) |
| 187 | 1-methyl-1-phenylethyl | 59 | 1.65[s, 6H, C(CH₃)₂] |
| 188 | 1-phenyl-cyclopentyl | 30 | 1.5–2.8[br m, 9H, (CH₂)₄CH], 6.69(br s, 1H, NH) |
| 189 | alpha-methoxy-benzyl | 46 | 3.4(s, 3H, OCH₃), 4.7(s, 1H, C$\underline{H}$OCH₃), 8.6(br s, 1H, NH) |
| 190 | 1-cyclopentyl-butyl | 34 | 0.9(t, 3H, CH₂C$\underline{H}$₃), 1.0–2.1 [brm, 14H, (CH₂)₄CH.CH—(CH₂)₂], 7.1(br s, 1H, NH) |

EXAMPLE 191

Using a similar procedure to that described in Ex.174 but starting from 3-acetyl-6-(N-(cyclopentyloxycarbonyl)aminoindole and methyl 4-bromomethyl-3-methoxybenzoate and using potassium carbonate in place of sodium hydride, there was obtained methyl 4-[3-acetyl-6-(N-cyclopentyloxycarbonylamino)indol-1-ylmethyl]-3-methoxybenzoate in 78% yield as an off-white solid; partial NMR: 1.5–2.0 [br m, 8H,(CH₂)₄], 5.2 (s,3H,CO.CH₃), 3.88 (s,3H,OCH₃), 3.94 (s,3H,OCH₃), 5.2 (m,1H,CH.O). The starting indole was obtained using a similar procedure to that described for indole DD in Example 174, but starting from 6-(N-cyclopentyloxycarbonylamino)indole and was isolated in 31% yield as a light brown powder, partial NMR: 1.5–2.0 [br m,8H,(CH₂)₄], 2.5 (s,3H,CO.CH₃) 5.2 (m, 1H,CH.O), 7.3 (d,1H,H²-indole).

6-(N-Cyclopentyloxycarbonylamino)indole was itself obtained in 44% yield as a white solid; NMR: 1.5–2.0 [br m,8H,(CH₂)₄], 5.1–5.4 (m,1H,CH.O), 6.4 (m,1H,H³-indole), 6.5 (br s,1H,NH), 7.1 (m,1H,H²-indole); by reaction of 6-aminoindole with cyclopentyl chloroformate using a similar procedure to that described in Example 22.

EXAMPLE 192

Using a similar procedure to that described in Example 185, but starting from methyl 4-(6-aminoindolin-1-ylmethyl)-3-methoxybenzoate and 2-cyclopentylacetic acid, there was obtained methyl 4-[6-(2-cyclopentylacetamido) indolin-1-ylmethyl]-3-methoxybenzoate in 26% yield as an off-white solid, partial NMR: 2.3 (br s,3H,CHCH₂), 3.0 (t,2H,H³-indoline), 3.4 (t,2H,H²-indoline).

EXAMPLE 193

A solution of 0.5 g. 5-(N-pentylcarbamoyl)indole (FF) in 7 ml. of N,N-dimethylformamide (DMF) was added to a stirred slurry of 0.095 g. sodium hydride in 2 ml of DMF. After one hour, a solution of 0.68 g. methyl 4-bromomethyl-3-methoxy benzoate in 5 ml. of DMF was added. Stirring was continued for 24 hours and then the reaction was quenched by addition of saturated ammonium chloride solution. The mixture obtained was diluted with water and extracted with ethyl acetate. The organic phase was washed with water and brine, dried (MgSO₄), and evaporated. The residue was purified by flash chromatography (6×20 cm. silica gel column) using 30% v/v ethyl acetate in hexane as eluent to give 0.51 g (57%) of methyl 3-methoxy-4-[5-(N-pentylcarbamoyl)indol- 1-ylmethyl]benzoate as an off-white solid; partial NMR: 0.9 [t,3H,(CH₂)₄CH₃], 1.2–1.8 [br m,6H,CH₃(CH₂)₃]3.3–3.6 [m,2H,(CH₂)₃CH₂], 3.87 (s,3H,OCH₃), 3.9 (s,3H,OCH₃), 5.4 (s,2H,NCH₂).

The starting carbamoylindole FF was obtained as follows:

A solution of 0.5 g. indole-5-carboxylic acid and 0.54 g. of 1,1'-carbonyldiimidazole in 10 ml. of methylene chloride was heated under reflux for 30 minutes. A solution of 0.3 g. pentylamine in 2 ml. of methylene chloride was then added and heating under reflux was continued for a further 30 minutes. The reaction mixture was diluted with chloroform, washed successively with 10% v/v hydrochloric acid, water and brine, then dried (MgSO₄), and evaporated to give 0.51 g. (71%) of 5-(N-pentylcarbamoyl)indole as an off-white solid; partial NMR: 0.9 [t,3H,CH₃)CH₂)₄], 1.2–1.9 (br m,8H,CH₃(CH₂)₄, 6.2 (br s,1H, H¹-indole), 6.6 (m,1H,H³-indole), 8.6 (br s,1H,NH).

EXAMPLE 194

Using a similar procedure to that described in Ex.174, but starting from 3-butyryl-6-cyclopentylacetamidoindole, methyl 4-[3-butyryl-6-cyclopentylacetamidoindol-1-ylmethyl]-3-methoxybenzoate was obtained in 77% yield as a white solid; NMR: 0.94 (t,3H,CH₂CH₃), 2.26 (br s,3H,CHCH₂) 2.79 (t,2H,COCH₂), 3.83 (s,3H,OCH₃), 3.97 (s,3H,OCH₃), 5.42 (s,2H,NCH₂), 6.89 (d,1H,m-CH₃O.C₆H₃), 7.24 (dd,1H,H⁵-indole) 9.81 (s,1H,NH).

EXAMPLE 195

A solution of 1.54 g. t-butyl 4-[6-(2-ethylhexanamido)-3-formylindol-1-ylmethyl]-3-methoxybenzoate and 2.24 g. methyl (triphenylphosphoranylidene)acetate in 30 ml. of dioxane was heated under reflux for 2 days. The solvent was evaporated and the residue was purified by flash chromatography (6×20 cm silica gel column) using 20% v/v hexane in ethyl acetate as the eluent to give 1.69 g. (99%) t-butyl 4-[3-(2-methoxycarbonylethylidenyl]-6-(2-ethylhexanamido)indol-1-ylmethyl]-3-methoxybenzoate as a white solid; partial NMR: 0.96 (t,6H, $(CH_2CH_2)_2$), 1.54 [s,9H,$C(CH_3)_3$], 3.79 (s,3H,$OCH_3$), 3.92 (s,3H,$OCH_3$), 2.89 (s,2H,$NCH_2$), 6.35 (d,1H,CH=CH), 7.83 (d,1H,CH=CH).

The starting indole was obtained using a similar procedure to that descried in Ex.174, but starting from 6-(2-ethylhexanamido)-3-formylindole and t-butyl 4-bromomethyl-3-methoxybenzoate, and was isolated in 77% yield as a white solid; NMR: 0.96 [t,6H,$(CH_2CH_3)_2$], 1.57 [s,9H,$C(CH_3)_3$], 3.92 (s,3H,$OCH_3$), 5.34 (s,2H,$NCH_2$), 9.92 (s,1H,$CO.H$).

EXAMPLE 196

To a slurry of 0.075 g. 4-[3-(2-methoxycarbonylvinyl)-6-(2-ethylhexanamido)indol-1-ylmethyl]-3-methoxybenzoic acid in 5 ml. of methanol was added 25 microlitres of 6M potassium hydroxide solution. The solution obtained was hydrogenated in the presence of 0.02 g. of 10% w/w palladium on charcoal, using hydrogen at a pressure of 3.45 bar (50 p.s.i.). The catalyst was removed by filtration through diatomaceous earth. The filtrate was acidified (10% w/v hydrochloric acid). The resultant precipitate was collected by filtration and recrystallised from ethyl acetate/hexane to give 15.6 mg. (21%) 4-[3-(2-methyoxycarbonylethyl)-6-(2-ethylhexanamido)indol-1-ylmethyl]-3-methoxybenzoic acid as a white solid, m.p. 189–190; microanalysis, found: C, 65.92; H,7.05; N 4.93%; $C_{29}H_{36}N_2O_6.H_2O$ requires: C, 66.14; H,7.27; N,5.31%.

EXAMPLE 197

Using a similar procedure to that described in Example 185, but starting from methyl 4-(6-amino-5-bromoindol-1-ylmethyl)-3-methoxybenzoate (GG) and cyclopentylacetic acid, methyl 4-[5-bromo-6-cyclopentylacetamidoindol-1-ylmethyl]-3-methoxybenzoate was obtained in 60% yield as an off-white solid; partial NMR: 1.6 [br m,8H,$(CH_2)_4$], 3.8 (s,3H,$OCH_3$), 3.9 (s,3H,$OCH_3$), 5.3 (s,2H,$NCH_2$), 6.4 (dd,1H,$H^3$-indole), 7.1 (d,1H,$H^2$-indole), 7.7 (br, 1H,NH), 7.8 (s,1H,$H^4$-indole), 8.5 (br s,1H,$H^7$-indole).

The starting 5-bromoindole GG was obtained as follows:

a) a solution of 1.21 g. 5-bromo-6-nitroindoline and 1.35 g. chloranil in 30 ml. xylene was heated under reflux for 4.5 hours. The dark mixture was filtered. The filtrate was washed twice with 10% v/v sodium hydroxide then with water followed by brine, and then dried (MgSO$_4$) and evaporated. The residue was purified by flash chromatography (6×18 cm. silica gel column) using 20% v/v hexane in methylene chloride as eluent, to give 0.68 g. (57%) 5-bromo-6-nitroindole as a yellow solid; NMR: 6.6 (br m, 1H,$H^3$), 7.5 (dd,1H,$H^2$), 7.9 (s,1H,$H^4$), 8.1 (dd,1H, $H^7$), 8.6 (br,1H,NH).

b) 5-Bromo-6-nitroindole was reacted with methyl 4-bromomethyl-3-methoxybenzoate using the procedure described in part (a) of Example 1 to give methyl 4-(5-bromo-6-nitroindol-1-ylmethyl)-3-methoxybenzoate (HH) in 65% yield and as a bright yellow solid; partial NMR: 3.89 (s,3H,$OCH_3$), 3.94 (s,3H,$OCH_3$), 5.35 (s,2H,$NCH_2$), 6.53 (dd,1H,$H^3$-indole), 7.38 (d,1H,$H^2$-indole), 7.89 (s,1H,$H^4$-indole), 8.03 (br s,1H,$H^7$-indole).

c) A solution of 0.66 g. HH in 100 ml. of 10% v/v acetic acid in ethyl acetate was hydrogenated in the presence of 0.10 g. of 5% w/w platinum on carbon and using hydrogen at a pressure of 2.76 bar (40 p.s.i.) for 4 hours. The catalyst was removed by filtration through diatomaceous earth. The filtrate was washed successively with 10M sodium hydroxide solution, water and brine, then dried (MgSO$_4$) and evaporated to give 0.61 g. methyl 4-(6-amino-5-bromoindol-1-ylmethyl)-3-methoxybenzoate (GG) as an oil; partial NMR: 6.37 (dd,1H,$H^3$-indole), 6.59 (s,1H,$H^7$-indole), 6.93 (d,1H,$H^2$-indole), 7.69 (s,1H,$H^4$-indole).

EXAMPLE 198

Using a similar procedure to that described in Example 193 but starting from 5-N-(2-methylpropyl)carbamoylindole there was obtained methyl 4-[5-N-(2-methylpropyl)carbamoylindol-1-ylmethyl]-3-methoxybenzoate in 4% yield as a white solid; NMR: 1.00 [d,6H,$(CH_3)_2CH$], 3.31 (t,2H,CHCH$_2$), 3.88 (s,3H,$OCH_3$), 3.94 (s,3H,$OCH_3$), 5.36 (s,2H,$NCH_2$), 5.14 (br s,1H,NH).

The starting carbamoylindole was obtained using a similar procedure to that described for the starting indole in Example 193 using isobutylamine instead of pentylamine and was isolated in 78% yield as a white foam; NMR: 1.00 [d,6H,$(CH_3)_2CH$], 3.32 (t,2H,CHCH$_2$), 6.23 (br s,1H,NH), 6.57 (m,1H,$H^3$-indole), 8.07 (br s,1H,$H^4$-indole), 8.73 (br s,1H,NH).

EXAMPLE 199

Using a similar procedure to that described in Example 193, but starting from 6-N-(cyclopentylmethyl)carbamoylindole (II), methyl 3-methoxy-4-[6-N-(cyclopentylmethyl)carbamoylindol-1-ylmethyl]benzoate was obtained in 37% yield as an off-white solid; NMR: 1.41–1.79 [m,8H,$(CH_2)_4$], 3.39 (t,2H,CH$_2$NH), 3.88 (s,3H,$OCH_3$), 3.92 (s,3H,$)CH_3$), 4.24 (s,2H,$NCH_2$), 6.17 (t,1H,CH$_2$NH), 6.62 (d,1H,$H^3$-indole), 6.72 (d,1H,m-$CH_3O-C_6H_3$), 7.91 (s,1H,$H^7$-indole).

The starting indole II was obtained as follows:

a) A solution of 4.46 g. methyl 4-methyl-3-nitrobenzoate in 23 ml. of DMF was treated with 8.18 g. N,N-dimethylformamide dimethyl acetal and heated to 130° for two hours. The DMF was evaporated and the residue was triturated with ether to give 5.58 g. (98%) of methyl 4-(2E -N,N-dimethylaminovinyl)-3-nitrobenzoate (JJ) as a red powder; NMR: 2.98 [s,6H,N(CH$_3$)$_2$], 5.90 (d,1H,CHN), 7.14 (d,1H,CH-CHN), 7.45 (d,1H,phenyl-$H^5$), 7.90 (dd,1H,5-phenyl-$H^6$), 8.47 (d,1H,phenyl-$H^2$).

b) A solution of 5.58 g. JJ in 100 ml of THF was hydrogenated at 3.45 bar (50 p.s.i.) in the presence of 1.1 g. of 10% w/w palladium on carbon for 35 minutes. The catalyst was removed by filtration through diatomaceous earth and the filtrate was evaporated. The residue was dissolved in ethyl acetate and the solution obtained was washed successively with 10% v/v hydrochloric acid, water and brine, then dried (MgSO$_4$) and evaporated to give 3.32 g. (85%) of methyl indole-6-carboxylate as a white solid, NMR: 3.92 (s,3H,$OCH_3$), 6.57 (m,1H,$H^3$-indole) 7.32 (t,1H,$H^2$-indole), 7.10

(d,1H,H$^4$-indole), 7.87 (dd,1H,H$^5$-indole), 8.16 (br s,1H,H$^7$-indole).

A solution of 3.32 g. of methyl indole-6-carboxylate in 48 ml. methanol was stirred at 50° C. for two hours with a solution of 4.78 g. lithium hydroxide monohydrate in 19 ml. of water. The solvent was evaporated and the residue was dissolved in water. The alkaline solution obtained was slowly acifified (HCl) and the precipitate which formed was collected to give 2.8 g. (92%) indole-6-carboxylic acid as a brown powder; NMR: 6.51 (m,1H,H$^3$-indole), 8.04 (m,1H,H$^7$-indole), 11.43 (br s, 1H,NH), 12.42 (br s, 1H,OH).

d) Indole-6-carboxylic acid was reacted with 1-cyclopentylmethylamine using a similar procedure to that decribed for indole GG in Example 193 to give 6-N-(cyclopentylmethyl)carbamoylindole (II) in 42% yield as a pale pink powder; NMR: 3.19 (d,2H,CH$_2$NH), 6.46 (d,1H, H$^3$-indole), 7.91 (d,1H,H$^7$-indole), 8.29 (t,1H,CH$_2$NH).

Example 200

Using a similar procedure to that described in Example 99, but using methyl 7-(bromomethyl)benzo[b]furan-4-carboxylate (KK) as alkylating agent, there was obtained methyl 7-[6-(2-ethylhexanamido)indol-1-yl-methyl]benzo[b]furan-4-carboxylate in 23% yield as a solid, m.p. 164°-167° C.; partial NMR (250 MHz; d$_6$DMSO): (0.84 (2t,6H, 2×CH$_3$), 1.0-1.6 (m,8H); 2.25 (m,1H,CHCO); 3.89 (s,3H,OCH$_3$); 5.75 (s,2H,NCH$_2$).

The starting material JJ was obtained as follows:

(a) A mixture of 3.46 g. potassium carbonate, 3.32 g. methyl 3-hydroxy-4-methylbenzoate and 2.16 ml. allyl bromide in 80 ml. acetone was heated under reflux for 6 hours. The cooled mixture was separated by filtration. The filter cake was washed with acetone and the washings combined with the filtrate and evaporated to give 3.85 g. (93%) of methyl 3-allyloxy-4-methylbenzoate as a clear oil; partial NMR: 2.3 (s,3H, C—CH$_3$), 3.9 (s,3H,O.CH$_3$), 4.6 (m,2H,0.CH$_2$).

(b) 1.2 g. of the 3-allyloxy compound from (a) was heated at 200° C. under nitrogen for 5 hours, cooled and purified by flash chromatography (5 cm. diameter silica gel column) using 92:8 v/v hexane in ethyl acetate as eluent, to give 0.79 g. (66%) of methyl 2-allyl-3-hydroxy-4-methylbenzoate as a white solid, m.p. 53°-56° C., having a satisfactory NMR spectrum.

(c) A stream of ozone in oxygen was bubbled into a solution of 0.78 g. of the 2-allyl compound from (b) in 25 ml. methanol at −78° C. for 10 minutes. The reaction was then purged of ozone by passing nitrogen through the solution for 2 minutes and then adding 1.5 ml. dimethylsulphide and allowing the mixture to attain room temperature. After 3 hours solvent was evaporated and the residual oil was purified by flash chromatography (4 cm. diameter silica gel column) using 40:60: v/v ethyl acetate in hexane as eluant, to give 0.33 g. (42%) of methyl 2-hydroxy-7-methyl-2,3-dihydrobenzo[b]furan-4-carboxylate as a white solid, m.p. 112°-115° C., having a satisfactory NMR spectrum. (d) 0.5 g. of the benzo[b]furan obtained in (c) was dissolved in toluene (10 ml.) and 3 mg. of p-toluene-sulphonic acid added. The mixture was stirred and heated under reflux for 6 hours. The cooled mixture was diluted with ether and washed successively with saturated sodium hydrogen carbonate solution, water and brine, then dried and solvent evaporated to give 0.43 g. (94%) of methyl 7-methylbenzo[b-]furan-4-carboxylate as a colorless oil; NMR: 2.58 (s,3H,C.CH$_3$), 3.96 (s,3H,0.CH$_3$), 7.10 (d J=7.7Hz, 1H,H$^6$), 7.35 (d J=2.1Hz, 1H, H$^3$), 7.90 (d J=7.7 Hz, 1H,H$^5$). (e) A mixture of 0.42 g. of the ester obtained in (d) together with 0.409 g. N-bromosuccinimide and 5 mg. benzoyl peroxide in 20 ml carbon tetrachloride was stirred and heated under reflux for 3 hours with infrared irradiation. The cooled mixture was concentrated in vacuo and the residue purified by flash chromatography (4 cm diameter silica gel column) using 2.5: 97.5 v/v ether in hexane as the eluant to give methyl 7-(bromomethyl)benzo[b]furan-4-carboxylate (JJ) as a solid which was purified by recrystallistaion from hexane at −20° C. to give 0.27 g. (47%) of pale yellow solid, m.p. 73°-80° C., having a satisfactory NMR spectrum.

EXAMPLES 201 -206

Using a similar procedure to that described in Example 99, but using the appropriate bromomethyl compound of formula 13 (R$^1$=CH$_3$) the following esters of formula 12 (R$^1$=CH$_3$) were obtained:

| Ex. | Rd | G$^2$ (and location on Q) | Yield (%) | m.p. (°C.) |
|---|---|---|---|---|
| 201 | 2-OCH$_3$ | direct link (3) | 37 | 107–110 |
| 202 | 4-OCH$_3$ | direct link (3) | 45 | 144–145 |
| 203 | 3-OCH$_3$ | direct link (3) | 23% | (+) |
| 204 | 2-Cl | direct link (4) | 38% | (++) |
| 205 | 2,6-(OCH$_3$)$_2$ | direct link (4) | 65% | 185–186 |
| 206 | 2-CH$_3$ | direct link (4) | 55% | 169–171 |

(+) partial NMR: 5.2(s, 2H, CH$_2$N), 3.85(s, 3H, O.CH$_3$), 3.78(s, 3H, O.CH$_3$)2.0(m, 1H, CH.CO).

(++) microanalysis, found: C, 67.85; H, 6.94; N, 5.62%; C$_{25}$H$_{29}$ClN$_2$O$_3$ requires: C, 68.09; H, 6.63; N, 6.35%.

The required starting materials of formula 13 (R$^1$=CH$_3$) were obtained as follows using similar procedures to those described in parts (c) and (d) of Example 1:

(a) (for Ex.201): methyl 3-bromomethyl-2-methoxybenzoate, obtained in 72% yield as an oil; NMR: 3.9 (s,3H,OCH$_3$), 4.0 (s,3H,OCH$_3$), 4.6 (s,2H,CH$_2$Br), 7.07-7.8 (m,3H); by bromination of methyl 2-methoxy-3-methylbenzoate, itself obtained as an oil in 87% yield by esterification of the corresponding acid.

(b) (for Ex.202): methyl 5-bromomethyl-2-methoxybenzoate, obtained in 47% yield as a white solid, m.p. 78°-79°, by bromination of methyl 2-methoxy-5-methylbenzoate, itself obtained as an oil by esterification of the corresponding acid;

(c) (for Ex.203): methyl 4-bromomethyl-2-methoxybenzoate, obtained as an oil by bromination of methyl 2-methoxy-4-metrhylbenzoate, itself obtained as an oil by esterification of the corresponding acid;

(d) (for Ex.204): methyl 4-bromomethyl-3-chlorobenzoate, obtained as an oil by bromination of methyl 3-chloro-4-methylbenzoate.

(e) (for Ex.205): methyl 4-bromomethyl-3,5-dimethoxybenzoate, obtained in 85% yield as a solid, m.p. 117°-118° C. [recrystallised from ether/petroleum ether (40°-60° C. b.p.)], by N-bromosuccinimide bromination of methyl 3,5-dimethoxy-5-methylbenzoate, using a similar procedure to that described in part (e) of Example 200, and methyl 3,5-dimethoxy-5-methylbenzoate being obtained in 71% yield as a solid, m.p. 98°-99° C., by reaction of 3,5-dihydroxy-4-methylbenzoic with dimethyl sulphate and potassium carbonate in boiling acetone for 16 hours;

(f) (for Ex.206): methyl 4-bromomethyl-3-methylbenzoate was obtained as follows:

1.36 g. of triphenylphosphine was added in portions during 35 minutes to a solution of 722 mg. methyl 4-hydroxymethyl-3-methylbenzoate and 1.72 g. of carbon tetrabromide in 10 ml. of methylene chloride at 0° C. After a further 40 minutes an extra 118 mg. of triphenylphosphine was added to the stirred mixture. After a further 30 minutes the reaction mixture was absorbed onto silica gel and the solvent evaporated. The residue was added to the top of a column of silica gel and chromatography carried out using 60:40 v/v methylene chloride in hexane as eluant. There was thus obtained 0.914 g. (94%) of methyl 4-bromomethyl-3-methylbenzoate as an oil, partial NMR: 2.45 (s,3H,CH$_3$), 3.90 (s,3H,O.CH$_3$), 4.50 (s,2H,CH$_2$Br).

EXAMPLES 207–208

Using a similar procedure to that described in Example 23 the following esters of formula I were obtained:

(Example 207): ethyl 6-[6-(2-ethylhexanamido)indol-1-yl]4(E)-hexenoate in 40% yield as a white solid, m.p. 65°–66° C. (after purification by flash chromatography on silica gel using 1:20 v/v ethyl acetate in toluene as the eluate), by reaction of ethyl 6-bromo-4(E)-hexenoate with 6-(2-ethylhexanamido)indole;

(Example 208): methyl 4-(1-[6-(2-cyclopentylacetamido)indol-1-yl]ethyl)benzoate in 30% yield as a solid, partial NMR (d$^6$-DMSO]: 1.88 (d,3H,CH$_3$), 3.81 (s,3H,OCH$_3$), 5.75 (q,1H,CH), by reaction of methyl 4-(1-bromoethyl)benzoate with 6-(2-cyclopentylacetamido)indole.

Methyl 4-(1-bromoethyl)benzoate was obtained as follows:

(a) 2M Methanolic hydrochloric acid was added in portions to a stirred suspension of 3.6 g. of methyl 4-acetylbenzoate (obtained as a solid, m.p. 90°–92° C., by conventional esterification of the corresponding acid) and 1.4 g. of sodium cyanoborohydride in methanol containing a single crystal of the indicator methyl orange, so that a red color persisted. After 4 hours a further 173 mg. of sodium cyanoborohydride was added and the red colour again maintained by addition of 2M methanolic hydrochloric acid.

One hour after the final addition of reagents the solvents were evaporated and the residue was dissolved in water. The solution obtained was extracted with ether. The extracts were then dried (Na$_2$SO$_4$) and evaporated. The residue was purified by chromatography on silica using 3:97 v/v ether and chloroform as eluant to give 2.9 g. (80%) methyl 4-(1-hydroxyethyl)benzoate as a yellow oil; partial NMR: 1.50 (d,3H,CH$_3$), 3.91 (s,3H, OCH$_3$), 4.94 (q, 1H,CH.OH).

(b) A solution of 1.47 g. of methyl 4-(1-hydroxyethyl)benzoate and 3.61 g. carbon tetrabromide in 25 ml. methylene chloride was treated with 2.70 g. of triphenylphosphine. After 1 hour the solvent was evaporated and the residue was purified by chromatography on silica gel, using methylene chloride in hexane as the eluent, to give 1.52 g. (67%) of methyl 4-(1-bromoethyl)benzoate as an oil; partial NMR: 2.04 (d, 3H,CH$_3$), 3.91 (s,3H,OCH$_3$), 5.19 (q,1H,CH.Br).

EXAMPLES 209–238

Using a similar hydrolysis procedure to that described in Example 34, the following carboxylic acids of formula 5 may be obtained by hydrolysis:

| Ex. | Re | m.p. (°C.) | Yield (%) |
|---|---|---|---|
| 209 | cyclohexylmethyl | 252–253 | 67 |
| 210 | 1-cyclohexylpropyl | 277–278 | 66 |
| 211 | 1-phenylpropyl+ | 230–231 | 17 |
| 212 | 1-phenylpropyl++ | 230–231 | 30 |
| 213 | 1-methyl-1-phenylethyl | 209–210 | 12 |
| 214 | 1-phenyl-cyclopentyl | 145–147 | 54 |
| 215 | alpha-methoxybenzyl | 193–195 | 98 |
| 216 | alpha-cyclopentylbenzyl | 236–237(d) | 39 |
| 217 | 1-cyclopentylbutyl | 268–269 | 63 |

+from R(−)-2-phenylbutyric acid
++from S(+)-2-phenylbutyric acid

Similarly, the following carboxylic acids of formula 15 (R=H) were obtained by hydrolysis of the corresponding methyl esters:

| Ex. | Re.X | Ra | Rc | m.p. (°C.) | Yield % |
|---|---|---|---|---|---|
| 218 | isopropyloxy | H | H | 235–236+ | 58 |
| 219 | tetrahydrofuran-3-yloxy | H | H | 214–215 | 36 |
| 220 | 1-cyclohexen-4-yloxy | H | H | 236–237 | 43 |
| 221 | cyclopentyloxy | Cl | H | 234–235+ | 12 |
| 222 | cyclopentyloxy | CO.CH$_3$ | H | 262–263 | 36 |
| 223 | cyclopentylmethyl | H | Br | 237–238 | 63 |
| 224 | cyclopentylmethyl | Cl | H | 263–264 (d) | 67 |
| 225 | cyclopentylmethyl | CO.C$_3$H$_7$ | H | 237–238 | 69 |

+isolated as a partial hydrate.

Similarly, the following carboxylic acids of formula 12 (R$^1$=H) were obtained by hydrolysis of the corresponding methyl esters:

| Ex. | Rd | G$^2$ (and location on Q) | m.p. (°C.) | Yield (%) |
|---|---|---|---|---|
| 226 | 2-OCH$_3$ | direct link (3) | 200–201 | 64 |
| 227 | 4-OCH$_3$ | direct link (3) | 171–174 | 69 |
| 228 | 3-OCH$_3$ | direct link (4) | 189–190 | 69 |
| 229 | 2-Cl | direct link (4) | 222–232 (d) | 45 |
| 230 | 2,6-(OCH$_3$)$_2$ | direct link (4) | 274–275 (d) | 83 |
| 231 | 2-CH$_3$ | direct link (4) | 239–240 | 91 |

Similarly, the following carboxylic acids of formula I were obtained by hydrolysis of their corresponding methyl esters (Ex.238 uses the ethyl ester):

(Example 232): 4-[6-(2-cyclopentylacetamido)indolin-1-ylmethyl]-3-methoxybenzoic acid in 14% yield as a solid, m.p. 212°–213° C.;

(Example 233): 4-[5-(N-isobutyl)carbamoylindol-1-ylmethyl]-3-methoxybenzoic acid, in 32% yield as a hemihydrate, m.p. 157°–158° C.;

(Example 234): 4-[6-(N-cyclopentylmethyl)carbamoylindol-1-ylmethyl]-3-methoxybenzoic acid, in 50% yield as a solid, m.p. 245°–246° C.;

(Example 235): 4-[5-(N-pentyl)carbamoylindol-1-ylmethyl]-3-methoxybenzoic acid, in 86% yield as a solid, m.p. 142°–143° C.;

(Example 236): 4-[1-[2-cyclopentylacetamido]indol-1-yl)ethyl]benzoic acid, in 56% yield as a solid, m.p. 216°–217.5° C.;

(Example 237): 7-[6-(2-ethylhexanamido)indol-1-ylmethyl] benzo[b]furan-4-carboxylic acid, in 60% yield as a solid, m.p. 249°–251° C.; and (Example 238): 6-[6-(2-ethylhexanamido)indol-1-yl]-4(E)-hexenoic acid, in 89% yield as a solid, m.p. 113°–114° C.

EXAMPLE 239

Using a similar procedure to that described in Ex.90, but starting from cyclopentanethiol and t-butyl 4-(6-aminoindol-1-ylmethyl)-3-methoxybenzoate, there was obtained t-butyl 4-[6-(cyclopentylthiolocarbonyl-)aminoindol-1-ylmethyl]-3-methoxybenzoate in 38% yield as a white foam; partial NMR: 1.5 (s,9H, C(CH$_3$)$_3$), 1.6 (m, 6H,(CH$_2$)$_3$), 2.0 (m, 2H,—CH$_2$—), 3.6 (br,1H,CHS), 3.9 (s,3H,OCH$_3$), 5.3 (s,2H,NCH$_2$), 6.4 (d,1H,H$^3$-indole), 6.6 (d,1H,aromatic), 7.0 (d,1H,aromatic) 7.3–7.4 (m,4H,aromatic), 7.6 (br s,1H,H$^7$-indole), 10.0 (br s,1H,NH).

EXAMPLES 240–241

Using a similar procedure to that described in Example 172, the following acids of formula I were obtained from the corresponding t-butyl esters:

(Example 240): 4-[6-(cyclopentylthiolocarbonyl) aminoindol-1-ylmethyl]-3-methoxybenzoic acid, in 68% yield as a solid, m.p. 228°–230°C. (d); and (Example 241): 4-(3-[2-methoxycarbonylvinyl]-6-[2-ethylhexanamido]indol-1-ylmethyl)-3-methoxybenzoic acid, in 54% yield as a solid, m.p. 242°–243° C.

EXAMPLES 242–243

Using a similar procedure to that described in Example 67, the following tetrazole derivatives of formula I were obtained:

(Example 242): 6-(2-phenylbutanamido)-1-(6-[1-(H)tetrazol-5-yl]hexyl)indole, in 45% yield as a solid, m.p. 163.5°–165° C., starting from 1-(6-cyanohexyl)-6-(2-phenylbutanamido)indole, itself obtained as a solid, m.p. 105°–106° C. by sodium hydride alkylation of 6-(2-phenylbutanamido)indole with 7-bromoheptanonitrile using similar conditions to those described in Example 23; and (Example 243): 6-(2-ethylhexanamido)-1-(6-[1(H)-tetrazol-5-yl]hexyl)indole, in 58% yield as a partial hydrate, m.p. 149°–150° C., starting from 1-(6-cyanohexyl)-6-(2-ethylhexanamido)indole, itself obtained as a solid, m.p. 98°–99° C. by sodium hydride alkylation of 6-(2-ethylhexanamido)indole with 7-bromoheptanonitrile using similar conditions to those described in Example 23.

EXAMPLES 244–248

Using a similar procedure to that described in Example 157, the following tetrazole derivatives of formula I were obtained:

(Example 244): 6-[N'-(1-phenylethyl)ureido]-1-[6-(1-[H]tetrazol-5-yl)hexyl]indole, in 20% yield as a solid, m.p. 114°–116° C. (recrystallised from aqueous acetonitrile) using 6-amino-1-[6-(1[H]-tetrazol-5-yl)hexyl]indole and S(—)-alpha-methylbenzyl isocyanate;

(Example 245): 6-[N'-(1-phenylethyl)ureido]-1-[6-(1[H]tetrazol-5-yl)hexyl]indole, in 10% yield as a solid, m.p. 114°–116° C. (recrystallised from aqueous acetonitrile) using 6-amino-1-[6-(1[H]-tetrazol-5-yl) hexyl]indole and R(+)-alpha-methylbenzyl isocyanate;

(Example 246): 6-(N-cyclopentyloxycarbonylamino)-1-(8-[1(H)-tetrazol-5-yl]octyl)indol, in 23% yield as a solid, m.p. 138°–140° C., using cyclopentyl chloroformate and 6-amino-1-(8-[1(H)-tetrazol-5-yl]octyl)indole, itself obtained by alkylation of 6-nitroindole with 8-bromo-octanonitrile followed by catalytic reduction, using an analogous procedure to that for V in Example 157.

(Example 247): 6-(N-butoxycarbonylamino)-1-(8-[1(H)-tetrazol-5-yl]octyl)indol, in 37% yield as a solid, m.p. 122°–123° C., using butyl chloroformate and 6-amino-1-(8-[1(H)-tetrazol-5-yl]octyl)indole; and (Example 248): 6-(N-cyclopentyloxycarbonylamino)-1-(4-[1(H)-tetrazol-5-yl]butyl)indole, in 54% yield as a solid, m.p. 163°–165° C., using cyclopentyl chloroformate. and 6-amino-1-(4-[1(H)-tetrazol-5-yl]-butyl)indole, itself obtained in an analogous manner to 6-amino-1-(8-[1-(H)-tetrazol-5-yl]octyl)indole starting initially from 6-nitroindole and 4-bromobutyronitrile.

EXAMPLE 249

Using a similar procedure to that described in Example 73, 6-(2-cyclopentylacetamido)-1-(4-[(1H)tetrazol-5-ylthio]-2E-butenyl)indole was obtained in 40% yield as a white solid, m.p. 134°–135° C., starting from 1-(4-bromo-2-butenyl)-6-(2-cyclopentylacetamido)indole, itself obtained in 12% yield by sodium hydride alkylation of 6-(2-cyclopentylacetamido)indole with 1,4-dibromo-2-butene using similar reaction conditions to those described in Example 23.

EXAMPLE 250

Using an analogous procedure to that described in Example 9, but starting from 6-amino-1-(6-[1(H)tetrazol-5-yl]hexyl)indole and 3-cyclopentylpropionic acid, there was obtained 6-(3-cyclopentylpropionamido)1-(6-[1(H)-tetrazol-5-yl]hexyl)indole in 41% yield, m.p. 143°–145° C.

EXAMPLES 251–254

To a suspension of 340 mg. of ethyl 5-(4-[6-(N-butoxycarbonylamino)indol-1-ylmethyl]-3-methoxyphenyl)-3(H)-tetrazole-3-acetate in 5 ml. of 1M sodium hydroxide was added 5 ml. of ethanol. After 1.5 hours the reaction was diluted with water and a 2:3 v/v mixture of ethyl acetate/hexane, acidified (6M HCl) and extracted twice with ethyl acetate. The combined extracts were washed with brine, dried (MgSO$_4$) and evaporated. The residue was chromatographed on 16 g. of silica gel (octadecylsilane treated) using a methanol/phosphate buffer gradient (50/50 —60/40 v/v) as eluent. Acidification (1M HCl) of the appropriate fractions gave 240 mg. (75%) of 5(4-[6-butoxycarbonyl)aminoindole-1-ylmethyl]-3-methoxyphenyl)-3(H)-tetrazole-3-acetic acid (Example 251), as a white solid, m.p. 92°–95° C.; microanalysis, found: C. 59.92; H,5.35; N,17.33%; C$_{24}$H$_{26}$N$_6$O$_5$ requires: C, 60.25; H,5.47; N,17.56%.

Using a similar procedure, the following carboxylic acids of formula I were obtained by hydrolysis of the corresponding methyl or ethyl esters:

(Example 252): 5-(4-[6-(butoxycarbonyl)aminoindol-1-ylmethyl]-3-methoxyphenyl)-1(H)-tetrazole-1-acetic acid, isolated in 40% yield as a solid; microanalysis, found C, 60.5%, H,5.49; N, 17.47%, C$_{24}$H$_{26}$N$_6$O$_5$ requires: C, 60.25; H, 5.47; N,17.56%;

(Example 253) o-[5-(4-[6-(N-butoxycabonylamino)indol-1-ylmethyl]-3-methoxyphenyl)-3(H)-tetrazol-3-ylmethyl]-benzoic acid, isolated in 63% yield as a solid; microanalysis, found: C,62.64; H,5.26; N,14.36%; C$_{30}$H$_{30}$N$_6$O$_5$.H$_2$O requires: C,62.94; H,5.59; N14.69%

Example 254) o-[5-(4-[6-(N-butoxycarbonylamino)indol-1-ylmethyl]-3-methoxyphenyl)-1-(H)-tetrazol-1-ylmethyl]benzoic acid, isolated in 48% yield as a solid;

microanalysis, found: C,64.85; H,5.57; N,14.97%; $C_{30}H_{30}N_6O_5$ requires: C,64,97; H,5.45; N,15.4%.

The starting esters were obtained as follows:

(a) (For Examples 151,252);

To a suspension of 500 mg. 6-(butoxycarbonyl)amino-1-(2-methoxy-4-[2(H)-tetrazol-5-yl]benzyl)indole, 67 mg. potassium iodide, and 167 mg. potassium carbonate in 12 ml. of 2-butanone was added 0.14 ml. ethyl bromoacetate. The mixture was heated under reflux for 3 hours. Solid was removed by filtration and the filtrate was evaporated. The residue was purified by chromatography on 35 g. silica gel using an ethyl acetate/toluene gradient (1:15-1:10 v/v) as eluent. There was thus obtained 348 mg. (57%) of ethyl 5-(4-[6-(butoxycarbonyl)aminoindol-1-ylmethyl]-3(H)-tetrazole-3-acetate as a solid, m.p. 46°-48° C.; partial NMR ($d_6$-DMSO): 1.21 (t,3H,$OCH_2CH_3$), 4.00 (s,3H,$OCH_3$), 4.10 (q,2H,$OCH_2CH_3$), 5.33 (s,2H,benzylic $CH_2$), 5.86 (s,2H,$CH_2CH_2$); and 77 mg. (12%) of ethyl 5-(4-[6-(butoxycarbonyl)aminoindol-1-ylmethyl]-3-methoxyphenyl)-1(H)-tetrazole-1-acetate as an oil; partial NMR ($d_6$DMSO): 1.04 (t,3H, $OCH_2CH_3$), 3.96 (s,3H,$OCH_3$), 4.06 (q,2H,$OCH_2CH_3$), 5.35 (s,2H,benzylic $CH_2$) (s, 2H,$CH_2CO_2$).

(b) (For Examples 253,254):

Using a similar procedure to that described in (a) above, but using methyl 2-bromomethylbenzoate in place of ethyl bromoacetate, there were obtained methyl 0-[4-(4-[6-(butoxycarbonyl)aminoindol-1-ylmethyl]-3-methoxyphenyl)-3(H)-tetrazol-3-ylmethyl]benzoate isolated in 76% yield as a solid, m.p. 55°-58° C.; partial NMR ($d^6$-DMSO): 3.81 (s,3H,$CO_2CH_3$), 3.98 (s,3H, $OCH_3$), 5.32 (s,2H, indole $CH_2$), 6.28 (s,2H,tetrazole $CH_2$); and methyl-o-[5-(4-[6-butoxycarbonyl)aminoindol-1-ylmethyl]-3-methoxyphenyl)-1(H)-tetrazol-1-ylmethyl]benzoate isolated in 9% yield as an oil; partial NMR ($d_6$DMSO): 3.66 (s,3H,$CO_2CH_3$), 3.88 (s,3H,$OCH_3$), 5.33 (s,2H,indole $CH_2$); 6.03 (s,2H,tetrazole $CH_2$).

EXAMPLE 255

99 mg. Sodium hydride (50% w/w dispersion in mineral oil) was washed twice with hexane and suspended in 1 m. dry dimethylformamide (DMF). The suspension was stirred and a solution of 355 mg. benzenesulphonamide in 1 ml. DMF was added. The mixture was stirred for 1 hour until effervescence had stopped. A solution of 253 mg. 4-[6-(2-ethylhexanamido)indol-1-ylmethyl]-3-methoxybenzoic N,N-diphenylcarbamic anhydride in 0.5 ml. DMF was added. The mixture was stirred for a further 1 hour and poured into 20 ml. water. The aqueous mixture was acidified to pH6 with acetic acid, and extracted with ethyl acetate. The extracts were washed with water, then with saturated brine, dried ($MgSO_4$) and evaporated. The resultant residue was purified by flash chromatography (using 8% v/v ethyl acetate in toluene containing 1% v/v acetic acid), followed by recrystallisation [from ethyl acetate/petroleum ether (b.p. 60°-80° C.)]to give 130 mg. (57%) of N-(4-[6-(2-ethylhexanamido)indol-1-ylmethyl]-3-methoxybenzoyl)benzenesulphonamide as a white solid, m.p. 216.5°-218° C.; microanalysis, found: C,66.14; H, 6.34; N,7.13%; $C_{31}H_{35}N_3O_5S$ requires: C,66.29; H,6.28; N,7.48%.

The starting diphenylcarbamic anhydride was obtained as follows: A solution of 3.1 g. 4-[6-(2-ethylhexanamido)indol-1-ylmethyl]-3-methoxybenzoic acid and 1.0 ml. triethylamine in 30 ml. of methanol was treated with a solution of 2.5 g. N,N-diphenylcarbamoylpyridinium chloride in 30 ml. of methanol. The resultant precipitate was collected by filtration, washed with methanol, and dried under vacuum to give 3.54 g. (79%) of 4-[6-(2-ethylhexanamido)indol-1-ylmethyl]-3-methoxybenzoic N,N-diphenylcarbamic anhydride as a white solid, m.p. 159°-162° C.; microanalysis found: C, 73.77; H,6.37; N,6.67; $C_{38}H_{39}N_3O_5$ requires: C, 73.88; H,6.36; N, 6.80%.

EXAMPLES 256-257

Using a similar procedure to that described in Example 255 the following compounds of formula I were obtained:

(Example 256) N-(4-[6-(cyclopentyloxycarbonyl)-aminoindol-1-ylmethyl]-3-methoxybenzoyl)benzenesulphonamide, in 34% yield as a hemi-hydrate, m.p. 186°-188° C.; and, (Example 257) N-(4 [6-(2-phenylbutanamido)indol-1-ylmethyl-3-methoxybenzoyl)benzenesulphonamide, in 41% yield as a monohydrate, m.p. 214°-216° C.

The starting N,N-diphenylcarbamic anhydrides were prepared from the corresponding benzoic acids of formula I using an analogous procedure to that described in Example 255.

EXAMPLES 258-260

Using a similar procedure to that described in Example 255, but starting from the appropriate arylsulphonamide, there were obtained:

(Example 258): N-(4-[6-2-ethylhexanamido)indol-1-ylmethyl]-3-methoxybenzoyl)methanesulphonamide in 55% yield as a solid, m.p. 214°-215.5° C.

(Example 259) N-(4-[6-(2-ethylhexanamido)indol-1-yl-methyl]-3-methoxybenzoyl)-p-toluenesulphonamide in 48% yield as a solid, m.p. 228°-229° C.;

(Example 260): N-(4-[6-(2-ethylhexanamido)indol-1-yl-methyl]-3-methoxybenzoyl-o-toluenesulphonamide in 27% yield as a solid, m.p. 221°-222° C.

EXAMPLE 261

48 mg. Sodium hydride (50% w/w dispersion in mineral oil) was washed twice with petroleum ether (b.p. 40°-60° C.) and suspended in 2 ml. dry dimethylformamide. (DMF). The reaction vessel was flushed with nitrogen and 188 mg. benzenesulphonamide added. The mixture was stirred for 30 minutes until effervescence had stopped. A solution of 260 mg. 3-methoxy-4-[6-(2-phenylbutanamido)indazol-1-ylmethyl]benzoic N,N-diphenylcarbamic anhydride in 1 ml. DMF was then added and the mixture stirred for 30 minutes. The reaction mixture was diluted with 30 ml. ethyl acetate and washed successively with 5 ml. 1M hydrochloric acid, 5 ml. water (2×) and 5 ml. saturated brine, then dried ($MgSO_4$) and evaporated. The residue obtained was purified by flash chromatography, using 30% v/v ethyl acetate in toluene containing 1% v/v acetic acid as eluent, to give a solid which was recrystallised from ethyl acetate/petroleum ether (b.p. 60°-80° C.). There was thus obtained 161 mg. (69%) N-(4-[6-(2-phenylbutanamido)indazol-1-ylmethyl]-3-methoxybenzoyl)-benzenesulphonamide as a white solid, m.p. 140°-141° C.; microanalysis, found: C,65.94; H, 5.18; N, 9.31%; $C_{32}H_{30}N_4O_5S$ requires: C,65.95; H, 5.19; N, 9.61%.

The starting N,N-diphenylcarbamic anhydride was obtained as follows:

A mixture of 177 mg. 3-methoxy-4-[6-(2-phenyl-butanamido) indazol-1-yl-methyl]benzoic acid, 2.5 ml.

methanol and 0.4 ml. 1M sodium hydroxide solution was added to a solution of 149 mg. N,N-diphenylcarbamoylpyridinium chloride in 0.8 ml. methanol. The reaction mixture was stirred for 20 minutes and diluted with 30 ml. ethyl acetate. The mixture was then washed with 5 ml. water, then with 5 ml. brine, dried (MgSO$_4$) and evaporated to give 260 mg. of 3-methoxy-4-[6-(2-phenylbutanamido)indazol-1-ylmethyl]-benzoic N,N-diphenylcarbamic anhydride as a yellow oil, essentially pure by TLC (retention factor value=0.8 on SiO$_2$; eluent 50v/v ethyl acetate/toluene containing 2% acetic acid) and which was used without further purification or characterisation.

EXAMPLE 262

204 mg. 4-[6-(Cyclopentyloxycarbonyl)aminoindazol-1-ylmethyl]-3-methoxybenzoic acid was added to a stirred solution of 79 mg. benzenesulphonamide, 4-dimethylaminopyridine and 96 mg. 1-[3-(dimethylamino)propyl]-3-ethylcarbodiimide hydrochloride in 5 ml. of dry methylene chloride. After 15 minutes the mixture became homogeneous. It was stirred for a further 18 hours, then diluted with 20 ml. methylene chloride and washed successively with 20 ml. portions of 1M hydrochloric acid, water and saturated brine. The solution was then dried (MgSO$_4$) and evaporated to give 278 mg. of amorphous solid. This was crystallised from a mixture of methylene chloride, diethyl ether and petroleum ether (b.p. 40°-60° C.) to give 184 mg. (67%) N-(4-[6-cyclopentyloxycarbonyl)aminoindazol-1-ylmethyl]-3-methoxybenzoyl)benzenesulphonamide as a white solid, m.p. 181°-182.5° C.; microanalysis, found: C, 61.46; H, 5.17; N, 10.19%; C$_{28}$H$_{28}$N$_4$O$_6$S requires: C, 61.30; H, 5.14; N, 10.21%.

EXAMPLES 263-264

Using a similar procedure to that described in Example 262, the following sulphonamides of formula I were obtained:

(Example 163): N-(4-[6-(2-cyclopentylacetamido)indazol-1-ylmethyl]-3-methoxybenzoyl)benzenesulphonamide, isolated in 48% yield as a solid, m.p. 167°-169° C.; microanalysis, found: C,63.73; H,5.61; N,9.98%; C$_{29}$H$_{30}$N$_4$O$_5$S requires: C, 63.72H,5.53; N,10.25%;

(Example 264): N-(4-[6-(2-cyclopentylacetamido)indazol-1-ylmethyl]-3-methoxybenzoyl-o-toluenesulphonamide, isolated in 60% yield as a solid, m.p. 183.5°-185° C.; microanalysis, found: C,64.27; H,5.81; N,9.78%; C$_{30}$H$_{32}$N$_4$O$_5$S requires: C, 64.27; H,5.75; N,9.99%;

EXAMPLES 265-269

Using a similar procedure to that described in Example 262, but starting from the appropriate carboxylic acid of formula I (Z=CO$_2$H) and sulphonamide of the formula H$_2$N.SO$_2$.Rg, the following sulphonamide derivatives of formula 19 (Ra=H), ReX=cyclopentylmethyl):

| Ex. | Rg | m.p. (°C.) | Yield % |
|---|---|---|---|
| 265 | o-tolyl | 218-220 | 63 |
| 266 | 2-aminophenyl | 140-155 | 30 |
| 267 | 2-thienyl | 144-148 | 64 |
| 268 | 1-naphthyl | 144-147 | 60 |
| 269 | 6-chloro-3-pyridyl | 244-246 | 42 |

| Ex. | Rg | m.p. (°C.) | Yield % |
|---|---|---|---|
| | (d) | | |

EXAMPLES 270-276

Using a similar procedure to that described in Example 255, but starting from the appropriate sulphonamide derivatives of formula 19 (Ra=H, ReX=1-ethylpentyl) were obtained:

| Ex. | Rg | m.p. (°C.) | Yield (%) |
|---|---|---|---|
| 270 | 4-methoxyphenyl | 197-199 | 18 |
| 271 | benzyl | 212-213.5 | 73 |
| 272 | 4-chlorophenyl | 182.5-184 | 64 |
| 273 | 4-fluorophenyl | 176-178 | 65 |
| 274 | 4-nitrophenyl | 212-214 | 45 |
| 275 | isopropyl | 206-207 | 32 |
| 276 | butyl | 157-159 | 20 |

EXAMPLE 277

A solution of 8.9 g. 4-[3-acetyl-6-cyclopentyloxycarbonyl)aminoindol-1-ylmethyl]-3-methoxybenzoic acid, 2.5 g. 4-N,N-dimethylaminopyridine, 4.0 g.1-[3-dimethylamino)propyl]-3-ethylcarbodiimide hydrochloride, and 3.2 g. benzenesulfonamide in 100 ml. methylene chloride was stirred for 24 hours and then diluted with ethyl acetate. The mixture was washed successively with dilute hydrochloric acid (ca 2M), water and brine. The organic layer was dried (MgSO$_4$) and the solvent was evaporated. The residue was purified by recrystallisation from a mixture of methanol, THF and water to give 7.5 g. (64%) N-(4-[3-acetyl-6-(cyclopentyloxycarbonyl)aminoindol-1-ylmethyl]-3-methoxybenzoyl)benzenesulphonamide as a white solid, m.p. 245°-246° C. microanalysis, found: C,62.98; H,5.37; N,6.94%; C$_{31}$H$_{31}$N$_3$O$_7$S requires: C, 63.14; H,5.30; N, 7.13%.

EXAMPLES 278-288

Using a similar procedure to that described in Example 277, but starting from the appropriate 4-(indol-1-yl- or indolin-1-yl-methyl)-3-methoxybenzoic acid, the following N-benzenesulphonamide derivatives of formula 19 (Rg=phenyl, Ra=H except for Example 279 where Ra=chloro and Example 283 where Ra=2(E) (methoxycarbonyl)vinyl:

| Ex. | Re.X | m.p. (°C.) | Yield (%) |
|---|---|---|---|
| 278 | cyclopentyl | 225-226 | 52 |
| 279 | cyclopentyloxy | 199-200 | 18 |
| 280 | cyclopentylmethyl | 194-196(d)+ | 42 |
| 281 | cyclopentylamino | 227-228(d) | 50 |
| 282 | tetrahydrofur-3-yloxy | 183-184 | 25 |
| 283 | 1-ethylpentyl | 199-201 | 54 |

Note:
+ mono-hydrate (Example 284) N-(4-[6-(2-cyclopentylacetamido)indolin-1-ylmethyl]-3-methoxybenzoyl)benzenesulphonamide, in 7% yield as a solid, m.p. 136°-137° C. (dihydrate);

(Example 285): N-(4-[6-(N-cyclopentylmethylcarbamoyl)-indol-1-ylmethyl]-3-methoxybenzoyl)benzenesulphonamide, in 63% yield as a solid, m.p. 207°–208° C.

(Example 286) N-(4-[5-(N-pentylcarbamoyl)indol-1-ylmethyl]-3-methoxybenzoyl)benzenesulphonamide, in 56% yield as a solid, m.p. 223°–225° C.;

(Example 287) N-(5-[6-(N-cyclopentyloxycarbonylamino)-indol-1-ylmethyl]-2-furoyl)benzene sulphonamide, in 29% yield as a solid, m.p. 228°–229° C.; and (Example 288): N-(4-[6-(2-ethylhexanamido)indol-1-ylmethyl]-2-methoxybenzoyl)benzenesulphonamide, in 71% yield as a solid, m.p. 134°–136° C.

EXAMPLE 289

Using a similar procedure to that described in Example 255, but starting from benzenesulphinamide, there was obtained N-(4-[6-(2-ethylhexanamido)indol-1-ylmethyl]-3-methoxybenzoyl)benzenesulphinamide in 28% as a solid, m.p. 122°–126° C.; microanalysis found: C,67.61; H,6.79; N,7.39%; $C_{31}H_{35}N_3O_4S$ requires: C, 68.23; H6.46; N, 7.70%.

Benzenesulphinamide was prepared by reacting benzenesulphinyl chloride with ammonia in ether initially at −78° C. and finally at ambient temperature and was isolated in 17% yield as a solid, m.p. 112°–115° C.

EXAMPLE 290

Using a similar procedure to that described in Example 157, starting with 2-cyclopentylacetyl chloride and N-4-[6-aminoindol-1-ylmethyl]-3-methoxybenzoyl)benzenesulphonamide, there may be obtained N-(4-[6-(2-cyclopentylacetamido)indol-1-ylmethyl]-3-methoxybenzoyl)benzenesulphonamide as a solid essentially identical in physical properties to that obtained in Example 280.

The starting aminoindole derivative was obtained as follows:

(a) Nitrogen was passed through a solution containing 1.39 g. methyl 3-methoxy-4-(6-nitroindol-1-ylmethyl)benzoate in 1:1 v/v methanol and THF together with 0.86 g. lithium hydroxide monohydrate in 25 ml. water. After 1 minute the reaction mixture was sealed and stirred for 3 days. Solvent was then evaporated. The residue was diluted with water, acidified (1M hydrochloric acid) and extracted with ethyl acetate. The extracts were washed with water, then with brine and were dried (MgSO$_4$). Evaporation of solvent gave a 3-methoxy-4-[6-nitroindol-1-ylmethyl]benzoic acid in 91% yield as a solid m.p. 243°–245.5° C. which was used without further purification.

(b) A suspension of 1.22 g. nitro-acid from (a) above in 15 ml. methanol and 3.7 ml. 1M sodium hydroxide solution was treated with 1.38 g. N,N-diphenylcarbamoyl pyridinium chloride during 1 minute. 50 ml. Ethyl acetate was then added, followed by sufficient DMF to produce a homogeneous solution. This solution was washed with water, then with brine and was then dried (MgSO$_4$) and evaporated to give 3-methoxy-4-[6-nitroindol-1-ylmethyl]benzoic N,N-diphenylcarbamic anhydride as a yellow oil. This was then reacted with benzenesulphonamide using a similar procedure to that described in Example 255 to give N-(3-methoxy-4-[6-nitroindol-1-ylmethyl]benzoyl)benzene sulphonamide in 77% yield as a solid; partial NMR (d$_6$-DMSO): 3.93 (s,3H,OCH$_3$), 5.56 (s,2H,NCH$_2$).

(c) The nitro-sulphonamide derivative from (b) above was reduced using a similar procedure to that described in part (c) of Example 157 to give N-(4-[6-aminoindol-1-ylmethyl]-3-methoxybenzoyl)benzenesulphonamide in 80% yield as a solid, m.p. 151°–155° C.

EXAMPLE 291

A mixture of 306 mg. 4-6-(cyclopentyloxycarbonyl)aminoindazol-1-ylmethyl]-3-methoxybenzoic acid in 4 ml. methanol and 6 ml. methylene chloride was treated with 0.75 ml. of 1M sodium hydroxide solution. After 15 minutes the mixture was evaporated and the residue was recrystallised from ether/methylene chloride/methanol to give sodium 4-[6-cyclopentyloxycarbonyl)aminoindazol-3-methoxybenzoate in 78% yield as a solid, m.p. >280° C. (d); microanalysis, found: C,59.80; H,5.06; N,9.20%; $C_{22}H_{22}H_3O_5Na.0.5H_2O$ requires: C, 59.99; H,5.26; N,9.54%.

EXAMPLES 292-293

Using a similar procedure to that described in Example 291 but using the equivalent quantities of sodium hydroxide solution the sodium salts of N-4-[6(2-ethylhexanamido)indol-1-ylmethyl]-3-methoxybenzoylbenzenesulphonamide (i) and 6-cyclopentyloxycarbonyl)amino-1-(2-methoxy-4-[1-(H)tetrazol-5-benzyl)indazole (ii) were obtained as solids:

(i) in 93% yield, m.p. 258°–259° C.; microanalysis, found: C,63.74; H,5.93; N,7.35%; $C_{31}H_{34}N_3O_5SNa$, requires: C,63.79; H,5.87; N,7.20%; and (ii) in essentially quantititative yield (not recrystallised), m.p. 200°–210° C. (d); microanalysis, found: C, 55.91; H,5.54; N,20.76%; $C_{22}H_{22}N_7O_3Na.H_2O$ requires: C,55.81; H,5.11; N,20.70%.

EXAMPLE 294

Using a similar procedure to that described in Example 261, there was obtained N-(4-[6-butoxycarbonyl)aminoindazol-1-ylmethyl]-3-methoxybenzoyl)benzenesulphonamide in 35% yield as a solid, m.p. 153°–154° C.; microanalysis, found: C, 60.34; H,5.16; N,10.52%; $C_{27}H_{28}N_4O_6S$ requires: C, 60.42; H,5.25; N,10.44%.

EXAMPLE 295

Using a similar procedure to that described in Example 67, there was obtained 6-(2-cyclopentylacetamido)-1-(2-methoxy-4-[1(H)-tetrazol-5-yl]benzyl)-indole in 29% yield as a solid, m.p. 218°–220° C. (1/4H$_2$O), starting from 6-(2-cyclopentylacetamido)-1-(4-cyano-2-methoxybenzyl)indole itself obtained by alkylation of 6-(2-cyclopentylacetamido)indole using a similar procedure to that described in Example 67 (c).

EXAMPLES 296-297

Using a similar procedure to that described in Example 262, but starting from the appropriate carboxylic acids of formula I (Z=CO$_2$H), there were obtained:

(Example 296): N-(4-[6-(2-ethylhexanamido)indol-1-yl-methyl]-3,5-dimethoxybenzoyl)benzenesulphonamide in 39% yield as a solid, m.p. 220°–221.5° C.; microanaylsis, found: C, 65.19; H,6.65; N, 6.53%; $C_{32}H_{37}N_3O_6S$ requires: C, 64.97; H,6.30; N, 7.1%; and (Example 297): N-(4-[6-(2-ethylhexanamido)indol-1-ylmethyl]benzoyl)benzenesulphonamide in 37% yield as a solid, m.p. 166°–174° C.; microanalysis, found: C,64.16; H,6.03; N, 7.87%; $C_{30}H_{33}N_3O_4S$. 1½H$_2$O requires: C,64.49; H, 6.49; N,7.52%.

EXAMPLE 298

Using a similar procedure to that described in Example 185, methyl 4-[6-(2-cyclopentylacetamido)indazol-1-ylmethyl]-3-methoxybenzoate was obtained in 79% yield, starting from methyl 4-(6-aminoindazol-1-ylmethyl)-3-methoxybenzoate and 2-cyclopentylacetic acid and was isolated as a solid, m.p. 195°–197.5° C.; microanlysis, found: C, 68.07; H, 6.37; N,9.57%; $C_{24}H_{27}N_3O_4$ requires: C, 68.39; H,6.46; N,9.96%.

EXAMPLE 299

Using a similar hydrolysis procedure to that described in Example 34, 4-[6-(2-cyclopentylacetamido)-indazol-1-ylmethyl]-3-methoxybenzoic acid was obtained in 99% yield as a solid, m.p. 254°–256° C.; microanalysis, found: C, 67.41; H,6.37; N,10.28%; $C_{23}H_{25}N_3O_4$ requires: C, 67.79; H,6.18; N,10.31%

EXAMPLE 300

A solution of 0.16 g. 3-butyryl-6-(2-cyclopentylacetamido)indole in 0.5 ml. DMF was added to a stirred slurry of 9 mg. sodium hydride in 0.2 ml. DMF at 0°–4° C. The mixture was stirred at that temperature for 30 minutes and then treated with a solution of 0.16 g. N-(4-bromomethyl-3-methoxybenzoyl)benzenesulphonamide and 10 mg. sodium hydride in 1.5 ml. DMF. The reaction mixture was stirred at ambient temperature for 24 hours and then cooled to 0°–4° C. A further 9 mg. sodium hydride was added and stirring continued at ambient temperature for 30 minutes. The reaction mixture was again cooled to 0°–4° C. and excess sodium hydride destroyed by addition of a saturated solution of ammonium chloride. The resulting mixture was extracted with ethyl acetate. The extracts were washed successively with water and brine, then dried (MgSO4) and evaporated. The residue was recrystallised first from THF/petroleum ether (b.p. 60°–80° C.) and then from methanol/water to give 12.8 mg. (5%) N-(4-[3-butyryl-6-(2-cyclopentylacetamido)indol-1-ylmethyl]-3-methoxybenzoyl)benzenesulphoamide as a white solid, m.p. 143°–145° C.; microanalysis, found: C, 64.47; H,6.00; N, 6.41%; $C_{34}H_{37}N_3O_6S.1H_2O$ requires: C,64.44; H,6.20; N,6.63%.

The starting bytyrylindole derivative was made using an analogous procedure to that described for the acetyl indole (DD) in Example 174, but starting from 6-(2-cyclopentylacetamido)indole and N,N-dimethylbutyramide and was isolated in 99% yield as a solid; partial NMR: 1.03 (t,3H,CH3), 2.40 br s,3H,CHCH2), 2.89 (t, 2H, CO.CH2), 7.24 (dd,1H,H5-indole), 8.30 (d,1H,H2-indole), 9.90 (s,1H,NH), 11.90 (br s,1H,NH).

The starting sulphonamide derivative was obtained by light catalysed N-bromosuccinimide/benzoyl peroxide bromination using a similar prodecure to that described in part (e) of Example 200 but starting from N-(3-methoxy-4-methylbenzoyl)benzenesulphonamide. In this way N-(4-bromomethyl-3-methoxybenzoyl)benzenesulphonamide was isolated in essentially quantitative yield as a white solid, m.p. 190°–195° C. N-(3-Methoxy-4-methylbenzoyl)benzenesulphonamide was itself obtained using an analogous procedure to that described in EXAMPLE 277, but using 3-methoxy-4-methylbenzoic acid and benzenesulphonamide, and was isolated in 67% yield as a solid, m.p. 159°–160° C.

EXAMPLE 301

Using a similar procedure to that described in EXAMPLE 1, N-(7-[6-hexanamidoindol-1-yl]heptanoyl)-benzenesulphonamide was obtained in 13% yield as a solid, m.p. 97°–99° C., starting from hexanoyl chloride and N-(7-[6-aminoindol-1-yl]heptanoyl)benzenesulphonamide. The latter compound was obtained as follows:

Methyl 7-(6-nitroindol-1-yl)heptanoate was first obtained in 52% yield as a solid having a satisfactory NMR spectrum using an analogous procedure to that described for C in Example 1 (but using methyl 7-bromoheptanoate as the alkylating agent) and was then hydrolysed using similar conditions to those to give the corresponding acid. This was reacted with benzenesulphonamide and dicyclohexylcarbodiimide, using similar conditions to those described in Example 277, to give N-(7-[6-nitroindol-1-yl]heptanoyl)benzenesulphonamide as a yellow solid, m.p. 117°–121° C.; microanalysis, found: C, 58.74; H,5.44; N,9.47%; $C_{21}H_{23}N_3O_5S$ requires: C,58.73; H,5.40; N,9.78%. This 6-nitro derivative was then reduced, using similar conditions to those described in part (c) of Example 157, to give N-(7-[6-aminoindol-1-yl]heptanoyl)benzenesulphonamide in essentially quantitative yield as a solid which was used without characterisation.

EXAMPLE 302

Using similar procedure to that described in Example 157, but using cyclopentyl chloroformate and N-(7-[6-aminoindol-1-yl]heptanoyl)benzenesulphonamide, N-(7-[6-(cyclopentyloxycarbonyl)aminoindol-1-yl]heptanoyl)benzenesulphonamide was obtained in 51% yield as a solid, m.p. 74°–76° C.; microanalysis, found, C,62.74; H,6.54; N,7.84%; $C_{27}H_{33}N_3O_5S$, $\frac{1}{4}H_2O$ requires: C, 62.83; H,6.54; N,8.14%.

EXAMPLE 303

A solution of 220 mg. benzenesulphonylisocyanate in 5 ml. benzene and 6 ml. methylene chloride was combined with 221 mg. 3-(6-hexanamidoindol-1-yl)propanol. After 15 minutes, the mixture was added slowly with stirring to 75 ml. hexane. The solid which formed was collected by filtration and purified by chromatography on silica gel (using 10% v/v hexane/ethyl acetate as eluent). The non-crystalline product was dissolved in a mixture of 2 ml/ ehtanol and 4 ml. ethyl acetate. Addition of this solution to a vigorously stirred mixture of 40 ml. ether and 20 ml. hexane gave N-[1-(6-hexanamidoindol-1-yl)-propoxycarbonyl]benzenesulphonamide in 14% yield as a white solid, m.p.>130° C.(d); microanalysis, found: C, 57.61; H, 5.89; N,8.10%; $C_{24}H_{29}N_3O_5S.1.40 H_2O$ requires: C, 58.02; H,6.45; N, 8.46%.

The starting material was obtained as follows:

(a) A solution of 4.61 g. 3-bromopropanol in 150 ml. methylene chloride at 0° C. was treated with 5.1 ml. dihydropropyran followed by 55 mg. p-toluenesulphonic acid and then warmed to room temperature. After one hour, phosphate buffer (pH: 7.5) was added to the mixture. The organic layer was washed with brine, dried (Na2SO4) and evaporated. The yellow oil obtained was purified by chromatography on triethylamine-treated silica gel using a gradient solvent system (pure hexane-50% v/v ethyl ether/hexane) as eluent to give 2-(3-bromopropoxy)tetrahydro-2H-pyran in 69% yield as an oil, having a satisfactory NMR spectrum.

(b) 6-Hexanamidoindole was alkylated with 2-(3-bromopropoxy)tetrahyro-2H-pryan using a similar procedure to that described in Example 23 to give 2-[3-(6-hexanamidoindol-1yl)propoxy]tetrahydro-2H-pyran in 81% yield as an oil, which was used without characterisation.

(c) A solution of 656 mg. of the pyran derivative from (b) above in 10 ml. methanol and 2 ml. water was treated with 10 mg. p-toluenesulphonic acid. After 72 hours, the mixture was treated with phosphate buffer (pH: 7.5) and the methanol evaporated. The residue was extracted with ethyl acetate. The extracts were washed with sodium bicarbonate solution followed by brine and were then dried (MgSO$_4$) and evaporate. The residual yellow oil was purified by chromatography on silica gel using a gradient solvent system (17% v/v ether/methylene chloride to 50% v/v ether/methylene chloride as eluent, to give 3-(6-hexanamidoindol-1-yl)propanol in 77% yield as a white solid, m.p. 87°-88° C.

EXAMPLE 304

Using a similar hydrolysis procedure to that described in Example 34, there was obtained N-(4-[3-(2[E]-carboxyvinyl)-6-(2-ehtylhexanamido)indol-1-ylmethyl]-3-methoxybenzoyl)benzene sulphonamide in 52% yield as a solid, m.p. 200°-201° C., starting from the corresponding methyl ester (Example 283).

EXAMPLE 305

Using a similar procedure to that described in Example 277, there was obtained N-(4-[6-(cyclopentylthiolocarbonyl)aminoindol-1-ylmethyl]-3-methoxybenzoyl)benzenesulphonamide in 38yield as a solid, m.p. 199°-200° C., starting rom 4-[6-(cyclopentylthiolocarbonyl)aminoindol-1-ylmethyl]-3-methoxybenzoic acid and benzenesulphonamide.

EXAMPLE 306

Methyl 4-[(6-aminoindazol-1-ylmethol]-3-methoxybenzoate (L) used as a starting material in e.g. Example 74 may also be obtained as follows:

A mixture of 2.19 g. of sodium 3-chloro-6-nitroindazolide in 50 ml. methanol was stirred with 2.85 g methyl 3-methoxy-4-bromomethylbenzoate for 2 hours. After addition of 150 ml. water the resultant precipitate was collected and recrystallised from ethyl acetate to give methyl 4-[3-chloro-6-nitroindazol-1-yl-methyl]-3-methoxybenzoate in 70% yield as a solid, m.p. 167°-168° C. A mixture of 1.25 g. of this solid was hydrogenated in the presence of 385 mg. 5% w/w palladium on calcium carbonate in 20 ml. ethyl acetate and 20 ml. methanol for 3 hours at a pressure of 1.1 bar. The catalyst was removed by filtration through diatomaceous earth. The filtrate was concentrated to low volume in vacuo and the residue (ca 3 ml.) was diluted with ether and petroleum ether (b.p. 40°-60° C.) and cooled to −20° C. The precipitated solid was collected and dried at 80° C. to give the ester L in 90% yield, m.p. 131°-131.5° C.

EXAMPLE 307

The following illustrate representative pharmaceutical dosages forms which may be used for the therapeutic or prophylacteic administration of an acidic compound of formula I (i.e. Z is an acidic group as defined herinbefore) or of a pharmaceutically acceptable salt thereof (hereinafter referred to as compound X):

| (i) Tablet 1 | mg/tablet |
|---|---|
| Compound X | 100 |
| Lactose Ph.Eur. | 182.75 |
| AcDiSol | 12.0 |
| Maize starch paste (5% w/v paste) | 2.25 |
| Magnesium stearate | 3.0 |
| (ii) Tablet 2 | mg/tablet |
| Compound X | 20 |
| Microcrystalline cellulose | 420 |
| Polyvinylpyrrolidone (5% w/v paste) | 14.0 |
| Starch (pregelatinised) | 43.0 |
| Magnesium stearate | 3.0 |
| (iii) Capsule | mg/capsule |
| Compound X | 10 mg. |
| Lactose Ph.Eur. | 488.5 |
| Magnesium stearate | 1.5 |
| (iv) Injection 1 | (10 mg./ml.) |
| Compound X (free acid form) | 1.0% w/v |
| Sodium phosphate BP | 3.6% w/v |
| 0.1M Sodium hydroxide solution | 15.0% w/v |
| Water for injection . . . to 100% | |
| (v) Injection 2 (buffered to pH 6) | (1 mg./ml) |
| Compound X (free acid form) | 0.1% w/v |
| Sodium phosphate BP | 2.26% w/v |
| Citric acid | 0.38% w/v |
| Polyethylene glycol 400 | 3.5% w/v |
| (vi) Aerosol | mg./ml. |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

It will be appreciated that the above pharmaceutical compositions may be varied according to well known pharmaceutical techniques to accommodate differing amounts and types of active ingredient X. The aerosol (vi) may be used in conjunction with a standard, metered dose aerosol dispenser.

FORMULAE
(Description)

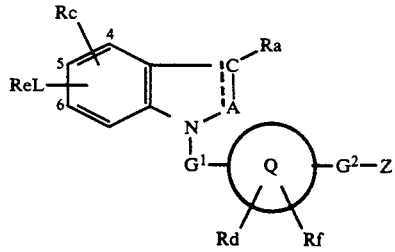

I

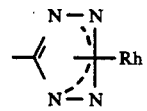

II

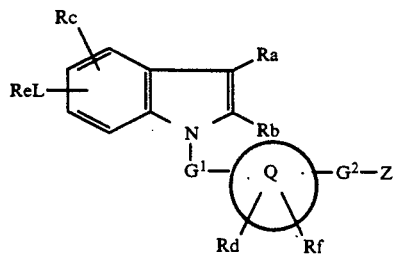

III

-continued
FORMULAE
(Description)
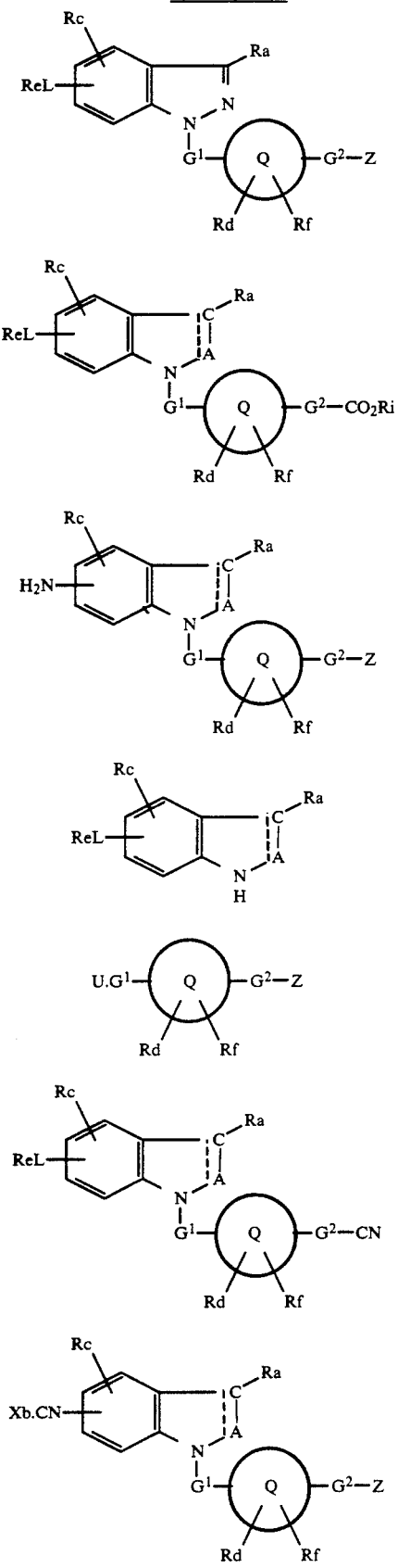
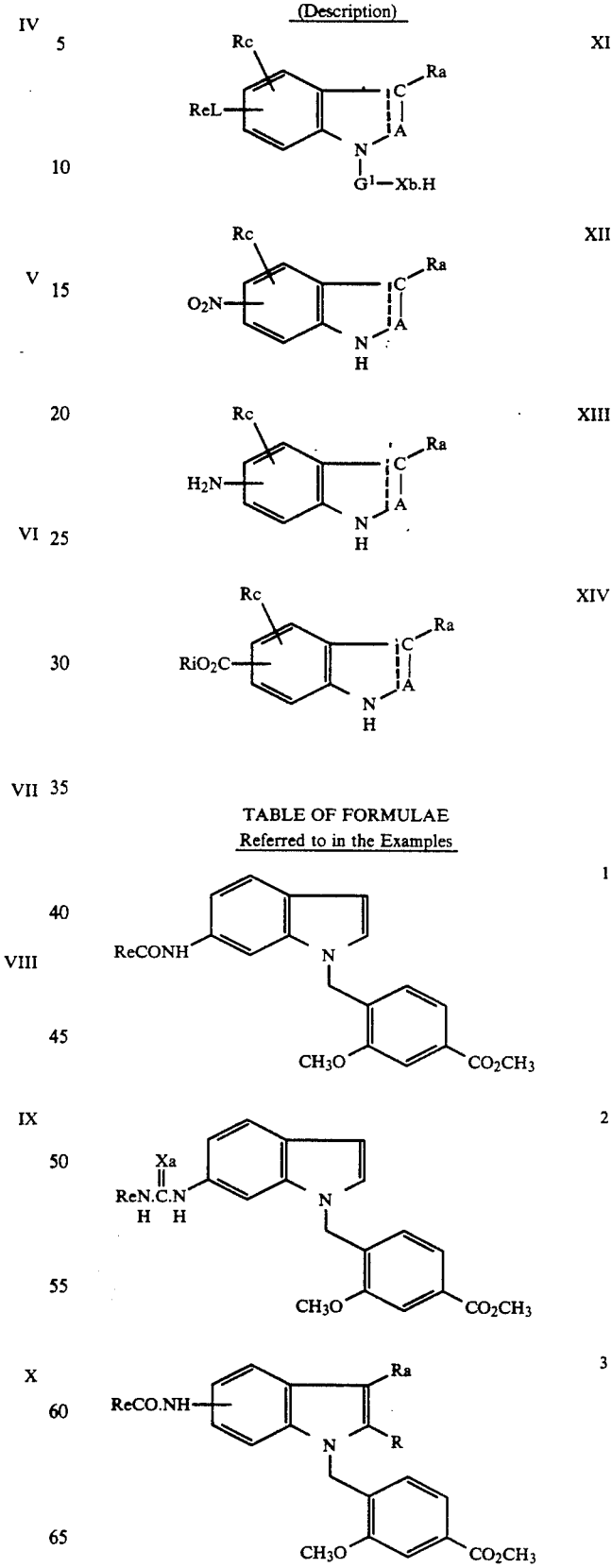
TABLE OF FORMULAE
Referred to in the Examples
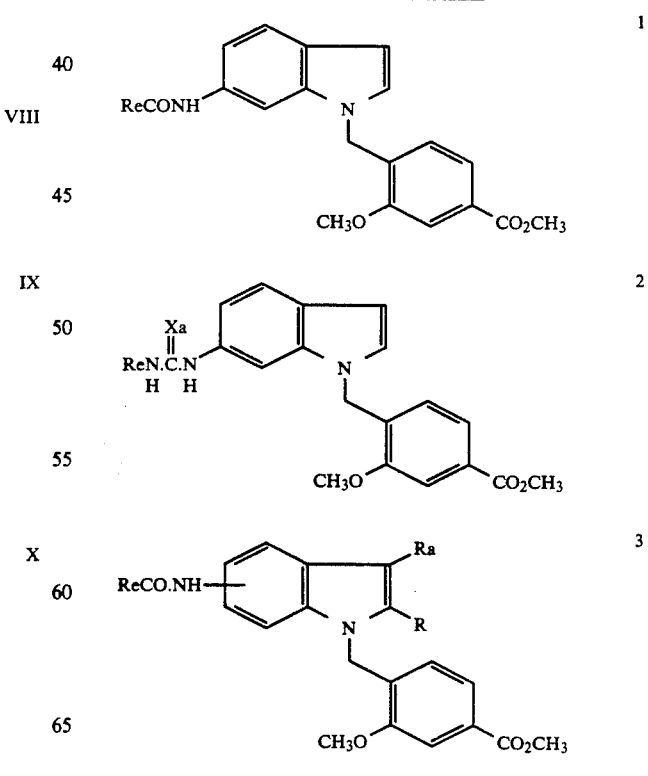

-continued
TABLE OF FORMULAE
Referred to in the Examples
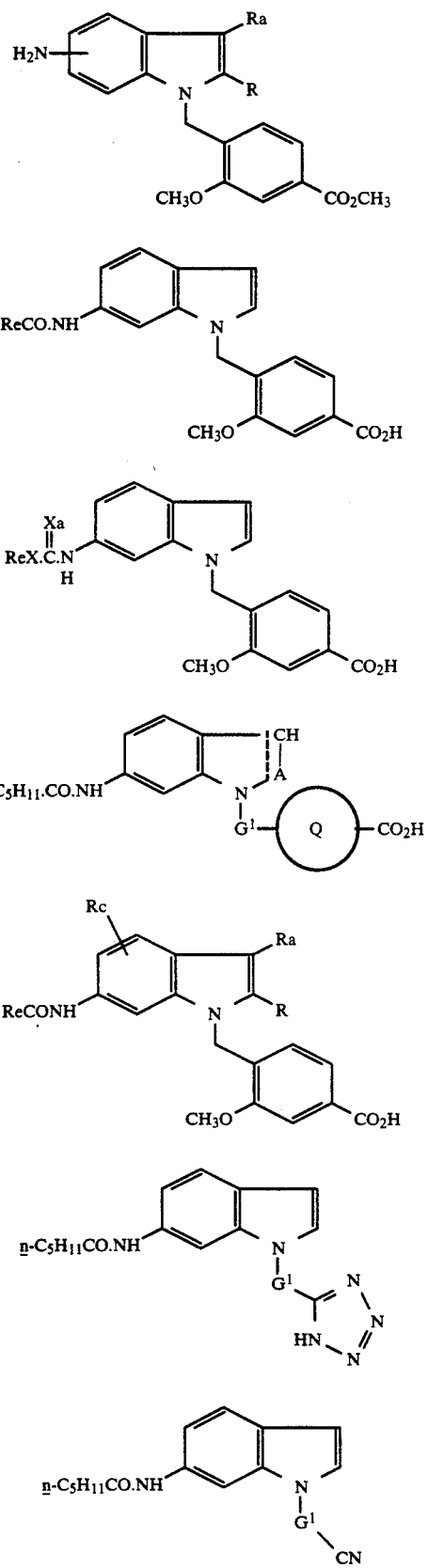
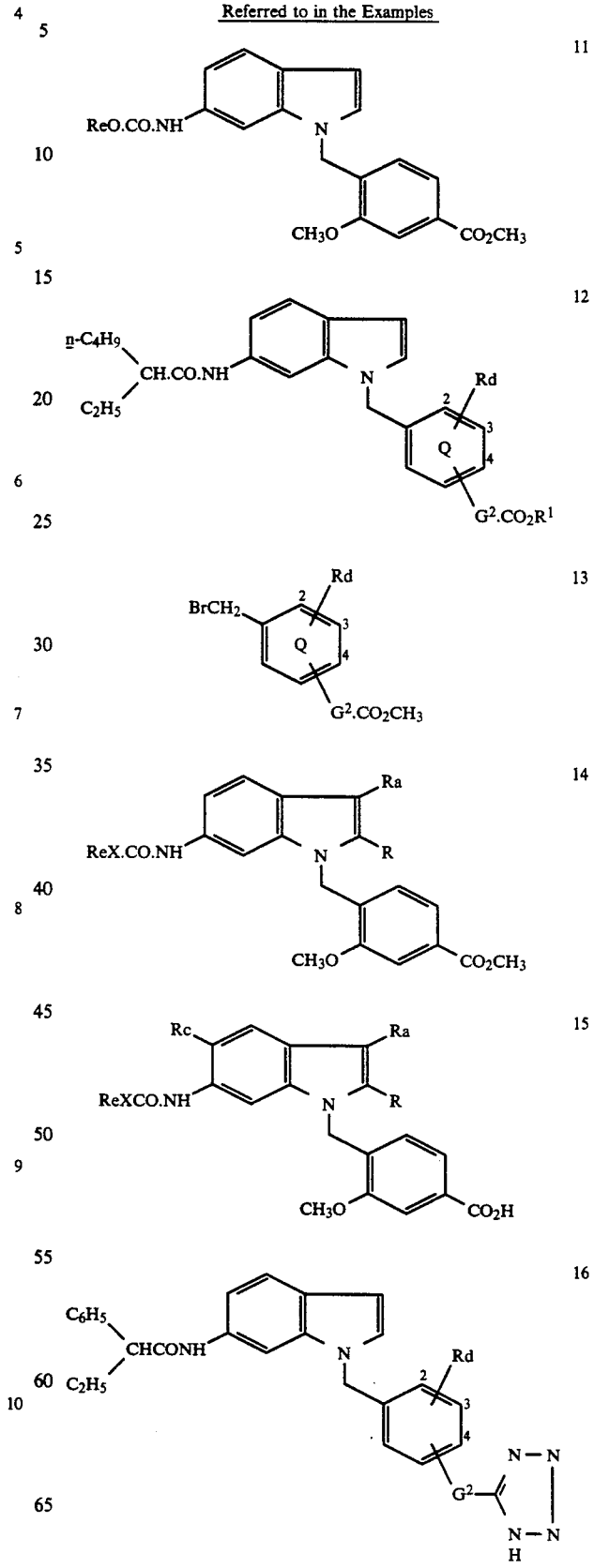

-continued
TABLE OF FORMULAE
Referred to in the Examples

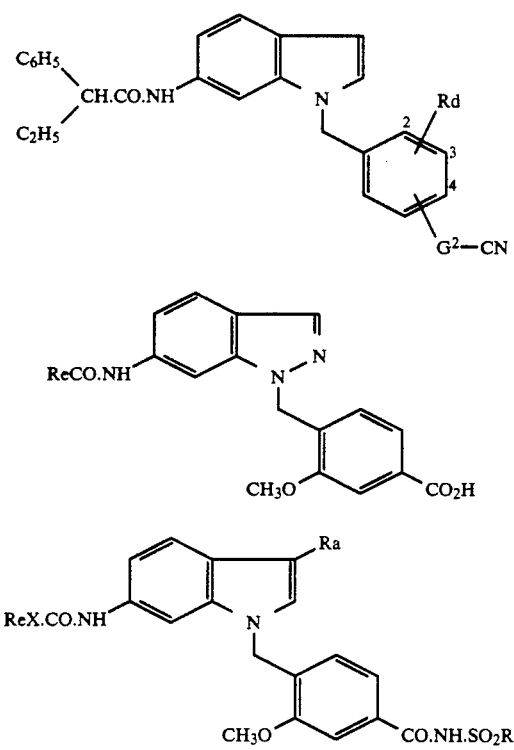

What is claimed is:
1. An amidic compound of the formula I

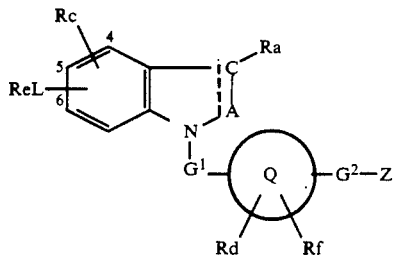

wherein:
the group A═CRa is selected from diradicals of the formulae —CRb═Cra— and —CHRb.CHRa— in which Ra is hydrogen, methyl, halogeno, (2-6C)alkanoyl, (2-6C)alkenyl or (2-6C)alkyl, the latter two of which may optionally bear a carboxy or {(1-4C)alkoxy}carbonyl substituent, and Rb is hydrogen or (1-4C)alkyl; or Ra and Rb together form tetramethylene optionally bearing 1 or 2 (1-4C)alkyl substituents and optionally containing 1 or 2 unsaturated linkages;

Rc, Rd and Rf are independently selected from hydrogen, halogeno, (1-4C)alkyl and (1-4C)alkoxy;

the group Re.L stands for an amidic radical of the formula: Re.X.CO.NH—, Re.X.CS.NH— or Re.NH.CO— attached at position 4, 5, or 6 of the benzenoid moiety shown in formula I, and in which Re is (2-10C)alkyl optionally containing 1 or more fluorine substituents, or is (3-10C)alkenyl or (3-10C)alkynyl; or Re is phenyl, phenyl-(1-6C)alkyl or thienyl-(1-6C)alkyl, in which the (1-6C)alkyl moiety may optionally bear a (1-4C)alkoxy, (3-6C)cycloalkyl or phenyl substituent and in which a phenyl or thienyl moiety may optionally bear 1 or 2 substituents selected from halogeno, (1-4C)alkyl, (1-4C)alkoxy and trifluoromethyl; or Re is (3-8C)cycloalkyl, (3-8C)cycloalkyl-(1-6C)alkyl, tetrahydrofuryl or tetrahydropyranyl, the cyclic moiety of any of which optionally may contain one unsaturated linkage or bear 1 or 2 (1-4C)alkyl substituents or a phenyl substituent, the latter itself optionally bearing a halogeno, (1-4C)alkyl, (1-4C)alkoxy or trifluoromethyl substituent; X is oxy, thio, imino or a direct link to Re;

Q is a direct link to $G^1$, or is oxy, thio, m-phenylene, p-phenylene, 2,5-furandiyl, 2,5-thiophenediyl or 4,7-benzo[b]furandiyl;

$G^1$ is (1-8C)alkylene or (2-6C)alkenylene;

$G^2$ is methylene, vinylene or a direct link to Z; and

Z is an acidic group selected from the group consisting of carboxy, an acylsulphonamide residue of the formula —CO.NH.SO$_n$Rg and a tetrazolyl residue of the formula II

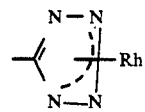

in which n is the integer 1 or 2, Rg is (1-6C)alkyl, phenyl or naphthyl, furyl, thienyl, furylmethyl, thienylmethyl or aryl-(1-4C)alkyl, in any of which the aromatic or heteroaromatic moiety optionally may bear 1 or 2 substituents independently selected from halogeno, (1-4C)alkyl, (1-4C)alkoxy, trifluoromethyl, nitro and amino; and Rh is hydrogen, carboxy-(1-3C)alkyl or (carboxyphenyl)methyl; provided that $G^1$, Q and $G^2$ taken together contain at least 3 carbon atoms and that $G^2$ is methylene or vinylene when Q is oxy or thio and Z is carboxy; or a pharmaceutically acceptable salt thereof.

2. A compound as claimed in claim 1 wherein Ra is hydrogen, methyl, chloro, bromo, acetyl, propionyl or butyryl; or is ethyl, propyl, butyl, vinyl, allyl or 1-propenyl, optionally bearing a carboxy, methoxycarbonyl or ethoxycarbonyl substituent; and Rb when present is hydrogen, methyl or ethyl; or Ra and Rb together form 1-butenylene or 1,3-butadienylene, optionally bearing 1 to 2 methyl or ethyl substituents; Rc, Rd and Rf are independently selected from hydrogen, fluoro, chloro, bromo, methyl, ethyl, methoxy and ethoxy; Re is ethyl, propyl, isopropyl, butyl, isobutyl, sec-butyl, t-butyl, pentyl, 1-ethylpropyl, hexyl, heptyl, 1-ethylpentyl, 2,2,2-trifluoroethyl, allyl, 2-butenyl, 3-butenyl, 1,3-pentadienyl, 2-propynyl or 3-butynyl; or phenyl, benzyl, 1-phenylethyl, 2-phenylethyl, thien-2-ylmethyl, thien-3-ylmethyl, 1-phenylpropyl, 2-phenylpropyl, 3-phenylpropyl, 1-methyl-1-phenylethyl or 1-phenylbutyl: in which the alkyl moiety may optionally bear a methoxy, ethoxy, cyclobutyl, cyclopentyl, cyclohexyl or phenyl substituent and in which a phenyl or thienyl moiety may optionally bear 1 or 2 substituents selected from fluoro, chloro, bromo, methyl, ethyl, methoxy, ethoxy and trifluoromethyl; or Re is cyclopropyl, cyclobutyl, cyclopentyl, cyclohexyl, cycloheptyl, cyclobutylmethyl, cyclopentylmethyl, cyclohexylmethyl, 1-cyclopentylethyl, 2-cyclopentylethyl, 1-cyclopentylpropyl, 1-cyclohexypropyl, 1-cyclopentylbutyl, 1-cyclohexylbutyl, tetrahydrofur-2-yl, tetrahydrofur-3-yl, tetrahydropyran-2-yl, tetrahydropyran-3-yl, tetrahydropyran-4-yl, cyclohexenyl, cyclohexenylmethyl or 1-(cyclohexenyl)butyl: in which the cyclic moiety optionally may bear 1 or 2 methyl, ethyl, isopropyl or phenyl substituents, the latter itself optionally bearing a fluoro, chloro, bromo, methyl, methoxy or trifluoromethyl substituent; Q is a direct link to $G^1$, or is oxy, thio, m-phenylene, p-phenylene, 2,5-furandiyl, 2,5-thiophenediyl or 4,7-benzo[b]furandiyl; $G^1$ is methylene, ethylene, ethylidene, trimethylene, tetramethylene, pentamethylene, hexamethylene, heptamethylene, octamethylene, vinylene, propenylene, 1-butenylene or 2-butenylene; Rg is methyl, ethyl, propyl, isopropyl or butyl, or is phenyl, 1-naphthyl, 2-naphthyl, furyl, thienyl, benzyl, 1-naphthylmethyl, 2-naphthylmethyl, furylmethyl or thienylmethyl: the aromatic or heteroaromatic moiety of which optionally may bear 1 to 2 substituents independently selected from fluoro, chloro, bromo, methyl, ethyl, methoxy, ethoxy, trifluoromethyl, nitro and amino; and Rh is hydrogen, carboxymethyl, 2-carboxyethyl or o-carboxyphenylmethyl.

3. A compound as claimed in claim 2 wherein Ra is hydrogen, methyl, ethyl, chloro, bromo, acetyl, propionyl, butyryl, allyl, 2-carboxyvinyl, 2-(methoxycarbonyl)vinyl or 2-(methoxycarbonyl)ethyl; and Rb when present is hydrogen or methyl; or Ra and Rb together form tetramethylene or 1,3-butadienylene optionally bearing a methyl or ethyl substituent; Rc is hydrogen, methyl, chloro or bromo; Rd and Rf are independently selected from hydrogen, methyl, methoxy, fluoro, chloro and bromo; Re is ethyl, propyl, isopropyl, butyl, isobutyl, sec-butyl, t-butyl, pentyl, 1-ethylpropyl, hexyl, heptyl, 1-ethylpentyl, 1,3-pentadienyl, 3-butynyl, phenyl, 4-methylphenyl, 2-trifluoromethylphenyl, benzyl, 4-chlorobenzyl, 4-trifluoromethylbenzyl, 4-methylbenzyl, 1-phenylethyl, 2-phenylethyl, 1-methyl-1-phenylethyl, thien-2-ylmethyl, 1-phenylpropyl, alpha-cyclopentylbenzyl, alpha-methoxybenzyl, benzhydryl, cyclobutyl, cyclopentyl, cyclohexyl, 1-phenylcyclopentyl, cyclopentylmethyl, cyclohexylmethyl, 2-cyclopentylethyl, 1-cyclopentylbutyl, 1-cyclohexylpropyl, 1-cyclohexylbutyl, 5-methyl-2-(1-methylethyl)cyclohexyl, 1-cyclohexen-4-yl, tetrahydrofur-2-yl or tetrahydrofur-3-yl;

Q, including the optional substituents Rd and Rf, is a direct link, oxy, thio, m-phenylene, 2-methoxy-1,3-phenylene, 4-methoxy-1,3-phenylene, p-phenylene, 2-methoxy-1,4-phenylene, 2-methyl-1,4-phenylene, 2-fluoro-1,4-phenylene, 2-chloro-1,4-phenylene, 2-bromo-1,4-phenylene, 2,6-dimethoxy-1,4-phenylene, 2,5-furandiyl, or 4,7-benzo[b]furandiyl: in which Q is attached to $G^1$ at position 1 or 4; $G^1$ (when Q is optionally substituted phenylene, or 2,5-furandiyl or 4,7-benzo[b]furandiyl as defined above) is methylene or ethylidene, or (when Q is oxy or thio) is trimethylene, pentamethylene, heptamethylene or 2-butenylene; or (when Q is a direct link) is ethylene, trimethylene, tetramethylene, pentamethylene, hexamethylene or heptamethylene; Rg is methyl, isopropyl, butyl, phenyl, 4-fluorophenyl, 4-chlorophenyl, 2-methylphenyl, 4-methylphenyl, 4-methoxyphenyl, 4-nitrophenyl, 2-aminophenyl, 1-naphthyl or thien-2-yl; and Rh is hydrogen, carboxymethyl or o-carboxyphenylmethyl.

4. A compound as claimed in claim 1 wherein the group A═CRa stands for a diradical of the formula —CRb═CRa—.

5. A compound as claimed in claim 1 wherein Ra is hydrogen, chloro, acetyl, butyryl and Rb, when present, is hydrogen; Rc, Rf, and Rh are hydrogen; the group Re.L stands for a group of the formula Re.X.CO.NH— wherein the radical Re.X.CO is selected from branched (4-10C)alkanoyl, 2-{(4-6C)cycloalkyl)}acetyl, 2-{(2-5C)alkyl}-2-phenylacetyl, (4-6C)cycloalkyloxycarbonyl, (4-6C)cycloalkylthiolocarbonyl, (4-6C)cycloalkylcarbonyl and (3-6C)alkyloxycarbonyl; the assembly $G^1.Q.G^2$ (together with Rd) is 2-methoxy-alpha,4-toluenediyl; Rg is phenyl optionally bearing a fluoro, chloro, methyl, nitro or amino substituent; and n is 2.

6. A compound as claimed in claim 5 wherein the group Re.L is located in the 6 position of the nucleus.

7. A compound as claimed in any one of claims 1–6 wherein Z is an acylsulphonamide residue of the formula —CO.NHSO$_2$Rg wherein Rg has any of the meanings defined in any one of claims 1–6.

8. A compound of the formula I claimed in claim 1 selected from:
a)  N-(4-[6-(cyclopentyloxycarbonyl)aminoindol-1-ylmethyl]3-methoxybenzoyl)benzenesulphonamide;
b) N-(4-[6-(2-cyclopentylacetamido)indol-1-ylmethyl]3-methoxybenzoyl)-o-toluenesulphonamide;
c)  2-amino-N-(4-[6-(2-cyclopentylacetamido)indol-1-ylmethyl]3-methoxybenzoyl)benzenesulphonamide;
d)  N-(4-[3-acetyl-6-(cyclopentyloxycarbonyl)aminoindol-1-ylmethyl]-3-methoxybenzoyl)benzenesulphonamide;
e)  N-(4-[6-(cyclopentylcarbonyl)aminoindol-1-ylmethyl]3-methoxybenzoyl)benzenesulphonamide;
f)  N-(4-[3-chloro-6-(2-cyclopentylacetamido)indol-1-ylmethyl]3-methoxybenzoyl)benzenesulphonamide;
g)  N-(4-[6-(2-cyclopentylacetamido)indolin-1-ylmethyl]3-methoxybenzoyl)benzenesulphonamide;
h) N-(4-[6-(2-cyclopentylacetamido)indol-1-ylmethyl]3-methoxybenzoyl)benzenesulphonamide;
i)  N-(4-[3-butyryl-6-(2-cyclopentylacetamido)indol-1-ylmethyl]3-methoxybenzoyl)benezenesulphonamide;
j)  4-(6-[2-cyclopentylacetamido]indol-1-ylmethyl)-3-methoxybenzoic acid;
k)  4-(6-[cyclobutyloxycarbonyl]aminoindol-1-ylmethyl)-3-methoxybenzoic acid;
l)  4-(6-[cyclopentyloxycarbonyl]aminoindol-1-ylmethyl)-3-methoxybenzoic acid;
m)  4-(6-[2-cyclohexylacetamido]indol-1-ylmethyl)-3-methoxybenzoic acid;
n) 4-(3-chloro-6-[cyclopentyloxycarbonyl]aminoindol-1-ylmethyl)3-methoxybenzoic acid;
o) 4-(3-acetyl-6-[cyclopentyloxycarbonyl]aminoindol-1-ylmethyl)3-methoxybenzoic acid;
p) 4-(3-chloro-6-[2-cyclopentylacetamido]indol-1-ylmethyl3-methoxybenzoic acid;
q)  4-(3-[2-(methoxycarbonyl)vinyl]-6-[2-ethylhexanamido]indol-1-ylmethyl)-3-methoxybenzoic acid;
r)  6-(butoxycarbonyl)amino-1-(2-methoxy-4-[1(H)-tetrazol-5-yl]benzyl)indole; and
s)  6-(cyclopentyloxycarbonyl)amino-1-(2-methoxy-4-[1(H)-tetrazol-5-yl]benzyl)indole;
or a pharmaceutically acceptable salt thereof.

9. A compound as claimed in claim 8 which is N-(4-[6-(cyclopentyloxycarbonyl)aminoindol-1-ylmethyl]3-methoxylbenzoyl)benzenesulphonamide; or a pharmaceutically acceptable salt thereof.

10. A salt as claimed in any one of claims 1, 2, 3, 4, 5, 6, 8 and 9 which is a salt with a base forming a physiologically acceptable cation.

11. A compound of the formula V

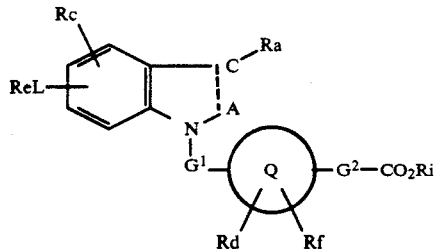

wherein Ri is (1-6C)alkyl optionally bearing an acetoxy, (1-4C)alkoxy or (1-4C)alkylthio substituent, or is phenyl or benzyl; and wherein the groups A═CRa, Rb, Rc, Rd, Re, Rf, $G^1$, $G^2$, Q and L have the meanings defined in claim 1.

12. A pharmaceutical composition which comprises a compound of formula I or a pharmaceutically acceptable salt thereof, as claimed in claim 1, together with a pharmaceutically acceptable diluent or carrier.

13. A method for antagonising one or more of the actions of leukotrienes in a living mammal comprising administering to said mammal an effective amount of a compound claimed in claim 1.

14. A method as claimed in claim 13 for the treatment of an allergic pulmonary disorder.

15. A method as claimed in claim 14 for the treatment of asthma.

* * * * *